US012773129B2

(12) United States Patent
Kumar et al.

(10) Patent No.: US 12,773,129 B2
(45) Date of Patent: Oct. 27, 2026

(54) GAIT AND POSTURE ANALYSIS

(71) Applicant: The Jackson Laboratory, Bar Harbor, ME (US)

(72) Inventors: Vivek Kumar, Bar Harbor, ME (US); Keith Sheppard, Bar Harbor, ME (US); Gautam Sabnis, Bar Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 583 days.

(21) Appl. No.: 18/260,006

(22) PCT Filed: Dec. 29, 2021

(86) PCT No.: PCT/US2021/065425
§ 371 (c)(1),
(2) Date: Oct. 3, 2023

(87) PCT Pub. No.: WO2022/147063
PCT Pub. Date: Jul. 7, 2022

(65) Prior Publication Data

US 2024/0057892 A1 Feb. 22, 2024

Related U.S. Application Data

(60) Provisional application No. 63/144,052, filed on Feb. 1, 2021, provisional application No. 63/131,498, filed on Dec. 29, 2020.

(51) Int. Cl.

| | |
|---|---|
| ***A61B 5/11*** | (2006.01) |
| ***A61B 5/00*** | (2006.01) |
| ***G16H 30/20*** | (2018.01) |
| ***G16H 30/40*** | (2018.01) |

(52) U.S. Cl.
CPC ............ *A61B 5/1116* (2013.01); *A61B 5/112* (2013.01); *A61B 5/1128* (2013.01);
(Continued)

(58) Field of Classification Search
None
See application file for complete search history.

(56) References Cited

U.S. PATENT DOCUMENTS

2009/0162859 A1 6/2009 Rosenfeld et al.
2009/0296992 A1 12/2009 Liang et al.
(Continued)

FOREIGN PATENT DOCUMENTS

JP 2008-113872 5/2008

OTHER PUBLICATIONS

Timotius IK, et al. Silhouette-Length-Scaled Gait Parameters for Motor Functional Analysis in Mice and Rats. eNeuro. Nov. 1, 2019;6 (6): doi: 10.1523/ENEURO.0100-19.2019. PMID: 31 (Year: 2019).*

(Continued)

*Primary Examiner* — Adam J Eiseman
*Assistant Examiner* — Nelson Alexander Glover
(74) *Attorney, Agent, or Firm* — McDonnell Boehnen Hulbert & Berghoff LLP

(57) ABSTRACT

Systems and methods described herein provide techniques for analyzing gait and posture of a subject with respect to control data. The systems and methods, in some embodiments, processes video data, identifies keypoints representing body parts, determines metrics data at a stride level, and compares the metrics data to control data.

20 Claims, 70 Drawing Sheets

(52) U.S. Cl.
CPC ........... *A61B 5/7267* (2013.01); *G16H 30/20* (2018.01); *G16H 30/40* (2018.01); *A61B 2503/00* (2013.01)

(56) References Cited

U.S. PATENT DOCUMENTS

| | | | | |
|---|---|---|---|---|
| 2010/0222709 | A1* | 9/2010 | Lepine | A01K 29/00 600/595 |
| 2016/0081594 | A1* | 3/2016 | Gaddipati | A61B 5/4824 600/595 |
| 2016/0192865 | A1 | 7/2016 | Datta et al. | |
| 2019/0298226 | A1 | 10/2019 | Filipowicz | |
| 2020/0050840 | A1* | 2/2020 | Neckel | G06V 20/653 |
| 2020/0197744 | A1* | 6/2020 | Schweighofer | A61B 5/1128 |
| 2021/0330637 | A1* | 10/2021 | Abrishami | A61K 31/352 |

OTHER PUBLICATIONS

Batka, R.J. et al. (2014), The Need for Speed in Rodent Locomotion Analyses. The Anatomical Record, 297: 1839-1864. https://doi.org/10.1002/ar.22955 (Year: 2014).*

Ana S. Machado et al. (2015) A quantitative framework for whole-body coordination reveals specific deficits in freely walking ataxic mice. eLife 4:e07892. (Year: 2015).*

Bifulco, P. et al. A continuous description of intervertebral motion by means of spline interpolation of kinematic data extracted by videofluoroscopy. Journal of Biomechanics. 45 (2012) 634â641. (Year: 2012).*

Orekhov G. et al. (2019) Knee joint biomechanics in transtibial amputees in gait, cycling, and elliptical training. PLOS ONE 14(12): e0226060. https://doi.org/10.1371/journal.pone.0226060 (Year: 2019).*

Extended European Search Report from European Application No. 21916381.3, dated Sep. 20, 2024.

Daniel F. Preisig, et al., "High-speed video gait analysis reveals early and characteristic locomotor phenotypes in mouse models of neurodegenerative movement disorders," Behavioural Brain Research, 311 (2016) 340-353, 2016.

Robert Fiker et al., "Visual Gait Lab: A user-friendly approach to gait analysis," Journal of Neuroscience Methods, 341 (2020) 108775. May 2020.

International Search Report dated Mar. 14, 2022 for International Application No. PCT/US2021/065425, 2 pages.

* cited by examiner

Fig. 7A
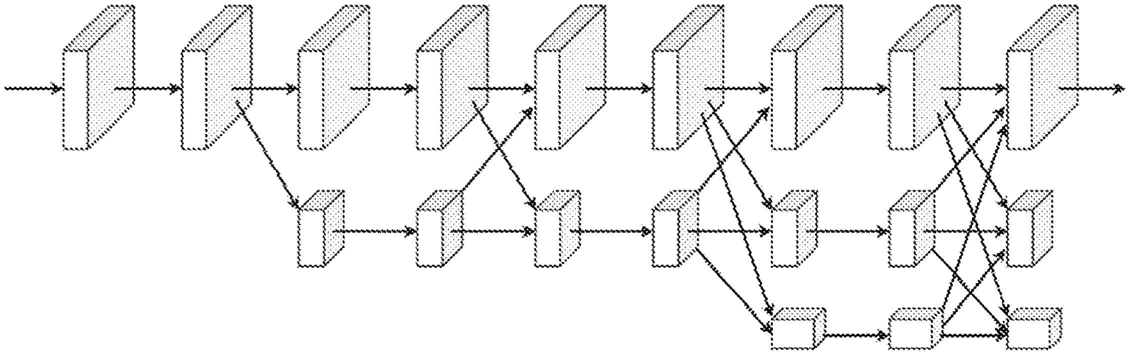
Fig. 7B
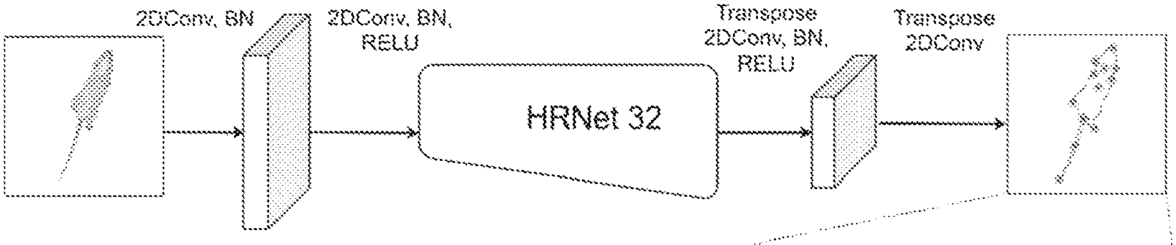
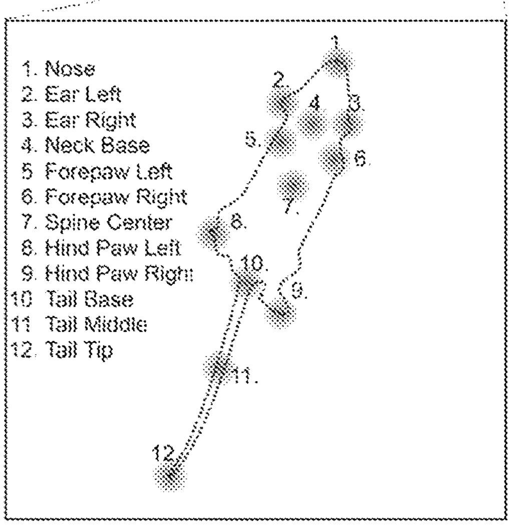
Fig. 7C
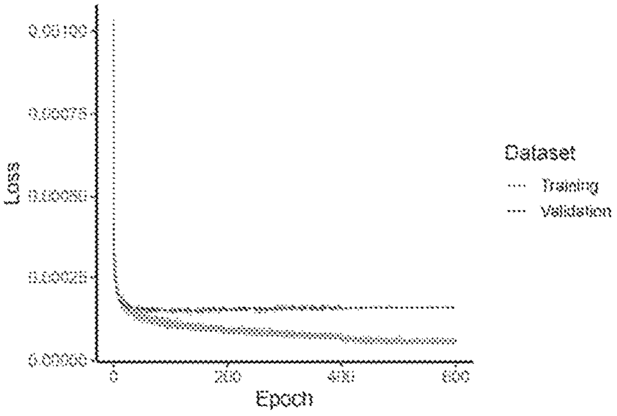

Fig. 9A
Fig. 9B
Fig. 9C
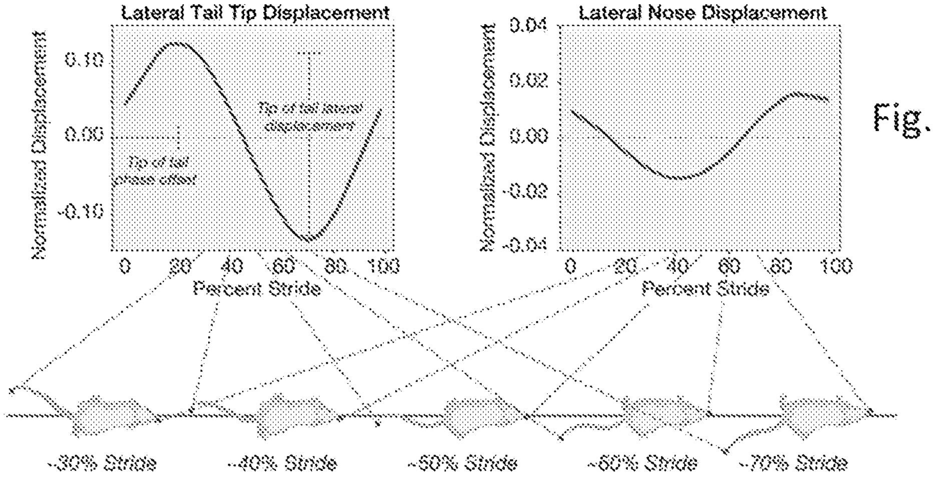
Fig. 9D
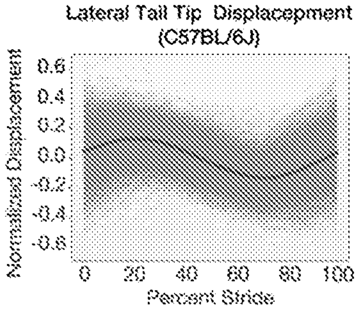
Fig. 9E
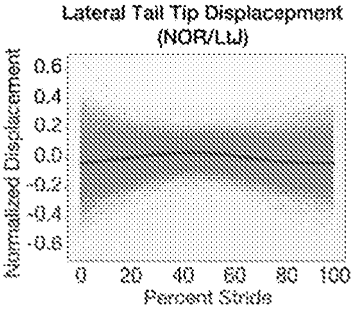
Fig. 9F
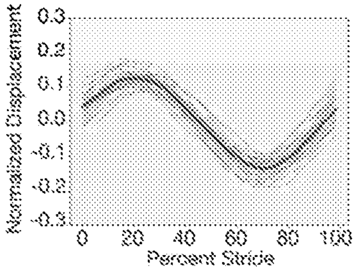
Fig. 9G
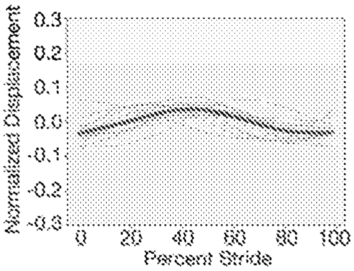
Fig. 9H
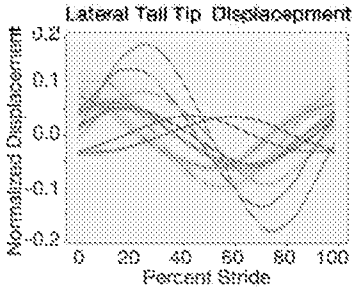
Fig. 9I
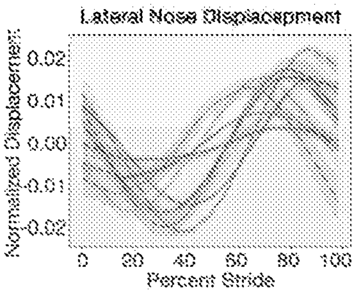
AKR/J BALB/cByJ BTBR C57BL/6NJ C57BL/6J
CAF1/J CBA/CaJ CBA/J LG/J NOR/LtJ -log(P-value)
All Mean Phenotypes -log(P-value)
All Variance Phenotypes -log(P-value)
All Phenotypes

FIG. 14A

| Measure | Definition of Measure | Units |
|---|---|---|
| Angular Velocity | The current angle of a mouse is determined by the vector connecting the mouse's base of tail to its base of neck. The first derivative of this value gives us angular velocity. For strides, angular velocity is averaged over the duration of the stride. | degrees/sec |
| Speed | The speed of a mouse is determined by tracking the movement speed of the base of tail keypoint. Stride speed is the average speed for all frames over the duration of a stride. | cm/sec |
| Limb Duty Factor | The stance time of a paw (the amount of time that the paw is in contact with the ground) divided by the full stride time. Duty factor is calculated for each of the hind paws and averaged. | None |
| Step Length | The distance that the right hind paw travels past the previous left hind paw strike | cm |
| Step Width | The averaged lateral distance separating hind paws. This is calculated as length of the shortest line segment that connects the right hind paw strike to the line that connects the left hind paw's toe-off location to its subsequent foot strike position. | cm |
| Stride Length | The full distance that the left hind paw travels for a stride, from toe-off to foot-strike. | cm |
| Lateral Displacement of Nose | In order to calculate lateral displacement, we first calculate the mouse's displacement vector for a stride. We then measure the nose's perpendicular distance from this vector for each frame of a stride. We now subtract the minimum distance from the maximum and divide by the mouse's body length so that the displacement measured in larger mice will be comparable to the distance measured in smaller mice. | None |
| Lateral Displacement of Base Of Tail | Calculated using the same approach which is applied to the Nose Lateral Displacement except that we are using the Base of Tail keypoint. | None |
| Lateral Displacement of Tip of Tail | Calculated using the same approach which is applied to the Nose Lateral Displacement except that we are using the Tip of Tail keypoint. | None |
| Nose Lateral Displacement Phase Offset | First, the lateral displacement is calculated for each frame of a stride as described for Nose Lateral Displacement above. We then perform a cubic spline interpolation in order to generate a smooth curve for displacement. We then determine the point in time where maximum displacement occurs. Note that because of cubic interpolation this can occur at time points between frames. | Percent Stride Cycle |
| Base of Tail Displacement Phase Offset | Calculated using the same approach which is applied to the Nose Lateral Displacement Phase Offset except that we are using the Base of Tail keypoint. | Percent Stride Cycle |
| Tip of Tail Displacement Phase Offset | Calculated using the same approach which is applied to the Nose Lateral Displacement Phase Offset except that we are using the Tip of Tail keypoint. | Percent Stride Cycle |

FIG. 14B

| Strain | JMCRS # | Genotype | Sex | Short Name | Control Strain |
|---|---|---|---|---|---|
| B6.129P2(C)-Mecp2$^{tm1.1Bird}$/J | 003890 | HEMI | M | Mecp2 | Littermate WT |
| B6.129P2(C)-Mecp2$^{tm1.1Bird}$/J | 003890 | HET | F | Mecp2 | Littermate WT |
| B6.Cg-Tg(SOD1*G93A)1Gur/J | 004435 | HEMI | M/F | Sod1 | Littermate WT |
| B6EiC3Sn.BLiA-Ts(17$^{16}$)65Dn/DnJ | 005252 | Trisomic | M/F | Ts65Dn | B6EiC3Sn.BLiAF1/J |
| B6EiC3Sn.BLiAF1/J | 003647 | F1 | M/F | | N/A |

FIG. 14C

| Strain | JMCRS # | Short Name | Control Strain |
|---|---|---|---|
| B6.129P2-*Fmr1*$^{tm1Cgr}$/J | 003025 | *Fmr1* | C57BL/6J |
| B6129S-Del(7Slx1b-Sept1)4Aam/J | 013128 | *Del4Aam* | B6129SF1/J |
| B6.129-Shank3$^{tm2Gfn}$/J | 017688 | *Shank3* | C57BL/6J |
| B6.129(Cg)-Cntnap2$^{tm1Pele}$/J | 028635 | *Cntnap2* | C57BL/6J |
| B6129SF1/J | 101043 | | N/A |
| C57BL/6J | 000664 | | N/A |

FIG. 14D

| Gait Mutants | | | | | | |
|---|---|---|---|---|---|---|
| Strain | Sex | BodyLength | | Correlation | BodyWeight | |
| | | Control | Mutant | *r* | Control | Mutant |
| *Sod1* | M | 6.16 ± .15 | 6.23 ± .26 | 0.48 | 28.90 ± 2.69 | 26.41 ± 2.25 |
| | F | 5.53 ± .31 | 5.47 ± .32 | 0.76 | 21.74 ± 2.38 | 20.08 ± 1.84 |
| *Ts65Dn* | M | 5.90 ± .29 | 5.75 ± .37 | 0.73 | 30.46 ± 4.16 | 29.39 ± 6.39 |
| | F | 5.55 ± .24 | 5.77 ± .42 | 0.73 | 23.28 ± 2.20 | 25.51 ± 6.59 |
| *Mecp2* | M | 5.69 ± .23 | 4.82 ± .31 | 0.94 | 23.53 ± 1.77 | 15.68 ± 1.81 |
| | F | 5.25 ± .35 | 5.33 ± .37 | 0.91 | 19.31 ± 3.09 | 19.86 ± 3.27 |
| Autism Mutants | | | | | | |
| *Cntnap2* | M | 6.03 ± .37 | 5.56 ± .28 | 0.72 | 28.28 ± 1.95 | 23.95 ± 1.71 |
| | F | 5.65 ± .25 | 5.41 ± .29 | 0.72 | 22.69 ± 2.05 | 19.40 ± 0.97 |
| *Fmr1* | M | 6.03 ± .37 | 6.17 ± .20 | 0.77 | 28.28 ± 1.95 | 29.49 ± 1.37 |
| | F | 5.65 ± .25 | 5.66 ± .17 | 0.47 | 22.69 ± 2.05 | 21.01 ± 1.12 |
| *Shank3* | M | 6.03 ± .37 | 6.00 ± .11 | 0.75 | 28.28 ± 1.95 | 28.24 ± 1.00 |
| | F | 5.65 ± .25 | 5.60 ± .23 | 0.70 | 22.69 ± 2.05 | 21.60 ± 1.70 |
| *Del4Aam* | M | 6.42 ± .36 | 6.18 ± .51 | 0.70 | 33.13 ± 3.21 | 23.22 ± 2.43 |
| | F | 5.50 ± .29 | 5.84 ± .40 | 0.70 | 21.29 ± 1.49 | 18.16 ± 2.32 |

FIG. 14E

| | Strain | N | Males | Females |
|---|---|---|---|---|
| 1 | 129P3/J | 23 | 8 | 15 |
| 2 | 129S1/SvImJ | 17 | 13 | 4 |
| 3 | 129X1/SvJ | 15 | 8 | 7 |
| 4 | A/J | 6 | 4 | 2 |
| 5 | AKR/J | 17 | 9 | 8 |
| 6 | B6129PF1/J | 30 | 10 | 20 |
| 7 | B6129SF1/J | 24 | 15 | 9 |
| 8 | B6AF1/J | 35 | 17 | 18 |
| 9 | B6C3F1/J | 32 | 12 | 20 |
| 10 | B6CBAF1/J | 18 | 9 | 9 |
| 11 | B6D2F1/J | 22 | 12 | 10 |
| 12 | B6SJLF1/J | 28 | 5 | 23 |
| 13 | BALB/cByJ | 18 | 11 | 7 |
| 14 | BALB/cJ | 21 | 19 | 2 |
| 15 | BTBR T<+>Itpr3<tf>/J | 53 | 32 | 21 |
| 16 | BUB/BnJ | 15 | 7 | 8 |
| 17 | C3H/HeJ | 27 | 11 | 16 |
| 18 | C3H/HeOuJ | 19 | 6 | 13 |
| 19 | C3HeB/FeJ | 10 | 5 | 5 |
| 20 | C57BL/10SnJ | 19 | 10 | 9 |
| 21 | C57BL/6J | 494 | 298 | 196 |
| 22 | C57BL/6NJ | 293 | 126 | 167 |
| 23 | C57BLKS/J | 30 | 19 | 11 |
| 24 | C57BR/cdJ | 15 | 3 | 12 |
| 25 | C57L/J | 23 | 10 | 13 |
| 26 | C58/J | 11 | 7 | 4 |
| 27 | CAF1/J | 14 | 8 | 6 |
| 28 | CAST/EiJ | 33 | 10 | 23 |
| 29 | CB6F1/J | 27 | 18 | 9 |
| 30 | CBA/CaJ | 30 | 15 | 15 |
| 31 | CBA/J | 14 | 9 | 5 |
| 32 | CByB6F1/J | 18 | 14 | 4 |
| 33 | CZECHII/EiJ | 11 | 4 | 7 |
| 34 | DBA/1J | 27 | 12 | 15 |
| 35 | DBA/2J | 17 | 8 | 9 |
| 36 | FVB/NJ | 13 | 5 | 8 |
| 37 | I/LnJ | 14 | 6 | 8 |
| 38 | KK/HlJ | 8 | 5 | 3 |
| 39 | LG/J | 6 | 3 | 3 |
| 40 | LP/J | 25 | 15 | 10 |
| 41 | MA/MyJ | 15 | 7 | 8 |
| 42 | MOLF/EiJ | 9 | 3 | 6 |
| 43 | MRL/MpJ | 12 | 4 | 8 |
| 44 | MSM/MsJ | 11 | 3 | 8 |
| 45 | NOD/ShiLtJ | 25 | 13 | 12 |
| 46 | NON/ShiLtJ | 27 | 13 | 14 |
| 47 | NOR/LtJ | 13 | 7 | 6 |
| 48 | NU/J | 10 | 5 | 5 |
| 49 | NZB/BlNJ | 21 | 5 | 16 |
| 50 | NZBWF1/J | 17 | 9 | 8 |
| 51 | NZO/HlLtJ | 14 | 6 | 8 |
| 52 | NZW/LacJ | 11 | 7 | 4 |
| 53 | PL/J | 12 | 4 | 8 |
| 54 | PWD/PhJ | 12 | 7 | 5 |
| 55 | PWK/PhJ | 9 | 5 | 4 |
| 56 | RIIIS/J | 10 | 3 | 7 |
| 57 | SEA/GnJ | 7 | 4 | 3 |
| 58 | SJL/J | 34 | 4 | 30 |
| 59 | SM/J | 12 | 8 | 4 |
| 60 | SWR/J | 12 | 2 | 10 |
| 61 | TALLYHO/JngJ | 22 | 13 | 9 |
| 62 | WSB/EiJ | 11 | 8 | 3 |

FIG. 19

| M1 : Phenotype ~ Genotype + TestAge + BodyLength + (1 \| MouseID/TestAge) | | | | | | | | |
|---|---|---|---|---|---|---|---|---|
| Phenotype | Sod1 | | Ts65Dn | | Mecp2 (Het) | | Mecp2 (Hemi) | |
| | Effect size | $P_{adj}$ | Effect size | $P_{adj}$ | Effect size | $P_{adj}$ | Effect size | $P_{adj}$ |
| Angular Velocity | 0.02 | 0.69 | 0.04 | 0.69 | 0.02 | 0.69 | -0.25 | 0.37 |
| Speed | -0.21 | 0.00 | 0.15 | 0.04 | -0.38 | 0.00 | -0.53 | 0.00 |
| Limb Duty | 0.23 | 0.00 | -0.10 | 0.21 | 0.03 | 0.74 | 0.27 | 0.18 |
| Step Length | -0.12 | 0.34 | -0.24 | 0.02 | -0.10 | 0.37 | -0.38 | 0.28 |
| Step Width | -0.09 | 0.56 | 0.59 | 0.00 | 0.16 | 0.48 | -0.79 | 0.02 |
| Stride Length | -0.30 | 0.01 | -0.35 | 0.01 | -0.33 | 0.06 | -0.60 | 0.01 |
| Temporal Symmetry | -0.09 | 0.24 | 0.12 | 0.15 | -0.00 | 0.96 | 0.09 | 0.64 |
| Amplitude Tail Base | 0.23 | 0.11 | -0.46 | 0.03 | 0.34 | 0.11 | 0.40 | 0.09 |
| Amplitude Tail Tip | 0.16 | 0.12 | -0.37 | 0.00 | 0.50 | 0.01 | 0.99 | 0.00 |
| Amplitude Nose | 0.02 | 0.73 | -0.16 | 0.16 | 0.09 | 0.53 | 0.09 | 0.53 |
| Phase Tail Base | 0.02 | 0.11 | -0.05 | 0.00 | 0.00 | 0.39 | 0.04 | 0.01 |
| Phase Tail Tip | 0.09 | 0.16 | -1.37 | 0.00 | -0.17 | 0.02 | 0.50 | 0.00 |
| Phase Nose | -0.06 | 0.01 | -0.64 | 0.00 | -0.05 | 0.06 | -0.18 | 0.00 |
| M2 : Phenotype ~ Genotype + TestAge + Speed + (1 \| MouseID/TestAge) | | | | | | | | |
| Angular Velocity | 0.02 | 0.68 | 0.03 | 0.68 | 0.02 | 0.68 | -0.14 | 0.28 |
| Limb Duty | 0.14 | 0.12 | -0.03 | 0.71 | -0.10 | 0.36 | -0.23 | 0.02 |
| Step Length | -0.08 | 0.66 | -0.23 | 0.15 | 0.03 | 0.83 | -0.77 | 0.00 |
| Step Width | -0.12 | 0.59 | 0.59 | 0.00 | 0.14 | 0.59 | -1.12 | 0.00 |
| Stride Length | -0.24 | 0.16 | -0.39 | 0.02 | -0.11 | 0.59 | -1.09 | 0.00 |
| Temporal Symmetry | -0.04 | 0.65 | 0.08 | 0.45 | 0.04 | 0.65 | 0.34 | 0.00 |
| Amplitude Tail Base | 0.21 | 0.15 | -0.45 | 0.03 | 0.28 | 0.15 | 0.30 | 0.15 |
| Amplitude Tail Tip | 0.13 | 0.17 | -0.37 | 0.00 | 0.46 | 0.01 | 0.90 | 0.00 |
| Amplitude Nose | -0.00 | 0.95 | -0.14 | 0.21 | 0.05 | 0.87 | 0.04 | 0.87 |
| Phase Tail Base | 0.01 | 0.22 | -0.05 | 0.00 | 0.01 | 0.34 | 0.00 | 0.08 |
| Phase Tail Tip | 0.00 | 0.29 | -4.55* | 0.01 | -10.50* | 0.06 | 0.28 | 0.00 |
| Phase Nose | -0.08 | 0.05 | -8.14* | 0.00 | -0.09 | 0.13 | -4.12* | 0.00 |
| M3 : Phenotype ~ Genotype + TestAge + Speed + BodyLength + (1 \| MouseID/TestAge) | | | | | | | | |
| Angular Velocity | 0.02 | 0.67 | 0.03 | 0.67 | 0.02 | 0.67 | -0.24 | 0.42 |
| Limb Duty | 0.14 | 0.13 | -0.03 | 0.79 | -0.12 | 0.26 | 0.04 | 0.79 |
| Step Length | -0.07 | 0.65 | -0.27 | 0.01 | -0.01 | 0.92 | -0.28 | 0.55 |
| Step Width | -0.11 | 0.49 | 0.60 | 0.00 | 0.12 | 0.49 | -0.81 | 0.02 |
| Stride Length | -0.22 | 0.07 | -0.40 | 0.00 | -0.18 | 0.32 | -0.41 | 0.07 |
| Temporal Symmetry | -0.05 | 0.41 | 0.09 | 0.31 | 0.06 | 0.41 | 0.18 | 0.31 |
| Amplitude Tail Base | 0.21 | 0.19 | -0.45 | 0.03 | 0.28 | 0.19 | -0.35 | 0.23 |
| Amplitude Tail Tip | 0.13 | 0.17 | -0.37 | 0.00 | 0.46 | 0.01 | 0.90 | 0.00 |
| Amplitude Nose | -0.00 | 0.95 | -0.14 | 0.21 | 0.05 | 0.87 | 0.04 | 0.87 |
| Phase Tail Base | 0.01 | 0.34 | -0.05 | 0.00 | 0.01 | 0.34 | 0.00 | 0.34 |
| Phase Tail Tip | 0.00 | 0.03 | -2.96* | 0.00 | -0.71 | 0.22 | 0.21 | 0.01 |
| Phase Nose | -0.08 | 0.05 | -5.60* | 0.00 | -275.28* | 0.22 | -8.24* | 0.00 |

FIG. 20

| M1 : Phenotype ~ Genotype + BodyLength + Sex + (1 \| MouseID) | | | | | | | | |
|---|---|---|---|---|---|---|---|---|
| Phenotype | *Cntnap2* | | *Fmr1* | | *Shank3* | | *Del4Aam* | |
| | Effect size | Padj | Effect size | Padj | Effect size | Padj | Effect size | Padj |
| Angular Velocity | 0.51 | 0.79 | 0.13 | 0.83 | 0.13 | 0.83 | -0.17 | 0.83 |
| Speed | 1.07 | 0.00 | 0.64 | 0.00 | -0.90 | 0.00 | 0.77 | 0.02 |
| Limb Duty | 0.02 | 0.00 | 0.01 | 0.10 | 0.00 | 0.84 | -0.01 | 0.41 |
| Step Length | -0.19 | 0.13 | 0.03 | 0.77 | 0.23 | 0.08 | -0.18 | 0.08 |
| Step Width | -0.17 | 0.01 | -0.08 | 0.15 | -0.04 | 0.50 | -0.01 | 0.90 |
| Stride Length | -0.59 | 0.00 | 0.04 | 0.68 | 0.13 | 0.25 | -0.23 | 0.08 |
| Temporal Symmetry | 0.00 | 0.66 | -0.01 | 0.21 | -0.01 | 0.21 | -0.00 | 0.87 |
| Amplitude Tail Base | -0.01 | 0.01 | -0.01 | 0.08 | -0.00 | 0.45 | -0.02 | 0.01 |
| Amplitude Tail Tip | 0.02 | 0.29 | -0.03 | 0.27 | -0.06 | 0.02 | -0.04 | 0.14 |
| Amplitude Nose | -0.02 | 0.00 | -0.01 | 0.07 | -0.00 | 0.49 | -0.01 | 0.07 |
| Phase Tail Base | 0.07 | 0.00 | 0.02 | 0.19 | 0.00 | 0.49 | -0.02 | 0.24 |
| Phase Tail Tip | 0.71 | 0.00 | -0.03 | 0.39 | -0.12 | 0.15 | 0.52 | 0.00 |
| Phase Nose | -0.09 | 0.00 | -0.01 | 0.28 | -0.12 | 0.00 | -0.11 | 0.04 |
| M2 : Phenotype ~ Genotype + Speed + (1 \| MouseID) | | | | | | | | |
| Angular Velocity | 0.35 | 0.96 | 0.16 | 0.96 | 0.05 | 0.96 | -0.04 | 0.96 |
| Limb Duty | 0.03 | 0.00 | 0.02 | 0.01 | -0.01 | 0.12 | 0.00 | 0.85 |
| Step Length | -0.40 | 0.00 | 0.01 | 0.91 | 0.26 | 0.05 | -0.27 | 0.05 |
| Step Width | -0.21 | 0.00 | -0.06 | 0.36 | -0.05 | 0.36 | -0.01 | 0.87 |
| Stride Length | -0.91 | 0.00 | -0.01 | 0.94 | 0.21 | 0.11 | -0.38 | 0.08 |
| Temporal Symmetry | 0.00 | 0.66 | -0.02 | 0.09 | -0.01 | 0.66 | -0.01 | 0.66 |
| Amplitude Tail Base | -0.01 | 0.01 | -0.01 | 0.10 | -0.00 | 0.36 | -0.02 | 0.01 |
| Amplitude Tail Tip | 0.02 | 0.24 | -0.03 | 0.24 | -0.07 | 0.01 | -0.04 | 0.13 |
| Amplitude Nose | -0.02 | 0.00 | -0.00 | 0.14 | -0.00 | 0.23 | -0.01 | 0.14 |
| Phase Tail Base | 0.09 | 0.00 | 0.02 | 0.19 | -0.00 | 0.48 | -0.02 | 0.26 |
| Phase Tail Tip | 0.81 | 0.00 | -0.10 | 0.14 | -0.11 | 0.14 | 0.89 | 0.00 |
| Phase Nose | -0.30 | 0.00 | -0.03 | 0.16 | -0.21 | 0.01 | -0.09 | 0.07 |
| M3 : Phenotype ~ Genotype + Speed + BodyLength + (1 \| MouseID) | | | | | | | | |
| Angular Velocity | 0.54 | 0.68 | 0.11 | 0.98 | 0.05 | 0.98 | 0.02 | 0.98 |
| Limb Duty | 0.03 | 0.00 | 0.02 | 0.01 | -0.01 | 0.16 | 0.00 | 0.78 |
| Step Length | -0.26 | 0.04 | -0.01 | 0.91 | 0.28 | 0.03 | -0.24 | 0.03 |
| Step Width | -0.17 | 0.01 | -0.08 | 0.17 | -0.04 | 0.39 | 0.00 | 0.98 |
| Stride Length | -0.73 | 0.00 | -0.05 | 0.66 | 0.24 | 0.03 | -0.32 | 0.02 |
| Temporal Symmetry | -0.00 | 0.59 | -0.02 | 0.11 | -0.01 | 0.59 | -0.01 | 0.59 |
| Amplitude Tail Base | -0.02 | 0.00 | -0.01 | 0.11 | -0.01 | 0.34 | -0.02 | 0.00 |
| Amplitude Tail Tip | 0.02 | 0.24 | -0.03 | 0.24 | -0.07 | 0.01 | -0.04 | 0.13 |
| Amplitude Nose | -0.02 | 0.00 | -0.00 | 0.14 | -0.00 | 0.23 | -0.01 | 0.14 |
| Phase Tail Base | 0.09 | 0.00 | 0.02 | 0.19 | 0.00 | 0.47 | -0.02 | 0.26 |
| Phase Tail Tip | 0.31 | 0.00 | -0.29 | 0.01 | 0.07 | 0.35 | 0.39 | 0.00 |
| Phase Nose | -0.38 | 0.00 | -0.03 | 0.16 | -225.04 | 0.02 | -0.13 | 0.08 |

FIG. 22

| Chrom. | QTL peak SNP | QTL peak SNP position | QTL start position | QTL end position | Allele 1 | Allele 2 | Allele 1 frequency | P | p_wald | Protein coding genes | Groups QTL is significant in |
|---|---|---|---|---|---|---|---|---|---|---|---|
| 1 | rs36381057 | 8083777 | 3105854 | 12936651 | G | A | 0.768 | 4.996424 | 1.01E-05 | 33 | StepWidthVariance |
| 1 | rs31489976 | 19705448 | 11186867 | 29047621 | T | A | 0.332 | 7.483023 | 3.29E-08 | 58 | AngularVelocityVariance;StrideLength |
| 1 | rs32792242 | 32350897 | 22392993 | 40486886 | T | G | 0.117 | 5.049202 | 8.93E-06 | 93 | TemporalSymmetry;AmplitudeTailTipVariance |
| 1 | rs33003310 | 38316457 | 31889774 | 45332681 | T | C | 0.818 | 5.326581 | 4.71E-06 | 97 | TemporalSymmetry;AmplitudeTailTipVariance |
| 1 | rs51243291 | 78898181 | 76083418 | 83683690 | T | G | 0.082 | 6.623505 | 2.38E-07 | 43 | AmplitudeNoseVariance;StrideLengthVariance |
| 1 | rs30361966 | 93426683 | 86378921 | 1.01E+08 | T | C | 0.228 | 5.721312 | 1.90E-06 | 121 | AmplitudeNoseVariance |
| 1 | rs33227659 | 108934751 | 99720250 | 1.14E+08 | T | C | 0.922 | 5.389884 | 4.07E-06 | 25 | LimbDutyVariance;AmplitudeNoseVariance;StrideLengthVariance;TemporalSymmetryVariance |
| 1 | rs49734993 | 114756557 | 1.14E+08 | 1.15E+08 | T | A | 0.067 | 5.456964 | 3.49E-06 | NA | StrideLengthVariance |
| 1 | rs30727994 | 118626277 | 1.09E+08 | 1.29E+08 | T | C | 0.199 | 7.349077 | 4.48E-08 | 54 | AmplitudeTailBaseVariance;LimbDutyVariance;AmplitudeNose;AmplitudeNoseVariance;StrideLengthVariance;TemporalSymmetryVariance |
| 1 | rs33439460 | 126615759 | 1.21E+08 | 1.36E+08 | T | C | 0.847 | 7.883492 | 1.31E-08 | 123 | AmplitudeTailBaseVariance;AmplitudeNose;AmplitudeNoseVariance;StepWidthVariance;TemporalSymmetryVariance |
| 1 | rs46018747 | 128662040 | 1.24E+08 | 1.36E+08 | T | C | 0.796 | 5.729811 | 1.86E-06 | 118 | AmplitudeTailBaseVariance;AmplitudeNose;AmplitudeNoseVariance;StepWidthVariance;TemporalSymmetryVariance |
| 1 | rs33534620 | 132726570 | 1.27E+08 | 1.43E+08 | T | C | 0.912 | 14.73176 | 1.85E-15 | 144 | AmplitudeNose;StepWidthVariance;TemporalSymmetryVariance |
| 1 | rs30967465 | 144072658 | 1.34E+08 | 1.5E+08 | T | A | 0.916 | 4.818081 | 1.52E-05 | 78 | AmplitudeNose;StrideLengthVariance |
| 1 | rs31705483 | 147311100 | 1.38E+08 | 1.52E+08 | T | C | 0.315 | 6.379594 | 4.17E-07 | 45 | AngularVelocityVariance;AmplitudeNose;StrideLengthVariance |
| 1 | rs33726926 | 158540364 | 1.51E+08 | 1.62E+08 | T | C | 0.415 | 5.042228 | 9.07E-06 | 88 | DistanceTraveled;AngularVelocityVariance;LimbDutyVariance;AmplitudeNoseVariance;StrideLength;StrideLengthVariance;TemporalSymmetryVariance |

FIG. 22 continued

| | | | | | | | | | | | |
|---|---|---|---|---|---|---|---|---|---|---|---|
| 1 | rs33725561 | 158650946 | 1.5E+08 | 1.68E+08 | G | C | 0.883 | 5.836381 | 1.46E-06 | 153 | DistanceTraveled;AngularVelocityVariance;LimbDutyVariance;AmplitudeNoseVariance;StepLength;StrideLength;StrideLengthVariance;TemporalSymmetryVariance |
| 1 | rs31321636 | 159037725 | 1.5E+08 | 1.69E+08 | T | C | 0.639 | 6.942676 | 1.14E-07 | 149 | DistanceTraveled;AngularVelocityVariance;LimbDutyVariance;AmplitudeNoseVariance;StepLength;StrideLength;StrideLengthVariance;TemporalSymmetryVariance |
| 1 | rs30501480 | 170659871 | 1.61E+08 | 1.79E+08 | G | A | 0.602 | 5.114385 | 7.68E-06 | 215 | AngularVelocityVariance;StepLength;StrideLength |
| 1 | rs33834570 | 186942225 | 1.77E+08 | 1.95E+08 | T | C | 0.926 | 4.991526 | 1.02E-05 | 123 | AmplitudeTailBaseVariance;AmplitudeNose;TemporalSymmetryVariance;AmplitudeTailTipVariance |
| 1 | rs32270451 | 187052607 | 1.77E+08 | 1.95E+08 | G | C | 0.186 | 6.480797 | 3.31E-07 | 117 | AmplitudeTailBaseVariance;AmplitudeNose;TemporalSymmetryVariance;AmplitudeTailTipVariance |
| 1 | rs36820042 | 190685044 | 1.87E+08 | 1.93E+08 | T | G | 0.067 | 4.74944 | 1.78E-05 | 46 | AmplitudeNose;TemporalSymmetryVariance;AmplitudeTailTipVariance |
| 2 | rs27079510 | 6333217 | 3685310 | 7861359 | T | G | 0.917 | 6.467348 | 3.41E-07 | 22 | AmplitudeNoseVariance |
| 2 | rs27185290 | 26982969 | 26982969 | 27168536 | G | A | 0.072 | 5.207025 | 6.21E-06 | 8 | StrideLengthVariance |
| 2 | rs27892766 | 58326475 | 57899382 | 59436843 | G | A | 0.107 | 11.13401 | 7.34E-12 | 9 | StrideLengthVariance |
| 2 | rs27961507 | 77031983 | 73227956 | 78347475 | G | A | 0.072 | 4.860409 | 1.38E-05 | 41 | StrideCount;TemporalSymmetry |
| 2 | rs27965461 | 77485353 | 68869532 | 77486737 | G | A | 0.893 | 5.528433 | 2.96E-06 | 80 | StrideCount;TemporalSymmetry |
| 2 | rs27944118 | 77770632 | 71149175 | 78738242 | T | C | 0.807 | 8.292661 | 5.10E-09 | 55 | StrideCount;TemporalSymmetry |
| 2 | rs27975766 | 78606793 | 68643961 | 85510358 | T | G | 0.921 | 4.791204 | 1.62E-05 | 141 | StrideCount;TemporalSymmetry |
| 2 | rs29717768 | 104048908 | 94098587 | 1.14E+08 | T | C | 0.343 | 4.77241 | 1.69E-05 | 124 | StrideCount;DistanceTraveled;AngularVelocityVariance;AmplitudeTailBase;StrideLengthVariance;TemporalSymmetryVariance |
| 2 | rs27414545 | 104693404 | 1E+08 | 1.07E+08 | T | C | 0.165 | 4.745 | 1.80E-05 | 45 | DistanceTraveled;AngularVelocityVariance;AmplitudeTailBase;TemporalSymmetryVariance |
| 2 | rs33709216 | 106061336 | 96089361 | 1.16E+08 | T | C | 0.649 | 6.017514 | 9.60E-07 | 128 | StrideCount;DistanceTraveled;AngularVelocityVariance;AmplitudeTailBase;AmplitudeNose;StrideLengthVariance;TemporalSymmetryVariance |
| 2 | rs27445827 | 106418983 | 99794474 | 1.15E+08 | G | A | 0.735 | 5.850111 | 1.41E-06 | 123 | StrideCount;DistanceTraveled;AngularVelocityVariance;AmplitudeTailBase;AmplitudeNose;StrideLengthVariance;TemporalSymmetryVariance |

FIG. 22 continued

| | | | | | | | | | | | |
|---|---|---|---|---|---|---|---|---|---|---|---|
| 2 | rs28255085 | 111033474 | 1.07E+08 | 1.13E+08 | T | C | 0.085 | 5.587012 | 2.59E-06 | 64 | StrideCount;AmplitudeTailBase;StrideLengthVariance |
| 2 | rs6202263 | 137040750 | 1.35E+08 | 1.39E+08 | T | C | 0.095 | 4.860211 | 1.38E-05 | 12 | StrideLengthVariance |
| 2 | rs27187940 | 140938185 | 1.38E+08 | 1.51E+08 | T | G | 0.225 | 4.910931 | 1.23E-05 | 75 | DistanceTraveled;LimbDutyVariance;AmplitudeNoseVariance;StrideLengthVariance;TemporalSymmetryVariance |
| 2 | rs27242639 | 146110924 | 1.44E+08 | 1.55E+08 | T | C | 0.07 | 8.687101 | 2.06E-09 | 149 | LimbDutyVariance;AmplitudeNoseVariance;StrideLengthVariance;TemporalSymmetryVariance |
| 2 | rs27320603 | 159114986 | 1.51E+08 | 1.68E+08 | G | A | 0.902 | 5.094685 | 8.04E-06 | 297 | DistanceTraveled;StepWidth;StrideLength |
| 2 | rs27332588 | 161955109 | 1.53E+08 | 1.66E+08 | T | C | 0.501 | 4.978986 | 1.05E-05 | 217 | DistanceTraveled;StepWidth;StrideLength |
| 2 | rs27312190 | 169475865 | 1.6E+08 | 1.75E+08 | T | C | 0.223 | 7.037963 | 9.16E-08 | 170 | DistanceTraveled;AmplitudeNose;StrideLength |
| 3 | rs36695668 | 26296954 | 18369543 | 35702607 | T | C | 0.386 | 5.533078 | 2.93E-06 | 62 | AngularVelocityVariance;StrideLength |
| 3 | rs3158608 | 37453870 | 27620836 | 42452233 | T | C | 0.529 | 6.689076 | 2.05E-07 | 79 | AmplitudeNose;StepWidthVariance |
| 3 | rs30712905 | 57233738 | 47534522 | 66041036 | G | C | 0.925 | 8.47675 | 3.34E-09 | 90 | DistanceTraveled;AngularVelocityVariance;LimbDuty;AmplitudeNoseVariance |
| 3 | rs30105433 | 59312392 | 49610012 | 66345163 | T | C | 0.474 | 5.153996 | 7.01E-06 | 92 | DistanceTraveled;AngularVelocityVariance;LimbDuty;AmplitudeNoseVariance;StrideLength |
| 3 | rs30887443 | 63722028 | 58800671 | 73176938 | G | A | 0.11 | 5.56186 | 2.74E-06 | 67 | DistanceTraveled;AngularVelocityVariance;LimbDuty;StrideLength |
| 3 | rs6408988 | 65692879 | 61402717 | 66292987 | G | C | 0.285 | 4.899876 | 1.26E-05 | 23 | AngularVelocityVariance;LimbDuty;StrideLength |
| 3 | rs48930698 | 66147399 | 56740619 | 75383088 | T | C | 0.204 | 5.643358 | 2.27E-06 | 84 | DistanceTraveled;AngularVelocityVariance;LimbDuty;AmplitudeNoseVariance;StrideLength |
| 3 | rs31423436 | 73049857 | 63277489 | 82035672 | G | A | 0.567 | 6.483616 | 3.28E-07 | 70 | AngularVelocityVariance;LimbDuty;AmplitudeNose;StrideLength;TemporalSymmetry |
| 3 | rs31257083 | 79697241 | 69739991 | 87724618 | T | G | 0.821 | 4.898506 | 1.26E-05 | 70 | AmplitudeTailBaseVariance;LimbDuty;AmplitudeNose;AmplitudeNoseVariance;TemporalSymmetry |
| 3 | rs30301060 | 83445028 | 75222914 | 89332695 | T | C | 0.223 | 11.67439 | 2.12E-12 | 130 | AmplitudeTailBaseVariance;AmplitudeNose;AmplitudeNoseVariance;TemporalSymmetry |

FIG. 22 continued

| | | | | | | | | | | | |
|---|---|---|---|---|---|---|---|---|---|---|---|
| 3 | rs37561283 | 84614028 | 76613637 | 92944599 | C | A | 0.149 | 4.873164 | 1.34E-05 | 223 | AmplitudeTailBaseVariance;AmplitudeNose;AmplitudeNoseVariance;TemporalSymmetry |
| 3 | rs33229423 | 99190469 | 92733413 | 1.07E+08 | T | A | 0.107 | 4.724254 | 1.89E-05 | 245 | AngularVelocityVariance;StepWidthVariance;AmplitudeTailTipVariance |
| 3 | rs33307059 | 99930271 | 93130513 | 1.07E+08 | T | A | 0.571 | 6.240524 | 5.75E-07 | 225 | AngularVelocityVariance;StepWidthVariance;AmplitudeTailTipVariance |
| 3 | rs29653704 | 108803382 | 99807707 | 1.14E+08 | C | A | 0.908 | 5.150973 | 7.06E-06 | 142 | AngularVelocityVariance;TemporalSymmetryVariance;AmplitudeTailTipVariance |
| 3 | rs36259450 | 118519497 | 1.16E+08 | 1.28E+08 | C | A | 0.213 | 6.069156 | 8.53E-07 | 57 | StepWidthVariance;TemporalSymmetryVariance |
| 3 | rs36246842 | 128199769 | 1.26E+08 | 1.28E+08 | T | C | 0.124 | 5.361087 | 4.35E-06 | 10 | StepWidthVariance |
| 3 | rs36549927 | 131244658 | 1.22E+08 | 1.39E+08 | T | C | 0.394 | 4.843695 | 1.43E-05 | 97 | StepLength;StepWidthVariance |
| 3 | rs31069045 | 142766584 | 1.38E+08 | 1.47E+08 | G | C | 0.753 | 5.722262 | 1.90E-06 | 56 | AmplitudeNose;StepWidthVariance;TemporalSymmetryVariance |
| 3 | rs49271520 | 145484561 | 1.36E+08 | 1.48E+08 | C | A | 0.87 | 4.94585 | 1.13E-05 | 70 | AmplitudeNose;StepWidthVariance;TemporalSymmetry;TemporalSymmetryVariance |
| 3 | rs31381691 | 147275378 | 1.38E+08 | 1.57E+08 | T | C | 0.48 | 5.084303 | 8.24E-06 | 80 | LimbDuty;AmplitudeNose;StepWidthVariance;StrideLength;TemporalSymmetry;TemporalSymmetryVariance |
| 3 | rs30214161 | 147380197 | 1.39E+08 | 1.57E+08 | G | A | 0.204 | 5.780175 | 1.66E-06 | 78 | LimbDuty;AmplitudeNose;StepWidthVariance;StrideLength;TemporalSymmetry;TemporalSymmetryVariance |
| 4 | rs32586544 | 17975545 | 8295841 | 27872190 | T | C | 0.204 | 5.717293 | 1.92E-06 | 65 | AmplitudeNose;StepWidth |
| 4 | rs27881605 | 43368723 | 34933100 | 51210522 | T | G | 0.907 | 7.562662 | 2.74E-08 | 162 | DistanceTraveled;AmplitudeTailBase;StepWidth;StepWidthVariance;StrideLength;TemporalSymmetry |
| 4 | rs27826214 | 44017961 | 34021585 | 52336018 | T | C | 0.559 | 4.721785 | 1.90E-05 | 173 | DistanceTraveled;AmplitudeTailBase;StepWidth;StepWidthVariance;StrideLength;TemporalSymmetry |
| 4 | rs27878602 | 44046202 | 40490148 | 47701876 | T | A | 0.851 | 6.231243 | 5.87E-07 | 132 | DistanceTraveled;AmplitudeTailBase;StepWidth;StepWidthVariance;TemporalSymmetry |
| 4 | rs27857217 | 46354166 | 45489432 | 54118427 | C | A | 0.61 | 4.86259 | 1.37E-05 | 59 | StrideLength;TemporalSymmetry |
| 4 | rs27810611 | 51035548 | 43310591 | 56661874 | C | A | 0.277 | 4.749104 | 1.78E-05 | 109 | DistanceTraveled;AmplitudeTailBase;StepWidth;StepWidthVariance;StrideLength;TemporalSymmetry |
| 4 | rs32187175 | 59423324 | 50647592 | 63289996 | G | A | 0.777 | 5.267349 | 5.40E-06 | 93 | AngularVelocityVariance;AmplitudeNose;AmplitudeNoseVariance;StrideLength |

FIG. 22 continued

| | | | | | | | | | | | |
|---|---|---|---|---|---|---|---|---|---|---|---|
| 4 | rs27886817 | 66472052 | 59486030 | 76456186 | G | A | 0.858 | 7.099833 | 7.95E-08 | 85 | DistanceTraveled;AngularVelocityVariance;StrideLength;TemporalSymmetry |
| 4 | rs27840151 | 72136330 | 67012269 | 81999037 | C | A | 0.232 | 7.042403 | 9.07E-08 | 25 | TemporalSymmetry |
| 4 | rs28082582 | 96069209 | 86176671 | 1.01E+08 | T | A | 0.243 | 5.292902 | 5.09E-06 | 95 | DistanceTraveled;StepWidthVariance;StrideLength;StrideLengthVariance;TemporalSymmetry;AmplitudeTailTip |
| 4 | rs28075635 | 99187163 | 89350421 | 1.07E+08 | G | A | 0.72 | 4.987725 | 1.03E-05 | 81 | DistanceTraveled;AmplitudeTailBaseVariance;AmplitudeNoseVariance;StepWidthVariance;StrideLength;StrideLengthVariance;TemporalSymmetry;AmplitudeTailTip |
| 4 | rs28177822 | 100961889 | 91402378 | 1.06E+08 | T | C | 0.619 | 5.637602 | 2.30E-06 | 71 | DistanceTraveled;AmplitudeTailBaseVariance;AmplitudeNoseVariance;StepWidthVariance;StrideLength;StrideLengthVariance;TemporalSymmetry;AmplitudeTailTip |
| 4 | rs28202448 | 101088871 | 93679104 | 1.11E+08 | G | A | 0.099 | 5.813965 | 1.53E-06 | 129 | DistanceTraveled;AmplitudeTailBaseVariance;AmplitudeNoseVariance;StepWidthVariance;StrideLength;StrideLengthVariance;TemporalSymmetry;AmplitudeTailTip |
| 4 | rs28187910 | 105046298 | 95621654 | 1.12E+08 | T | C | 0.103 | 5.90604 | 1.24E-06 | 122 | DistanceTraveled;AmplitudeTailBaseVariance;AmplitudeNoseVariance;StepWidthVariance;StrideLength;StrideLengthVariance;TemporalSymmetry;AmplitudeTailTip |
| 4 | rs28132247 | 107746835 | 98255368 | 1.12E+08 | G | A | 0.935 | 6.240249 | 5.75E-07 | 110 | DistanceTraveled;AmplitudeTailBaseVariance;AmplitudeNoseVariance;StepWidthVariance;StrideLength;StrideLengthVariance;TemporalSymmetry;AmplitudeTailTip |
| 4 | rs48203033 | 116081154 | 1.06E+08 | 1.26E+08 | T | C | 0.11 | 5.277351 | 5.28E-06 | 257 | StepLengthVariance;StepWidthVariance;StrideLengthVariance;TemporalSymmetry;AmplitudeTailTipVariance |
| 4 | rs27511170 | 116166578 | 1.07E+08 | 1.26E+08 | T | A | 0.118 | 9.108077 | 7.80E-10 | 234 | StepLengthVariance;StepWidthVariance;StrideLengthVariance;TemporalSymmetry;AmplitudeTailTipVariance |
| 4 | rs27528208 | 118933871 | 1.14E+08 | 1.29E+08 | G | A | 0.512 | 5.021917 | 9.51E-06 | 218 | StepLengthVariance;StepWidthVariance;StrideLengthVariance;TemporalSymmetry;AmplitudeTailTipVariance |

FIG. 22 continued

| | | | | | | | | | | | |
|---|---|---|---|---|---|---|---|---|---|---|---|
| 4 | rs27516423 | 120624946 | 1.12E+08 | 1.3E+08 | T | C | 0.492 | 4.813544 | 1.54E-05 | 270 | StepLengthVariance;StepWidthVariance;StrideLengthVariance;TemporalSymmetry;AmplitudeTailTipVariance |
| 4 | rs27586672 | 124242333 | 1.18E+08 | 1.34E+08 | G | A | 0.718 | 5.121385 | 7.56E-06 | 251 | StepLengthVariance;StrideLengthVariance;TemporalSymmetry;AmplitudeTailTipVariance |
| 4 | rs27537862 | 131827578 | 1.24E+08 | 1.4E+08 | G | A | 0.1 | 5.059349 | 8.72E-06 | 279 | DistanceTraveled;AngularVelocityVariance;StepWidthVariance;StrideLength;StrideLengthVariance;AmplitudeTailTipVariance |
| 4 | rs27580925 | 135547923 | 1.3E+08 | 1.45E+08 | G | A | 0.727 | 6.75796 | 1.75E-07 | 268 | DistanceTraveled;AngularVelocityVariance;LimbDutyVariance;StepWidthVariance;StrideLength;StrideLengthVariance |
| 4 | rs27607875 | 142191070 | 1.38E+08 | 1.52E+08 | T | A | 0.205 | 5.008402 | 9.81E-06 | 193 | DistanceTraveled;AngularVelocityVariance;LimbDutyVariance;StrideLength;StrideLengthVariance |
| 4 | rs27641324 | 143041959 | 1.33E+08 | 1.51E+08 | T | C | 0.653 | 4.952596 | 1.12E-05 | 302 | DistanceTraveled;AngularVelocityVariance;LimbDutyVariance;StepWidthVariance;StrideLength;StrideLengthVariance |
| 4 | rs32227624 | 152953965 | 1.5E+08 | 1.56E+08 | T | G | 0.253 | 5.295755 | 5.06E-06 | 71 | AmplitudeTailBase;LimbDuty;AmplitudeNose |
| 4 | rs33115456 | 154871382 | 1.45E+08 | 1.56E+08 | G | A | 0.204 | 5.717293 | 1.92E-06 | 160 | AmplitudeTailBase;LimbDuty;AmplitudeNose |
| 5 | rs36909022 | 9993554 | 5025341 | 12228774 | C | A | 0.895 | 6.029847 | 9.34E-07 | 38 | StrideLengthVariance |
| 5 | rs31578008 | 12039819 | 3941195 | 12819929 | G | A | 0.935 | 6.205564 | 6.23E-07 | 43 | StrideLengthVariance;TemporalSymmetry |
| 5 | rs31539350 | 12395368 | 3259901 | 22332054 | T | A | 0.638 | 4.794973 | 1.60E-05 | 95 | AngularVelocityVariance;StrideLengthVariance;TemporalSymmetry;AmplitudeTailTipVariance |
| 5 | rs33844542 | 14854805 | 4855780 | 24481597 | T | G | 0.785 | 4.951006 | 1.12E-05 | 100 | AngularVelocityVariance;StepLengthVariance;StepWidthVariance;StrideLengthVariance;TemporalSymmetry;AmplitudeTailTipVariance |
| 5 | rs33425558 | 22782827 | 12962819 | 32299567 | T | C | 0.271 | 5.84431 | 1.43E-06 | 160 | AngularVelocityVariance;StepLengthVariance;StepWidthVariance;AmplitudeTailTipVariance |
| 5 | rs32019889 | 24438888 | 24367676 | 24991505 | G | C | 0.912 | 15.12898 | 7.43E-16 | 20 | StepWidthVariance |
| 5 | rs32536983 | 35121467 | 25694990 | 37558726 | G | A | 0.606 | 5.508503 | 3.10E-06 | 154 | TemporalSymmetryVariance |

FIG. 22 continued

| | | | | | | | | | | |
|---|---|---|---|---|---|---|---|---|---|---|
| 5 | rs46454443 | 39666314 | 30917520 | 47347901 | T | G | 0.195 | 7.303708 | 4.97E-08 | 141 | AmplitudeTailBaseVariance;AmplitudeNose;AmplitudeNoseVariance;TemporalSymmetryVariance |
| 5 | rs37184288 | 44532644 | 43786841 | 51770712 | T | C | 0.102 | 4.940147 | 1.15E-05 | 20 | AmplitudeTailBaseVariance;AmplitudeNoseVariance;TemporalSymmetryVariance |
| 5 | rs32932478 | 53425802 | 48452925 | 53552183 | T | C | 0.088 | 15.12898 | 7.43E-16 | 15 | StepWidthVariance;TemporalSymmetryVariance |
| 5 | rs33043490 | 65921872 | 57410022 | 75596917 | T | C | 0.301 | 6.646367 | 2.26E-07 | 81 | StrideCount;AmplitudeTailBaseVariance;LimbDutyVariance;AmplitudeNose;AmplitudeNoseVariance;StrideLengthVariance;TemporalSymmetryVariance |
| 5 | rs29730734 | 66921126 | 63998196 | 76170477 | G | A | 0.777 | 11.63514 | 2.32E-12 | 76 | StrideCount;AmplitudeTailBaseVariance;LimbDutyVariance;AmplitudeNose;AmplitudeNoseVariance;StrideLengthVariance;TemporalSymmetryVariance |
| 5 | rs29683086 | 89103566 | 82396357 | 98037482 | T | A | 0.464 | 4.886749 | 1.30E-05 | 136 | AmplitudeNose |
| 5 | rs31728918 | 91048297 | 82384660 | 97847246 | T | G | 0.288 | 5.437866 | 3.65E-06 | 135 | AmplitudeNose |
| 5 | rs31881900 | 97371496 | 89520851 | 1.07E+08 | G | A | 0.814 | 6.491399 | 3.23E-07 | 143 | AmplitudeNose |
| 5 | rs52557344 | 112913426 | 1.06E+08 | 1.17E+08 | T | C | 0.129 | 5.09451 | 8.04E-06 | 159 | AmplitudeNose;StepWidthVariance;StrideLength |
| 5 | rs33614208 | 114398209 | 1.04E+08 | 1.24E+08 | G | A | 0.422 | 4.938677 | 1.15E-05 | 284 | AmplitudeNose;StepWidthVariance;StrideLength;TemporalSymmetry;TemporalSymmetryVariance |
| 5 | rs49685014 | 117625350 | 1.11E+08 | 1.26E+08 | T | C | 0.105 | 4.940414 | 1.15E-05 | 227 | StepWidthVariance;StrideLength;TemporalSymmetry;TemporalSymmetryVariance |
| 5 | rs32148753 | 119913668 | 1.12E+08 | 1.28E+08 | T | C | 0.41 | 5.026983 | 9.40E-06 | 219 | StepWidthVariance;StrideLength;TemporalSymmetry;TemporalSymmetryVariance |
| 5 | rs33586133 | 129470997 | 1.21E+08 | 1.39E+08 | G | A | 0.869 | 4.978536 | 1.05E-05 | 256 | StepLengthVariance;StepWidthVariance |
| 5 | rs6180535 | 137493677 | 1.34E+08 | 1.47E+08 | G | A | 0.146 | 6.847176 | 1.42E-07 | 251 | AmplitudeNose;StepWidthVariance |
| 5 | rs29731996 | 139415912 | 1.3E+08 | 1.47E+08 | G | A | 0.796 | 5.724744 | 1.88E-06 | 264 | AmplitudeNose;StepWidthVariance |
| 6 | rs30327190 | 6355455 | 4027803 | 14951805 | T | G | 0.562 | 5.09649 | 8.01E-06 | 39 | DistanceTraveled |
| 6 | rs30809119 | 15563450 | 8040411 | 19822216 | T | G | 0.298 | 5.255322 | 5.55E-06 | 33 | StepLength |
| 6 | rs30468068 | 32302364 | 32122366 | 38854827 | G | A | 0.785 | 5.231237 | 5.87E-06 | 42 | StrideCount;LimbDutyVariance;AmplitudeNoseVariance;StrideLengthVariance;AmplitudeTailTipVariance |

FIG. 22 continued

| | | | | | | | | | | | |
|---|---|---|---|---|---|---|---|---|---|---|---|
| 6 | rs46410157 | 33163697 | 25589431 | 43155315 | G | A | 0.084 | 7.651605 | 2.23E-08 | 171 | StrideCount;LimbDutyVariance;AmplitudeNoseVariance;StrideLengthVariance;AmplitudeTailTipVariance |
| 6 | rs30930477 | 38027132 | 34488084 | 38924622 | G | A | 0.489 | 4.820368 | 1.51E-05 | 34 | StrideCount |
| 6 | rs29992121 | 53719656 | 51005634 | 54257834 | G | A | 0.85 | 9.12918 | 7.43E-10 | 25 | DistanceTraveled;AngularVelocityVariance;AmplitudeNose;StrideLength |
| 6 | rs29999456 | 53950680 | 44021906 | 63834706 | G | A | 0.427 | 4.844103 | 1.43E-05 | 144 | DistanceTraveled;AngularVelocityVariance;AmplitudeNose;StepWidthVariance;StrideLength |
| 6 | rs30216441 | 56191607 | 47087392 | 63760372 | C | A | 0.149 | 5.946989 | 1.13E-06 | 144 | DistanceTraveled;AngularVelocityVariance;AmplitudeNose;StepWidthVariance;StrideLength |
| 6 | rs37871513 | 69887863 | 68334794 | 77530708 | T | G | 0.817 | 5.214309 | 6.11E-06 | 44 | StrideCount;DistanceTraveled;AngularVelocityVariance;StepWidthVariance;StrideLength |
| 6 | rs36592157 | 73152495 | 66930816 | 76144864 | G | A | 0.876 | 7.106168 | 7.83E-08 | 47 | StrideCount;DistanceTraveled;StepWidthVariance;StrideLength |
| 6 | rs37185505 | 78231180 | 71283627 | 87077063 | T | C | 0.506 | 5.850454 | 1.41E-06 | 131 | DistanceTraveled;AngularVelocityVariance;LimbDuty;StepLength;StepWidthVariance;StrideLength;TemporalSymmetryVariance |
| 6 | rs49418546 | 80452675 | 77229589 | 86950310 | G | C | 0.89 | 8.009845 | 9.78E-09 | 93 | DistanceTraveled;AngularVelocityVariance;LimbDuty;StepLength;StepWidthVariance;StrideLength;TemporalSymmetryVariance |
| 6 | rs36657240 | 100345203 | 91439030 | 1.03E+08 | G | A | 0.89 | 4.74245 | 1.81E-05 | 45 | TemporalSymmetry |
| 6 | rs30864295 | 105437378 | 1.03E+08 | 1.14E+08 | G | A | 0.16 | 5.031468 | 9.30E-06 | 48 | DistanceTraveled;AngularVelocityVariance;AmplitudeTailBaseVariance;LimbDuty;AmplitudeNoseVariance;StrideLength |
| 6 | rs29919381 | 106617049 | 96827512 | 1.14E+08 | G | A | 0.303 | 7.308262 | 4.92E-08 | 68 | DistanceTraveled;AngularVelocityVariance;AmplitudeTailBaseVariance;LimbDuty;AmplitudeNoseVariance;StrideLength;TemporalSymmetry |
| 6 | rs36334404 | 106904181 | 1.06E+08 | 1.14E+08 | G | A | 0.088 | 5.212077 | 6.14E-06 | 47 | AngularVelocityVariance;AmplitudeTailBaseVariance;LimbDuty;AmplitudeNoseVariance |
| 6 | rs39425773 | 108312483 | 99818059 | 1.17E+08 | T | C | 0.388 | 4.952011 | 1.12E-05 | 92 | DistanceTraveled;AngularVelocityVariance;AmplitudeTailBaseVariance;LimbDuty;AmplitudeNoseVariance;StrideLength;TemporalSymmetry |

FIG. 22 continued

| | | | | | | | | | | | |
|---|---|---|---|---|---|---|---|---|---|---|---|
| 6 | rs36522368 | 108793140 | 1.01E+08 | 1.16E+08 | T | C | 0.868 | 6.183053 | 6.56E-07 | 76 | DistanceTraveled;AngularVelocityVariance;AmplitudeTailBaseVariance;LimbDuty;AmplitudeNoseVariance;StrideLength |
| 6 | rs31649445 | 119128870 | 1.12E+08 | 1.29E+08 | T | C | 0.936 | 9.707806 | 1.96E-10 | 240 | LimbDutyVariance;AmplitudeNoseVariance;StrideLengthVariance;TemporalSymmetryVariance |
| 6 | rs36959176 | 135519828 | 1.26E+08 | 1.45E+08 | T | C | 0.263 | 6.648693 | 2.25E-07 | 192 | StrideCount;DistanceTraveled;AngularVelocityVariance;AmplitudeNoseVariance;StrideLength;StrideLengthVariance;AmplitudeTailTipVariance |
| 6 | rs30648467 | 137079191 | 1.27E+08 | 1.46E+08 | T | A | 0.736 | 5.313325 | 4.86E-06 | 180 | StrideCount;DistanceTraveled;AngularVelocityVariance;AmplitudeNoseVariance;StrideLength;StrideLengthVariance;AmplitudeTailTipVariance |
| 6 | rs36834282 | 141208623 | 1.31E+08 | 1.48E+08 | T | C | 0.145 | 7.224336 | 5.97E-08 | 138 | StrideCount;DistanceTraveled;AngularVelocityVariance;LimbDutyVariance;AmplitudeNoseVariance;StepWidthVariance;StrideLength;StrideLengthVariance;TemporalSymmetryVariance;AmplitudeTailTipVariance |
| 6 | rs37815873 | 146227691 | 1.44E+08 | 1.48E+08 | G | A | 0.15 | 6.526383 | 2.98E-07 | 27 | LimbDutyVariance;AmplitudeNoseVariance;StepWidthVariance;StrideLengthVariance;TemporalSymmetryVariance |
| 6 | rs30276565 | 147741062 | 1.44E+08 | 1.49E+08 | C | A | 0.819 | 5.033768 | 9.25E-06 | 34 | LimbDutyVariance;AmplitudeNoseVariance;StepWidthVariance;StrideLengthVariance;TemporalSymmetryVariance;AmplitudeTailTipVariance |
| 7 | rs31511215 | 4373428 | 3939315 | 12832654 | C | A | 0.223 | 6.337867 | 4.59E-07 | 160 | DistanceTraveled;AngularVelocityVariance;LimbDuty;AmplitudeNoseVariance;StepLength;StepLengthVariance;StrideLength;StrideLengthVariance |
| 7 | rs47049967 | 4876005 | 3696957 | 4876005 | T | C | 0.366 | 7.286694 | 5.17E-08 | 38 | DistanceTraveled;AngularVelocityVariance;LimbDuty;AmplitudeNoseVariance;StepLength;StrideLength |
| 7 | rs49434467 | 6456328 | 4163600 | 10663196 | G | C | 0.148 | 5.674696 | 2.11E-06 | 124 | DistanceTraveled;AngularVelocityVariance;LimbDuty;AmplitudeNoseVariance;StepLength;StepLengthVariance;StrideLength;StrideLengthVariance |

FIG. 22 continued

| | | | | | | | | | | | |
|---|---|---|---|---|---|---|---|---|---|---|---|
| 7 | rs32042649 | 13023110 | 3619131 | 20046745 | G | C | 0.412 | 5.245216 | 5.69E-06 | 334 | DistanceTraveled;AngularVelocityVariance;LimbDuty;AmplitudeNoseVariance;StepLength;StepLengthVariance;StrideLength;StrideLengthVariance |
| 7 | rs47581453 | 13433926 | 11991442 | 23386383 | T | G | 0.17 | 5.019771 | 9.55E-06 | 263 | DistanceTraveled;AngularVelocityVariance;StrideLength |
| 7 | rs38410017 | 27047092 | 26463740 | 27959696 | G | A | 0.929 | 5.914171 | 1.22E-06 | 41 | AmplitudeNoseVariance |
| 7 | rs52139177 | 35074244 | 34920437 | 44756420 | T | C | 0.901 | 5.045881 | 9.00E-06 | 125 | StrideCount;DistanceTraveled;AngularVelocityVariance;AmplitudeTailBaseVariance;LimbDuty;LimbDutyVariance;StepLength;StepWidth;StrideLength;StrideLengthVariance;TemporalSymmetry;TemporalSymmetryVariance |
| 7 | rs32072976 | 35200730 | 27130966 | 44258214 | G | A | 0.908 | 5.285578 | 5.18E-06 | 309 | StrideCount;DistanceTraveled;AngularVelocityVariance;AmplitudeTailBaseVariance;LimbDuty;LimbDutyVariance;StepLength;StepWidth;StrideLength;StrideLengthVariance;TemporalSymmetry;TemporalSymmetryVariance |
| 7 | rs36877047 | 35561631 | 31036779 | 43808029 | G | C | 0.432 | 9.08968 | 8.13E-10 | 127 | StrideCount;DistanceTraveled;AngularVelocityVariance;AmplitudeTailBaseVariance;LimbDuty;LimbDutyVariance;StepLength;StepWidth;StrideLength;StrideLengthVariance;TemporalSymmetry;TemporalSymmetryVariance |
| 7 | rs31849337 | 36833259 | 27251194 | 44560350 | G | A | 0.572 | 9.746673 | 1.79E-10 | 314 | StrideCount;DistanceTraveled;AngularVelocityVariance;AmplitudeTailBaseVariance;LimbDuty;LimbDutyVariance;StepLength;StepWidth;StrideLength;StrideLengthVariance;TemporalSymmetry;TemporalSymmetryVariance |
| 7 | rs36473595 | 39541616 | 35483011 | 40404169 | G | A | 0.37 | 6.824315 | 1.50E-07 | 17 | StrideCount;DistanceTraveled;AngularVelocityVariance;AmplitudeTailBaseVariance;LimbDuty;StepLength;StepWidth;StrideLength |

FIG. 22 continued

| | | | | | | | | | | | |
|---|---|---|---|---|---|---|---|---|---|---|---|
| 7 | rs32738808 | 41981838 | 37130555 | 50052077 | T | C | 0.121 | 6.863313 | 1.37E-07 | 238 | StrideCount;DistanceTraveled;AngularVelocityVariance;LimbDutyVariance;StepLength;StepWidth;StrideLength;TemporalSymmetryVariance |
| 7 | rs32867979 | 49155393 | 43977197 | 57676522 | G | A | 0.262 | 4.848833 | 1.42E-05 | 186 | AmplitudeTailBaseVariance;AmplitudeNose;AmplitudeNoseVariance;StepWidth |
| 7 | rs32974867 | 56133958 | 50743458 | 65516186 | G | C | 0.24 | 5.964858 | 1.08E-06 | 41 | DistanceTraveled;AmplitudeTailBaseVariance;AmplitudeNose;AmplitudeNoseVariance;StepWidth |
| 7 | rs38572436 | 67552733 | 57560068 | 77341018 | T | C | 0.186 | 6.355027 | 4.42E-07 | 58 | StrideCount;DistanceTraveled;AngularVelocityVariance;AmplitudeTailBase;AmplitudeTailBaseVariance;LimbDutyVariance;AmplitudeNose;AmplitudeNoseVariance;StepLength;StepLengthVariance;StepWidth;StepWidthVariance;StrideLength;StrideLengthVariance;TemporalSymmetryVariance;AmplitudeTailTipVariance |
| 7 | rs32055354 | 67729085 | 63465020 | 69826345 | G | A | 0.758 | 6.050615 | 8.90E-07 | 35 | StrideCount;DistanceTraveled;AmplitudeTailBaseVariance;AmplitudeNoseVariance;StepLength;StepWidth;StrideLength |
| 7 | rs32520164 | 67886841 | 57900136 | 75649370 | G | A | 0.105 | 5.187633 | 6.49E-06 | 55 | StrideCount;DistanceTraveled;AngularVelocityVariance;AmplitudeTailBase;AmplitudeTailBaseVariance;LimbDutyVariance;AmplitudeNose;AmplitudeNoseVariance;StepLength;StepLengthVariance;StepWidth;StepWidthVariance;StrideLength;StrideLengthVariance;TemporalSymmetryVariance;AmplitudeTailTipVariance |
| 7 | rs32340200 | 68554817 | 60909188 | 78162338 | T | G | 0.777 | 12.06774 | 8.56E-13 | 52 | StrideCount;DistanceTraveled;AngularVelocityVariance;AmplitudeTailBase;AmplitudeTailBaseVariance;LimbDutyVariance;AmplitudeNose;AmplitudeNoseVariance;StepLength;StepLengthVariance;StepWidth;StepWidthVariance;StrideLength;StrideLengthVariance;TemporalSymmetryVariance;AmplitudeTailTipVariance |

FIG. 22 continued

| | | | | | | | | | | | |
|---|---|---|---|---|---|---|---|---|---|---|---|
| 7 | rs47162257 | 72404117 | 71342396 | 78779631 | T | C | 0.099 | 5.839651 | 1.45E-06 | 12 | StrideCount;DistanceTraveled;AngularVelocityVariance;AmplitudeTailBase;AmplitudeTailBaseVariance;LimbDutyVariance;AmplitudeNose;AmplitudeNoseVariance;StepLength;StepLengthVariance;StepWidth;StepWidthVariance;StrideLength;StrideLengthVariance;TemporalSymmetryVariance;AmplitudeTailTipVariance |
| 7 | rs32249219 | 72709703 | 64819611 | 79116494 | G | A | 0.639 | 8.509935 | 3.09E-09 | 45 | StrideCount;DistanceTraveled;AngularVelocityVariance;AmplitudeTailBase;AmplitudeTailBaseVariance;LimbDutyVariance;AmplitudeNose;AmplitudeNoseVariance;StepLength;StepLengthVariance;StepWidth;StepWidthVariance;StrideLength;StrideLengthVariance;TemporalSymmetryVariance;AmplitudeTailTipVariance |
| 7 | rs36445884 | 73829623 | 66250564 | 78766364 | G | A | 0.906 | 13.48823 | 3.25E-14 | 28 | StrideCount;DistanceTraveled;AngularVelocityVariance;AmplitudeTailBase;AmplitudeTailBaseVariance;LimbDutyVariance;AmplitudeNose;AmplitudeNoseVariance;StepLength;StepLengthVariance;StepWidth;StepWidthVariance;StrideLength;StrideLengthVariance;TemporalSymmetryVariance;AmplitudeTailTipVariance |
| 7 | rs31509282 | 78936559 | 78724253 | 88524775 | T | A | 0.777 | 12.06774 | 8.56E-13 | 120 | DistanceTraveled;AngularVelocityVariance;AmplitudeTailBaseVariance;LimbDutyVariance;AmplitudeNose;AmplitudeNoseVariance;StepWidth;StrideLength;StrideLengthVariance |
| 7 | rs33256461 | 84068039 | 74069743 | 93786180 | G | A | 0.707 | 5.039056 | 9.14E-06 | 147 | StrideCount;DistanceTraveled;AngularVelocityVariance;AmplitudeTailBase;AmplitudeTailBaseVariance;LimbDutyVariance;AmplitudeNose;AmplitudeNoseVariance;StepLengthVariance;StepWidth;StrideLength;StrideLengthVariance;TemporalSymmetryVariance |

FIG. 22 continued

| | | | | | | | | | | | |
|---|---|---|---|---|---|---|---|---|---|---|---|
| 7 | rs33253630 | 84105204 | 74987821 | 84162665 | C | A | 0.163 | 5.310705 | 4.89E-06 | 81 | AmplitudeTailBaseVariance;LimbDutyVariance;AmplitudeNose;AmplitudeNoseVariance;StepLengthVariance;StepWidth;StrideLength;StrideLengthVariance;TemporalSymmetryVariance |
| 7 | rs31854583 | 87432027 | 77622079 | 97423892 | T | G | 0.503 | 14.12035 | 7.58E-15 | 150 | StrideCount;DistanceTraveled;AngularVelocityVariance;AmplitudeTailBase;AmplitudeTailBaseVariance;LimbDutyVariance;AmplitudeNose;AmplitudeNoseVariance;StepWidth;StrideLength;StrideLengthVariance |
| 7 | rs47742264 | 90409199 | 90141888 | 92167408 | T | G | 0.854 | 5.565956 | 2.72E-06 | 8 | AmplitudeNose;AmplitudeNoseVariance;StepWidth |
| 7 | rs31395954 | 94751891 | 94074053 | 1.04E+08 | G | A | 0.602 | 4.847152 | 1.42E-05 | 211 | StrideCount;AmplitudeTailBaseVariance;AmplitudeNose;AmplitudeNoseVariance;StrideLengthVariance |
| 7 | rs31677255 | 98391621 | 89372972 | 1.07E+08 | T | C | 0.75 | 5.964858 | 1.08E-06 | 321 | StrideCount;DistanceTraveled;AmplitudeTailBaseVariance;AmplitudeNose;AmplitudeNoseVariance;StepWidth;StrideLength;StrideLengthVariance;TemporalSymmetryVariance |
| 7 | rs31996945 | 105471335 | 1.03E+08 | 1.15E+08 | T | G | 0.131 | 4.821451 | 1.51E-05 | 282 | StrideLength;TemporalSymmetryVariance |
| 7 | rs31998083 | 105519769 | 1.02E+08 | 1.1E+08 | G | A | 0.88 | 4.957132 | 1.10E-05 | 269 | StrideLength;TemporalSymmetryVariance |
| 7 | rs13466595 | 113566492 | 1.13E+08 | 1.2E+08 | T | C | 0.684 | 5.176842 | 6.66E-06 | 56 | StepLengthVariance;StrideLength |
| 7 | rs39291881 | 116881664 | 1.07E+08 | 1.26E+08 | G | A | 0.879 | 4.798784 | 1.59E-05 | 182 | StrideCount;DistanceTraveled;StepLengthVariance;StepWidthVariance;StrideLength |
| 7 | rs32921853 | 124914136 | 1.15E+08 | 1.29E+08 | G | C | 0.605 | 6.971496 | 1.07E-07 | 197 | StrideCount;DistanceTraveled;StepLengthVariance;StepWidthVariance;StrideLength |
| 7 | rs32198638 | 128831512 | 1.22E+08 | 1.37E+08 | T | G | 0.163 | 5.072018 | 8.47E-06 | 190 | StrideCount;DistanceTraveled;StepLength;StepLengthVariance;StepWidthVariance;StrideLength |
| 7 | rs31420315 | 134176064 | 1.33E+08 | 1.44E+08 | G | A | 0.537 | 9.685423 | 2.06E-10 | 179 | StepLength |
| 8 | rs48674180 | 17978315 | 14473669 | 27916056 | C | A | 0.096 | 4.95035 | 1.12E-05 | 144 | AmplitudeNose;StepWidthVariance |
| 8 | rs33353389 | 19026730 | 14494594 | 26353267 | T | C | 0.204 | 5.789807 | 1.62E-06 | 130 | AmplitudeNose;StepWidthVariance |
| 8 | rs50145783 | 36362946 | 26382741 | 46241864 | G | A | 0.195 | 7.389349 | 4.08E-08 | 93 | AmplitudeTailBaseVariance;AmplitudeNose |
| 8 | rs31171119 | 50288961 | 43403811 | 57199887 | G | A | 0.918 | 4.967463 | 1.08E-05 | 52 | AmplitudeTailBaseVariance |

FIG. 22 continued

| | | | | | | | | | | | |
|---|---|---|---|---|---|---|---|---|---|---|---|
| 8 | rs36980859 | 69070580 | 62925313 | 78310523 | G | A | 0.901 | 8.377791 | 4.19E-09 | 171 | StepLengthVariance;StepWidthVariance |
| 8 | rs36946168 | 75004351 | 75004351 | 79923292 | G | A | 0.072 | 5.302166 | 4.99E-06 | 24 | StepLengthVariance |
| 8 | rs13479883 | 87261761 | 77371854 | 96983161 | C | A | 0.634 | 4.813878 | 1.54E-05 | 194 | AmplitudeTailBase;StrideLength |
| 8 | rs33380934 | 90493495 | 80884633 | 99118842 | G | C | 0.357 | 6.118978 | 7.60E-07 | 174 | AmplitudeTailBase;StrideLength |
| 8 | rs49711111 | 116748950 | 1.14E+08 | 1.17E+08 | G | A | 0.929 | 4.884716 | 1.30E-05 | 6 | StrideCount |
| 8 | rs33552938 | 122764065 | 1.14E+08 | 1.29E+08 | T | G | 0.586 | 5.171166 | 6.74E-06 | 146 | StrideCount;StepLength;StrideLength |
| 9 | rs36606629 | 21266919 | 16357398 | 29916851 | G | A | 0.758 | 5.06339 | 8.64E-06 | 145 | StepLengthVariance;TemporalSymmetryVariance |
| 9 | rs38311488 | 27226859 | 20717303 | 37111826 | T | C | 0.153 | 4.760101 | 1.74E-05 | 141 | DistanceTraveled;AmplitudeTailBaseVariance;StepLengthVariance;StrideLength;TemporalSymmetryVariance |
| 9 | rs29693439 | 34619983 | 28354221 | 44232376 | T | C | 0.24 | 7.667439 | 2.15E-08 | 193 | StrideCount;DistanceTraveled;AngularVelocityVariance;AmplitudeTailBaseVariance;AmplitudeNose;StrideLength;AmplitudeTailTip |
| 9 | rs36346401 | 42215881 | 34622888 | 50230616 | T | G | 0.84 | 5.108898 | 7.78E-06 | 254 | StrideCount;DistanceTraveled;AngularVelocityVariance;AmplitudeTailBaseVariance;AmplitudeNose;AmplitudeNoseVariance;StepWidthVariance;StrideLength;AmplitudeTailTip |
| 9 | rs36659530 | 43640452 | 34948067 | 47988873 | C | A | 0.21 | 5.59318 | 2.55E-06 | 237 | StrideCount;DistanceTraveled;AngularVelocityVariance;AmplitudeTailBaseVariance;AmplitudeNose;StepWidthVariance;StrideLength;AmplitudeTailTip |
| 9 | rs29604964 | 46479849 | 36941972 | 56380869 | T | C | 0.777 | 6.925234 | 1.19E-07 | 294 | StrideCount;DistanceTraveled;AngularVelocityVariance;AmplitudeTailBaseVariance;LimbDutyVariance;AmplitudeNose;AmplitudeNoseVariance;StepWidthVariance;StrideLength;TemporalSymmetryVariance;AmplitudeTailTip |
| 9 | rs50961530 | 47912845 | 38255681 | 48115642 | T | G | 0.912 | 15.10385 | 7.87E-16 | 170 | StrideCount;DistanceTraveled;AngularVelocityVariance;AmplitudeTailBaseVariance;AmplitudeNose;StepWidthVariance;StrideLength;AmplitudeTailTip |

FIG. 22 continued

| | | | | | | | | | | | |
|---|---|---|---|---|---|---|---|---|---|---|---|
| 9 | rs48018879 | 48513331 | 47916967 | 58435633 | G | A | 0.927 | 6.92581 | 1.19E-07 | 133 | AmplitudeTailBaseVariance;LimbDutyVariance;AmplitudeNose;AmplitudeNoseVariance;StrideLengthVariance;TemporalSymmetryVariance |
| 9 | rs38764974 | 56515607 | 48504349 | 65780868 | G | A | 0.71 | 5.648686 | 2.25E-06 | 203 | AmplitudeTailBaseVariance;LimbDutyVariance;AmplitudeNose;AmplitudeNoseVariance;StepWidth;StrideLengthVariance;TemporalSymmetryVariance |
| 9 | rs49639053 | 62507330 | 59662105 | 69696362 | T | A | 0.445 | 5.19551 | 6.38E-06 | 87 | StepWidth;StepWidthVariance |
| 9 | rs47917053 | 69700792 | 61743177 | 71699261 | T | C | 0.854 | 6.4153 | 3.84E-07 | 94 | StepWidth;StepWidthVariance |
| 9 | rs37728078 | 93460877 | 83480619 | 1E+08 | G | A | 0.927 | 6.601089 | 2.51E-07 | 96 | AmplitudeNose;StepWidthVariance;StrideLengthVariance;TemporalSymmetryVariance |
| 9 | rs38626324 | 95289923 | 85622946 | 1.02E+08 | T | C | 0.912 | 15.10385 | 7.87E-16 | 99 | AmplitudeNose;StepLengthVariance;StepWidthVariance;StrideLengthVariance;TemporalSymmetry;TemporalSymmetryVariance |
| 9 | rs30490974 | 101589905 | 92280832 | 1.07E+08 | T | C | 0.492 | 5.064414 | 8.62E-06 | 108 | AmplitudeTailBaseVariance;AmplitudeNose;StepLengthVariance;StepWidthVariance;StrideLengthVariance;TemporalSymmetry;TemporalSymmetryVariance |
| 9 | rs38880181 | 104360186 | 94447224 | 1.14E+08 | G | A | 0.24 | 8.306064 | 4.94E-09 | 254 | AmplitudeTailBaseVariance;AmplitudeNose;StepLengthVariance;StepWidthVariance;StrideLengthVariance;TemporalSymmetry;TemporalSymmetryVariance |
| 9 | rs46168336 | 123945647 | 1.23E+08 | 1.24E+08 | G | A | 0.071 | 5.143977 | 7.18E-06 | 22 | AmplitudeNoseVariance |
| 10 | rs29332088 | 9424091 | 7826604 | 15592762 | T | A | 0.204 | 5.66133 | 2.18E-06 | 29 | AmplitudeNose |
| 10 | rs47344828 | 15840659 | 11130756 | 20531933 | G | C | 0.211 | 5.97228 | 1.07E-06 | 43 | DistanceTraveled;StepWidthVariance;StrideLength |
| 10 | rs33609233 | 18203090 | 8404421 | 28060294 | T | C | 0.844 | 4.85961 | 1.38E-05 | 101 | DistanceTraveled;AmplitudeNose;StepWidthVariance;StrideLength |
| 10 | rs37401073 | 66943997 | 63508324 | 69162651 | G | A | 0.077 | 5.770178 | 1.70E-06 | 13 | LimbDutyVariance;AmplitudeNoseVariance;StrideLengthVariance;TemporalSymmetryVariance |
| 10 | rs36565581 | 67564344 | 66402797 | 75412973 | T | C | 0.844 | 16.21136 | 6.15E-17 | 34 | AmplitudeTailBaseVariance;LimbDutyVariance;AmplitudeNoseVariance;StrideLengthVariance;TemporalSymmetryVariance;AmplitudeTailTip |

FIG. 22 continued

| | | | | | | | | | | | |
|---|---|---|---|---|---|---|---|---|---|---|---|
| 10 | rs13480647 | 72780332 | 67885464 | 72780332 | G | A | 0.778 | 5.471475 | 3.38E-06 | 20 | LimbDutyVariance;AmplitudeNoseVariance;StrideLengthVariance;AmplitudeTailTip |
| 10 | rs29360326 | 82922269 | 74666299 | 91087191 | T | C | 0.214 | 6.878082 | 1.32E-07 | 321 | AmplitudeTailBaseVariance;AmplitudeNose;AmplitudeNoseVariance;StrideLengthVariance |
| 10 | rs48992951 | 85603156 | 75681514 | 91410321 | T | C | 0.092 | 5.25681 | 5.54E-06 | 310 | AmplitudeTailBaseVariance;AmplitudeNose;AmplitudeNoseVariance;StrideLengthVariance |
| 10 | rs3700716 | 92018031 | 83910884 | 94349064 | T | C | 0.78 | 5.22241 | 5.99E-06 | 71 | DistanceTraveled;StrideLength;StrideLengthVariance |
| 10 | rs48304347 | 100068478 | 90455032 | 1.07E+08 | T | G | 0.366 | 4.793771 | 1.61E-05 | 76 | DistanceTraveled;StrideLength;TemporalSymmetryVariance |
| 10 | rs50584051 | 115104399 | 1.15E+08 | 1.19E+08 | G | A | 0.078 | 5.308955 | 4.91E-06 | 44 | LimbDutyVariance;AmplitudeNoseVariance;StrideLengthVariance;TemporalSymmetryVariance |
| 10 | rs52018876 | 119702755 | 1.1E+08 | 1.28E+08 | T | A | 0.805 | 4.953575 | 1.11E-05 | 120 | AngularVelocityVariance;LimbDutyVariance;AmplitudeNoseVariance;StrideLength;StrideLengthVariance;TemporalSymmetryVariance |
| 10 | rs225223668 | 121155185 | 1.15E+08 | 1.28E+08 | T | A | 0.925 | 5.552253 | 2.80E-06 | 136 | AngularVelocityVariance;LimbDutyVariance;AmplitudeNoseVariance;StrideLength;StrideLengthVariance;TemporalSymmetryVariance |
| 10 | rs51972621 | 122784327 | 1.13E+08 | 1.3E+08 | T | G | 0.677 | 5.42711 | 3.74E-06 | 229 | AngularVelocityVariance;LimbDutyVariance;AmplitudeNoseVariance;StrideLength;StrideLengthVariance;TemporalSymmetryVariance |
| 11 | rs26922902 | 4646882 | 3335983 | 13624724 | G | A | 0.38 | 4.898009 | 1.26E-05 | 98 | StepWidthVariance;TemporalSymmetry |
| 11 | rs51597348 | 9725880 | 6584417 | 19663106 | T | G | 0.897 | 5.719276 | 1.91E-06 | 39 | StepWidthVariance |
| 11 | rs6297874 | 32991124 | 23104715 | 42593828 | T | C | 0.76 | 5.966839 | 1.08E-06 | 85 | DistanceTraveled;LimbDuty |
| 11 | rs28186278 | 40096987 | 30183500 | 48728012 | T | C | 0.447 | 5.037577 | 9.17E-06 | 91 | DistanceTraveled;LimbDuty;StepLengthVariance;StrideLength |
| 11 | rs26959175 | 47982190 | 38062863 | 57162935 | T | C | 0.265 | 7.145212 | 7.16E-08 | 178 | DistanceTraveled;StepLengthVariance;StepWidthVariance;StrideLength;TemporalSymmetry |
| 11 | rs26972008 | 60730992 | 56524449 | 65017586 | G | C | 0.926 | 5.891332 | 1.28E-06 | 141 | StrideLengthVariance;TemporalSymmetry |
| 11 | rs28232950 | 71372681 | 61528127 | 73170368 | G | A | 0.161 | 4.991067 | 1.02E-05 | 214 | StepLengthVariance |

FIG. 22 continued

| | | | | | | | | | | | |
|---|---|---|---|---|---|---|---|---|---|---|---|
| 11 | rs28247873 | 78911850 | 69875605 | 88502226 | T | C | 0.937 | 10.45206 | 3.53E-11 | 365 | AngularVelocityVariance;AmplitudeNoseVariance;StepLength;StepLengthVariance;StrideLengthVariance |
| 11 | rs28191437 | 82988523 | 80257422 | 92979275 | T | C | 0.422 | 5.918688 | 1.21E-06 | 134 | AngularVelocityVariance;LimbDutyVariance;AmplitudeNose;StepLength;StepWidthVariance;StrideLengthVariance |
| 11 | rs27100035 | 88869863 | 86454081 | 91393222 | G | A | 0.857 | 5.239848 | 5.76E-06 | 53 | LimbDutyVariance;AmplitudeNose;StepWidthVariance;StrideLengthVariance |
| 11 | rs27078808 | 89640276 | 83019450 | 97956514 | T | G | 0.204 | 5.684273 | 2.07E-06 | 208 | LimbDutyVariance;AmplitudeNose;StepLength;StepWidthVariance;StrideLengthVariance |
| 11 | rs27091032 | 90619035 | 82440884 | 97002062 | G | A | 0.912 | 15.20281 | 6.27E-16 | 191 | AngularVelocityVariance;LimbDutyVariance;AmplitudeNose;StepLength;StepWidthVariance;StrideLengthVariance |
| 11 | rs29445049 | 93219167 | 83283510 | 1.03E+08 | G | A | 0.383 | 6.153317 | 7.03E-07 | 420 | LimbDutyVariance;AmplitudeNose;StepLength;StepWidthVariance;StrideLengthVariance;TemporalSymmetry |
| 11 | rs3154922 | 100810992 | 92468299 | 1.08E+08 | G | A | 0.49 | 5.760734 | 1.73E-06 | 389 | LimbDutyVariance;AmplitudeNose;StepLength;StrideLengthVariance;TemporalSymmetry;TemporalSymmetryVariance |
| 11 | rs27007705 | 103211310 | 93834441 | 1.13E+08 | G | A | 0.936 | 9.616477 | 2.42E-10 | 411 | LimbDutyVariance;AmplitudeNose;StepLength;StepWidthVariance;StrideLengthVariance;TemporalSymmetry;TemporalSymmetryVariance |
| 11 | rs29415720 | 105793357 | 96164936 | 1.16E+08 | T | A | 0.223 | 6.826309 | 1.49E-07 | 411 | AngularVelocity;LimbDutyVariance;AmplitudeNose;StepWidthVariance;StrideLengthVariance;TemporalSymmetry;TemporalSymmetryVariance |
| 11 | rs27004883 | 109383378 | 1E+08 | 1.16E+08 | T | C | 0.129 | 4.767232 | 1.71E-05 | 277 | AngularVelocity;LimbDutyVariance;AmplitudeNose;StepWidthVariance;StrideLengthVariance;TemporalSymmetry;TemporalSymmetryVariance |
| 11 | rs27031381 | 115589091 | 1.1E+08 | 1.17E+08 | G | A | 0.414 | 5.088352 | 8.16E-06 | 109 | AngularVelocity;StrideLengthVariance |
| 11 | rs27030534 | 117354840 | 1.07E+08 | 1.18E+08 | G | A | 0.926 | 4.954909 | 1.11E-05 | 144 | AngularVelocity;AmplitudeNose;StepWidthVariance;StrideLengthVariance;TemporalSymmetryVariance |

FIG. 22 continued

| | | | | | | | | | | | |
|---|---|---|---|---|---|---|---|---|---|---|---|
| 12 | rs46848480 | 5752816 | 3904314 | 15720586 | G | A | 0.106 | 6.687162 | 2.06E-07 | 45 | DistanceTraveled;AngularVelocityVariance;StepLength;StepWidthVariance;StrideLength;StrideLengthVariance |
| 12 | rs50132665 | 13061994 | 5611374 | 17082651 | G | A | 0.865 | 7.187387 | 6.50E-08 | 34 | DistanceTraveled;AngularVelocityVariance;LimbDuty;StepLength;StepWidthVariance;StrideLength |
| 12 | rs29200284 | 16699209 | 6939721 | 26656921 | T | A | 0.395 | 4.764825 | 1.72E-05 | 60 | DistanceTraveled;AngularVelocityVariance;LimbDuty;StepLength;StrideLength;TemporalSymmetry |
| 12 | rs51474140 | 25632234 | 15833645 | 28272301 | G | A | 0.503 | 5.304579 | 4.96E-06 | 34 | LimbDuty;TemporalSymmetry |
| 12 | rs29193514 | 34347193 | 25195354 | 37471369 | G | A | 0.907 | 5.457334 | 3.49E-06 | 57 | LimbDuty;LimbDutyVariance;AmplitudeNoseVariance;StrideLengthVariance;TemporalSymmetry |
| 12 | rs29138639 | 36689834 | 28696358 | 44816069 | T | C | 0.598 | 5.734793 | 1.84E-06 | 60 | LimbDutyVariance;AmplitudeNoseVariance;StrideLengthVariance;TemporalSymmetry |
| 12 | rs29178200 | 46703829 | 36927120 | 54328820 | G | A | 0.454 | 6.164535 | 6.85E-07 | 34 | TemporalSymmetry |
| 12 | rs31986329 | 58557762 | 51195317 | 68492863 | C | A | 0.889 | 5.818024 | 1.52E-06 | 63 | LimbDutyVariance;AmplitudeNoseVariance;StepWidthVariance;StrideLengthVariance;TemporalSymmetry;TemporalSymmetryVariance |
| 12 | rs36438016 | 59492637 | 50757252 | 64409661 | T | G | 0.846 | 5.932937 | 1.17E-06 | 52 | LimbDutyVariance;AmplitudeNoseVariance;StepWidthVariance;StrideLengthVariance;TemporalSymmetry;TemporalSymmetryVariance |
| 12 | rs38242778 | 60124626 | 58795461 | 66743817 | T | A | 0.902 | 7.043327 | 9.05E-08 | 18 | LimbDutyVariance;AmplitudeNoseVariance;StrideLengthVariance;TemporalSymmetry;TemporalSymmetryVariance |
| 12 | rs51955841 | 72078229 | 70089526 | 79481301 | T | G | 0.905 | 5.001686 | 9.96E-06 | 78 | DistanceTraveled;AmplitudeNoseVariance;StepLengthVariance |
| 12 | rs32415796 | 75501746 | 67018484 | 84011503 | T | C | 0.909 | 5.302139 | 4.99E-06 | 136 | DistanceTraveled;LimbDutyVariance;AmplitudeNoseVariance;StepLengthVariance;StrideLengthVariance;TemporalSymmetryVariance |
| 12 | rs46961925 | 80236101 | 71643035 | 90085012 | G | A | 0.868 | 8.072736 | 8.46E-09 | 192 | DistanceTraveled;LimbDutyVariance;AmplitudeNoseVariance;StepLengthVariance;StrideLengthVariance;TemporalSymmetryVariance |
| 12 | rs32974900 | 101290484 | 92656928 | 1.02E+08 | T | C | 0.071 | 5.714475 | 1.93E-06 | 30 | AmplitudeNoseVariance;StepLengthVariance |

FIG. 22 continued

| | | | | | | | | | | | |
|---|---|---|---|---|---|---|---|---|---|---|---|
| 12 | rs36807116 | 102415824 | 1.01E+08 | 1.05E+08 | T | C | 0.819 | 5.95154 | 1.12E-06 | 60 | AmplitudeTailBaseVariance;AmplitudeNoseVariance |
| 12 | rs33421279 | 112403263 | 1.06E+08 | 1.19E+08 | G | A | 0.146 | 6.034063 | 9.25E-07 | 98 | StepLengthVariance;StepWidthVariance;StrideLengthVariance;TemporalSymmetryVariance |
| 12 | rs33450816 | 112731768 | 1.08E+08 | 1.19E+08 | G | C | 0.12 | 4.860989 | 1.38E-05 | 89 | StepLengthVariance;StepWidthVariance;StrideLengthVariance;TemporalSymmetryVariance |
| 12 | rs45978599 | 117436430 | 1.08E+08 | 1.19E+08 | T | C | 0.84 | 5.882122 | 1.31E-06 | 90 | StepLengthVariance;StepWidthVariance;StrideLengthVariance;TemporalSymmetryVariance |
| 13 | rs30052844 | 3750784 | 3007137 | 13102704 | T | A | 0.427 | 4.812601 | 1.54E-05 | 40 | AngularVelocityVariance |
| 13 | rs29947204 | 24883988 | 17291387 | 26117473 | T | C | 0.148 | 5.164231 | 6.85E-06 | 159 | TemporalSymmetryVariance |
| 13 | rs36395220 | 36439484 | 30459929 | 45437605 | T | C | 0.594 | 5.052888 | 8.85E-06 | 89 | StepLengthVariance |
| 13 | rs48027011 | 58350024 | 55287549 | 63706664 | G | A | 0.074 | 5.866546 | 1.36E-06 | 96 | StrideCount;AngularVelocityVariance;LimbDutyVariance;StrideLength;StrideLengthVariance |
| 13 | rs29875499 | 59737349 | 53552348 | 69471474 | G | A | 0.145 | 5.028228 | 9.37E-06 | 184 | StrideCount;AngularVelocityVariance;LimbDutyVariance;StepLength;StrideLength;StrideLengthVariance |
| 13 | rs33884103 | 62893868 | 53946635 | 70698859 | G | A | 0.751 | 6.924976 | 1.19E-07 | 190 | StrideCount;AngularVelocityVariance;LimbDutyVariance;StepLength;StrideLength;StrideLengthVariance |
| 13 | rs47096917 | 75785971 | 67021496 | 85784481 | T | C | 0.204 | 5.698044 | 2.00E-06 | 99 | AmplitudeNose |
| 13 | rs29224622 | 110435723 | 1.01E+08 | 1.19E+08 | G | A | 0.796 | 5.698044 | 2.00E-06 | 71 | AmplitudeNose;StepWidthVariance;TemporalSymmetry |
| 13 | rs47698323 | 113653018 | 1.08E+08 | 1.15E+08 | C | A | 0.894 | 4.923266 | 1.19E-05 | 42 | AmplitudeNose;StepWidthVariance |
| 13 | rs47665460 | 116302023 | 1.07E+08 | 1.18E+08 | T | C | 0.163 | 5.366221 | 4.30E-06 | 45 | AmplitudeNose;StepWidthVariance;TemporalSymmetry |
| 14 | rs30909046 | 29645740 | 19728081 | 34951276 | G | A | 0.417 | 4.910394 | 1.23E-05 | 157 | AngularVelocityVariance |
| 14 | rs51177573 | 41007477 | 37721050 | 45553742 | T | C | 0.078 | 4.788565 | 1.63E-05 | 92 | DistanceTraveled;AngularVelocityVariance;StepWidth;StrideLength;StrideLengthVariance |
| 14 | rs39144568 | 41425921 | 32808695 | 47008484 | G | C | 0.293 | 5.687497 | 2.05E-06 | 141 | DistanceTraveled;AngularVelocityVariance;StepWidth;StrideLength;StrideLengthVariance |
| 14 | rs50683743 | 45066257 | 41204550 | 54683365 | G | A | 0.859 | 4.794387 | 1.61E-05 | 215 | DistanceTraveled;AngularVelocityVariance;AmplitudeTailBaseVariance;AmplitudeNose;StepLength,StrideLength;StrideLengthVariance |

FIG. 22 continued

| | | | | | | | | | | | |
|---|---|---|---|---|---|---|---|---|---|---|---|
| 14 | rs31290321 | 47960458 | 38434675 | 56758423 | T | C | 0.548 | 6.208615 | 6.19E-07 | 304 | DistanceTraveled;AngularVelocityVariance;AmplitudeTailBaseVariance;AmplitudeNose;StepLength;StepWidth;StrideLength;StrideLengthVariance |
| 14 | rs3155045 | 51903243 | 45576045 | 61768454 | T | A | 0.195 | 7.325948 | 4.72E-08 | 259 | AmplitudeTailBaseVariance;AmplitudeNose;StepLength |
| 14 | rs30445059 | 70877235 | 68791914 | 77997437 | G | A | 0.726 | 4.786986 | 1.63E-05 | 75 | DistanceTraveled;AmplitudeNose;StepLengthVariance;StrideLength |
| 14 | rs30809206 | 73005167 | 63914727 | 78040815 | G | C | 0.816 | 4.780186 | 1.66E-05 | 121 | DistanceTraveled;AmplitudeNose;StepLengthVariance;StrideLength |
| 14 | rs30420250 | 74973385 | 65033481 | 79725803 | G | A | 0.533 | 6.115985 | 7.66E-07 | 126 | DistanceTraveled;AmplitudeNose;StepLengthVariance;StrideLength |
| 14 | rs32568665 | 111983539 | 1.03E+08 | 1.22E+08 | C | A | 0.645 | 4.723212 | 1.89E-05 | 38 | StrideCount;DistanceTraveled;AmplitudeTailBase;StrideLength |
| 14 | rs46553416 | 113715844 | 1.05E+08 | 1.23E+08 | G | A | 0.143 | 5.48906 | 3.24E-06 | 41 | StrideCount;DistanceTraveled;AmplitudeTailBase;LimbDutyVariance;StepWidth;StrideLength;TemporalSymmetryVariance |
| 14 | rs48277673 | 122210263 | 1.12E+08 | 1.25E+08 | T | C | 0.454 | 5.341499 | 4.56E-06 | 36 | StrideCount;DistanceTraveled;LimbDutyVariance;StepWidth;StrideLength;TemporalSymmetryVariance |
| 14 | rs45974385 | 122882246 | 1.17E+08 | 1.25E+08 | G | A | 0.871 | 5.125887 | 7.48E-06 | 34 | DistanceTraveled;LimbDutyVariance;StepWidth;TemporalSymmetryVariance |
| 15 | rs36994453 | 12901226 | 7610880 | 22859097 | T | C | 0.797 | 5.289187 | 5.14E-06 | 44 | AngularVelocityVariance;StepWidth;TemporalSymmetry |
| 15 | rs31960571 | 18943864 | 9087429 | 27522358 | T | G | 0.162 | 5.089886 | 8.13E-06 | 44 | AngularVelocityVariance;StepWidth;TemporalSymmetry |
| 15 | rs32941840 | 28098747 | 20464394 | 38034360 | G | A | 0.092 | 5.114023 | 7.69E-06 | 56 | DistanceTraveled;AngularVelocityVariance;LimbDuty;StepWidthVariance;StrideLength |
| 15 | rs33056460 | 29278117 | 22482996 | 38067801 | T | G | 0.15 | 5.653515 | 2.22E-06 | 54 | DistanceTraveled;AngularVelocityVariance;LimbDuty;StepWidthVariance;StrideLength |
| 15 | rs6377844 | 30696768 | 20702051 | 40689005 | T | C | 0.816 | 6.322625 | 4.76E-07 | 70 | DistanceTraveled;AngularVelocityVariance;LimbDuty;StepWidthVariance;StrideLength |
| 15 | rs32291436 | 45808077 | 37360484 | 50868722 | T | C | 0.319 | 5.003647 | 9.92E-06 | 36 | DistanceTraveled;StepWidthVariance;StrideLength;TemporalSymmetry |

FIG. 22 continued

| | | | | | | | | | | | |
|---|---|---|---|---|---|---|---|---|---|---|---|
| 15 | rs50455382 | 48624275 | 38915970 | 58554177 | C | A | 0.825 | 4.780917 | 1.66E-05 | 63 | DistanceTraveled;StepLength;StepWidthVariance;StrideLength;StrideLengthVariance;TemporalSymmetry;TemporalSymmetryVariance |
| 15 | rs32276329 | 50802051 | 41522834 | 54430052 | C | A | 0.729 | 4.861009 | 1.38E-05 | 27 | DistanceTraveled;StepLength;StepWidthVariance;StrideLength;TemporalSymmetry |
| 15 | rs13482576 | 51441484 | 41452393 | 60098289 | G | A | 0.761 | 5.201945 | 6.28E-06 | 64 | DistanceTraveled;LimbDutyVariance;StepLength;StepLengthVariance;StepWidth;StepWidthVariance;StrideLength;StrideLengthVariance;TemporalSymmetry;TemporalSymmetryVariance |
| 15 | rs37697135 | 58632871 | 48796498 | 64345782 | T | C | 0.156 | 9.668386 | 2.15E-10 | 58 | LimbDutyVariance;StepLength;StepLengthVariance;StepWidth;StrideLengthVariance;TemporalSymmetry;TemporalSymmetryVariance |
| 15 | rs36585973 | 61483272 | 51507071 | 71441518 | G | A | 0.753 | 5.934073 | 1.16E-06 | 75 | LimbDutyVariance;AmplitudeNoseVariance;StepLength;StepLengthVariance;StepWidth;StrideLengthVariance;TemporalSymmetry;TemporalSymmetryVariance |
| 15 | rs31251129 | 68583080 | 66904336 | 77827309 | T | C | 0.88 | 7.475709 | 3.34E-08 | 133 | AmplitudeNoseVariance;TemporalSymmetry |
| 15 | rs31551418 | 78539610 | 70773557 | 88469701 | G | A | 0.337 | 5.007014 | 9.84E-06 | 304 | AngularVelocityVariance;TemporalSymmetry |
| 15 | rs32172171 | 92052846 | 84719381 | 98606000 | T | C | 0.623 | 5.165458 | 6.83E-06 | 123 | StrideCount;LimbDutyVariance;StrideLengthVariance;TemporalSymmetryVariance |
| 15 | rs37270543 | 93676533 | 87455002 | 1.02E+08 | T | C | 0.378 | 6.170458 | 6.75E-07 | 205 | StrideCount;LimbDutyVariance;StrideLengthVariance;TemporalSymmetryVariance |
| 15 | rs49125316 | 96173725 | 91437407 | 1.02E+08 | T | C | 0.106 | 6.331913 | 4.66E-07 | 149 | StrideCount;LimbDutyVariance;StrideLengthVariance;TemporalSymmetryVariance |
| 16 | rs4161545 | 11040586 | 5952479 | 19883079 | T | C | 0.304 | 5.213143 | 6.12E-06 | 148 | AmplitudeNose;StepLengthVariance;StrideLengthVariance |
| 16 | rs51384728 | 14931958 | 5596392 | 24642134 | G | A | 0.81 | 8.030014 | 9.33E-09 | 205 | AmplitudeNose;StepLengthVariance;StrideLengthVariance |
| 16 | rs4164765 | 15144159 | 5606907 | 23467605 | T | A | 0.796 | 5.740464 | 1.82E-06 | 199 | AmplitudeNose;StepLengthVariance;StrideLengthVariance |

FIG. 22 continued

| | | | | | | | | | | | |
|---|---|---|---|---|---|---|---|---|---|---|---|
| 16 | rs49780112 | 28703139 | 28580512 | 29491203 | C | A | 0.916 | 7.493147 | 3.21E-08 | 5 | AmplitudeTailBaseVariance;LimbDutyVariance;AmplitudeNoseVariance;StrideLengthVariance |
| 16 | rs4172840 | 35598396 | 27062881 | 45573621 | T | C | 0.199 | 7.141162 | 7.22E-08 | 156 | AmplitudeTailBase;AmplitudeTailBaseVariance;LimbDutyVariance;AmplitudeNoseVariance;StrideLengthVariance;AmplitudeTailTip |
| 16 | rs51391412 | 38019377 | 36506777 | 43740368 | G | C | 0.935 | 6.176385 | 6.66E-07 | 40 | AmplitudeTailBase;StrideLengthVariance;AmplitudeTailTip |
| 16 | rs4174373 | 38110133 | 28971830 | 48020167 | T | A | 0.499 | 6.219231 | 6.04E-07 | 161 | AmplitudeTailBase;AmplitudeTailBaseVariance;AmplitudeNoseVariance;StrideLengthVariance;AmplitudeTailTip |
| 16 | rs46144327 | 38817198 | 29032965 | 48778709 | T | C | 0.635 | 4.801478 | 1.58E-05 | 166 | AmplitudeTailBase;AmplitudeTailBaseVariance;AmplitudeNoseVariance;StrideLengthVariance;AmplitudeTailTip |
| 16 | rs4200756 | 71165784 | 62242736 | 80858192 | T | C | 0.223 | 11.67491 | 2.11E-12 | 30 | StrideCount;DistanceTraveled;AngularVelocityVariance;AmplitudeTailBaseVariance;AmplitudeNose;AmplitudeNoseVariance |
| 16 | rs33413986 | 84131571 | 76738189 | 88021861 | T | G | 0.501 | 5.34755 | 4.49E-06 | 26 | StepWidth;StrideLengthVariance |
| 16 | rs46716213 | 84782930 | 83859298 | 93997905 | T | C | 0.08 | 5.761779 | 1.73E-06 | 103 | StepWidth;StrideLengthVariance |
| 17 | rs3153902 | 25025746 | 16426664 | 33526063 | T | C | 0.732 | 5.304536 | 4.96E-06 | 357 | StrideCount;DistanceTraveled;AngularVelocityVariance;StepLength;StepWidthVariance;StrideLength;TemporalSymmetryVariance |
| 17 | rs49059702 | 29847591 | 21556044 | 33439885 | C | A | 0.138 | 5.393321 | 4.04E-06 | 299 | StrideCount;DistanceTraveled;AngularVelocityVariance;StepLength;StepWidthVariance;StrideLength;TemporalSymmetryVariance |
| 17 | rs51206791 | 30579529 | 20962307 | 40431157 | G | A | 0.595 | 7.060758 | 8.69E-08 | 553 | StrideCount;DistanceTraveled;AngularVelocityVariance;AmplitudeNoseVariance;StepLength;StepWidthVariance;StrideLength;TemporalSymmetryVariance |
| 17 | rs46766175 | 31015823 | 23981985 | 31422500 | T | C | 0.091 | 6.765408 | 1.72E-07 | 202 | DistanceTraveled;AngularVelocityVariance;StepLength;StepWidthVariance;StrideLength;TemporalSymmetryVariance |

FIG. 22 continued

| | | | | | | | | | | | |
|---|---|---|---|---|---|---|---|---|---|---|---|
| 17 | rs6163261 | 31619650 | 24450098 | 38182166 | G | A | 0.655 | 5.255907 | 5.55E-06 | 454 | StrideCount;DistanceTraveled;AngularVelocityVariance;AmplitudeNoseVariance;StepLength;StepWidthVariance;StrideLength;TemporalSymmetryVariance |
| 17 | rs51666106 | 33535271 | 23708208 | 43527632 | G | A | 0.83 | 5.320582 | 4.78E-06 | 528 | StrideCount;DistanceTraveled;AngularVelocityVariance;AmplitudeNoseVariance;StepLength;StepWidthVariance;StrideLength;StrideLengthVariance;TemporalSymmetryVariance |
| 17 | rs49919980 | 68059714 | 65855093 | 77411942 | G | A | 0.356 | 5.181839 | 6.58E-06 | 54 | StrideCount;AmplitudeNose |
| 17 | rs33585596 | 69314294 | 64025872 | 79301303 | G | A | 0.184 | 5.334528 | 4.63E-06 | 76 | StrideCount;AmplitudeNose |
| 17 | rs49681869 | 74888199 | 66293121 | 78282887 | T | C | 0.214 | 5.426549 | 3.74E-06 | 49 | StrideCount;AmplitudeNose |
| 17 | rs33397214 | 83071167 | 75195983 | 92812847 | T | C | 0.325 | 6.914472 | 1.22E-07 | 83 | LimbDutyVariance;AmplitudeNose;AmplitudeNoseVariance;StrideLengthVariance;TemporalSymmetryVariance |
| 17 | rs48213845 | 85225680 | 83596370 | 87668411 | G | A | 0.074 | 16.51342 | 3.07E-17 | 31 | LimbDutyVariance;StrideLengthVariance;TemporalSymmetryVariance |
| 17 | rs48965328 | 86286733 | 76469100 | 93601786 | T | C | 0.317 | 6.029994 | 9.33E-07 | 81 | LimbDutyVariance;AmplitudeNose;AmplitudeNoseVariance;StrideLengthVariance;TemporalSymmetryVariance |
| 17 | rs48345208 | 89308352 | 83867195 | 92900646 | C | A | 0.073 | 6.740441 | 1.82E-07 | 41 | LimbDutyVariance;AmplitudeNoseVariance;StrideLengthVariance;TemporalSymmetryVariance |
| 17 | rs46029911 | 94519788 | 87070784 | 94519788 | T | G | 0.93 | 5.433056 | 3.69E-06 | 20 | StrideCount;LimbDutyVariance;AmplitudeNoseVariance;StrideLengthVariance |
| 18 | rs29677188 | 8454006 | 3257767 | 15555069 | G | A | 0.304 | 5.671109 | 2.13E-06 | 53 | LimbDutyVariance;AmplitudeNoseVariance;StepLengthVariance;StrideLengthVariance;TemporalSymmetryVariance |
| 18 | rs30986841 | 12197240 | 11684451 | 16127469 | T | C | 0.077 | 6.237733 | 5.78E-07 | 20 | LimbDutyVariance;AmplitudeNoseVariance;StepLengthVariance;StrideLengthVariance;TemporalSymmetryVariance |
| 18 | rs49755180 | 17688536 | 14160162 | 20579240 | T | G | 0.825 | 8.170961 | 6.75E-09 | 16 | AmplitudeNoseVariance;StepLengthVariance;StrideLengthVariance;TemporalSymmetryVariance |

FIG. 22 continued

| | | | | | | | | | | | |
|---|---|---|---|---|---|---|---|---|---|---|---|
| 18 | rs31754562 | 37871873 | 27915405 | 39300608 | C | A | 0.088 | 15.21846 | 6.05E-16 | 164 | AmplitudeNoseVariance;StepWidthVariance;TemporalSymmetryVariance |
| 18 | rs31707866 | 38929751 | 30424859 | 43261305 | T | C | 0.082 | 4.908528 | 1.23E-05 | 178 | AmplitudeNoseVariance;StepWidthVariance;TemporalSymmetryVariance |
| 18 | rs29576114 | 43963547 | 36681363 | 47880295 | G | A | 0.223 | 6.857364 | 1.39E-07 | 139 | AmplitudeTailBaseVariance;AmplitudeNose;AmplitudeNoseVariance;StepWidthVariance |
| 18 | rs48387983 | 52537040 | 52346064 | 62124792 | T | C | 0.926 | 5.033687 | 9.25E-06 | 63 | StrideCount;AngularVelocityVariance;AmplitudeTailBaseVariance;AmplitudeNose;AmplitudeNoseVariance;TemporalSymmetry;TemporalSymmetryVariance;AmplitudeTailTipVariance |
| 18 | rs47573381 | 54896509 | 53703077 | 64504831 | T | A | 0.862 | 5.866625 | 1.36E-06 | 68 | StrideCount;AngularVelocityVariance;AmplitudeTailBaseVariance;AmplitudeNose;AmplitudeNoseVariance;StepLengthVariance;TemporalSymmetry;AmplitudeTailTip;AmplitudeTailTipVariance |
| 18 | rs3710496 | 57960961 | 47961302 | 67908142 | T | G | 0.223 | 11.7642 | 1.72E-12 | 116 | StrideCount;AngularVelocityVariance;AmplitudeTailBase;AmplitudeTailBaseVariance;AmplitudeNose;AmplitudeNoseVariance;StepLengthVariance;StrideLength;TemporalSymmetry;TemporalSymmetryVariance;AmplitudeTailTip;AmplitudeTailTipVariance |
| 18 | rs30070807 | 59053527 | 49261350 | 68607927 | G | A | 0.22 | 4.789475 | 1.62E-05 | 120 | StrideCount;AngularVelocityVariance;AmplitudeTailBase;AmplitudeTailBaseVariance;LimbDutyVariance;AmplitudeNose;AmplitudeNoseVariance;StepLengthVariance;StrideLength;TemporalSymmetry;TemporalSymmetryVariance;AmplitudeTailTip;AmplitudeTailTipVariance |

FIG. 22 continued

| | | | | | | | | | | | |
|---|---|---|---|---|---|---|---|---|---|---|---|
| 18 | rs30019314 | 60051264 | 56481788 | 65300762 | G | A | 0.546 | 4.875927 | 1.33E-05 | 68 | StrideCount;AngularVelocityVariance;AmplitudeTailBase;AmplitudeTailBaseVariance;AmplitudeNose;AmplitudeNoseVariance;StepLengthVariance;TemporalSymmetry;AmplitudeTailTip;AmplitudeTailTipVariance |
| 18 | rs36430570 | 64483193 | 56040379 | 73752885 | G | A | 0.741 | 8.932803 | 1.17E-09 | 111 | StrideCount;AngularVelocityVariance;AmplitudeTailBase;AmplitudeTailBaseVariance;LimbDutyVariance;AmplitudeNose;AmplitudeNoseVariance;StepLengthVariance;StepWidthVariance;StrideLength;TemporalSymmetry;TemporalSymmetryVariance;AmplitudeTailTip;AmplitudeTailTipVariance |
| 18 | rs51201458 | 65216086 | 57062888 | 75007619 | G | A | 0.394 | 6.706893 | 1.96E-07 | 117 | StrideCount;AngularVelocityVariance;AmplitudeTailBase;AmplitudeTailBaseVariance;LimbDutyVariance;AmplitudeNose;AmplitudeNoseVariance;StepLengthVariance;StepWidthVariance;StrideLength;TemporalSymmetry;TemporalSymmetryVariance;AmplitudeTailTip;AmplitudeTailTipVariance |
| 18 | rs29726495 | 65393282 | 57725240 | 68139867 | G | C | 0.3 | 6.84791 | 1.42E-07 | 84 | StrideCount;AngularVelocityVariance;AmplitudeTailBase;AmplitudeTailBaseVariance;LimbDutyVariance;AmplitudeNose;AmplitudeNoseVariance;StepLengthVariance;StrideLength;TemporalSymmetry;TemporalSymmetryVariance;AmplitudeTailTip;AmplitudeTailTipVariance |
| 18 | rs30054945 | 70411857 | 61971281 | 77271975 | T | A | 0.41 | 5.065658 | 8.60E-06 | 88 | StrideCount;AngularVelocityVariance;AmplitudeTailBase;AmplitudeTailBaseVariance;LimbDutyVariance;AmplitudeNose;StepLengthVariance;StepWidthVariance;StrideLength;StrideLengthVariance;TemporalSymmetry;TemporalSymmetryVariance;AmplitudeTailTip;AmplitudeTailTipVariance |

FIG. 22 continued

| | | | | | | | | | | | |
|---|---|---|---|---|---|---|---|---|---|---|---|
| 18 | rs48505900 | 70577163 | 63513573 | 70627094 | G | A | 0.156 | 4.859087 | 1.38E-05 | 48 | StrideCount;AngularVelocityVariance;AmplitudeTailBase;AmplitudeTailBaseVariance;LimbDutyVariance;AmplitudeNose;StepLengthVariance;StepWidthVariance;StrideLength;TemporalSymmetry;TemporalSymmetryVariance;AmplitudeTailTip |
| 18 | rs45931146 | 71509534 | 65439944 | 81477550 | G | C | 0.28 | 5.584 | 2.61E-06 | 93 | AngularVelocityVariance;AmplitudeTailBase;AmplitudeTailBaseVariance;LimbDutyVariance;AmplitudeNose;StepWidthVariance;StrideLength;StrideLengthVariance;TemporalSymmetry;TemporalSymmetryVariance;AmplitudeTailTip;AmplitudeTailTipVariance |
| 18 | rs29560075 | 74878171 | 67992722 | 83749998 | T | C | 0.223 | 11.7642 | 1.72E-12 | 72 | AngularVelocityVariance;AmplitudeTailBaseVariance;LimbDutyVariance;AmplitudeNose;StepWidthVariance;StrideLengthVariance;TemporalSymmetry;TemporalSymmetryVariance;AmplitudeTailTipVariance |
| 18 | rs37644625 | 75328048 | 68502982 | 75328048 | T | C | 0.077 | 6.515239 | 3.05E-07 | 27 | AmplitudeTailBaseVariance;LimbDutyVariance;AmplitudeNose;StepWidthVariance;StrideLengthVariance;TemporalSymmetry;TemporalSymmetryVariance |
| 18 | rs36251472 | 75704173 | 65777372 | 85664893 | G | A | 0.331 | 6.967644 | 1.08E-07 | 104 | AngularVelocityVariance;AmplitudeTailBaseVariance;LimbDutyVariance;AmplitudeNose;StepWidthVariance;StrideLength;StrideLengthVariance;TemporalSymmetry;TemporalSymmetryVariance;AmplitudeTailTipVariance |
| 19 | rs36528579 | 15920929 | 5955148 | 24379866 | G | A | 0.521 | 4.789537 | 1.62E-05 | 285 | AngularVelocityVariance;LimbDuty;LimbDutyVariance;AmplitudeNoseVariance;StepWidth;StepWidthVariance;StrideLengthVariance;TemporalSymmetry;TemporalSymmetryVariance |

FIG. 22 continued

| | | | | | | | | | | | |
|---|---|---|---|---|---|---|---|---|---|---|---|
| 19 | rs36954426 | 16641784 | 10466337 | 25008613 | T | C | 0.072 | 8.907239 | 1.24E-09 | 172 | AngularVelocityVariance;LimbDuty;LimbDutyVariance;AmplitudeNoseVariance;StepWidth;StepWidthVariance;StrideLengthVariance;TemporalSymmetry;TemporalSymmetryVariance |
| 19 | rs37430865 | 19203540 | 15297820 | 23376216 | T | C | 0.751 | 5.170084 | 6.76E-06 | 29 | AngularVelocityVariance;LimbDuty;LimbDutyVariance;AmplitudeNoseVariance;StepWidth;StepWidthVariance;StrideLengthVariance;TemporalSymmetry;TemporalSymmetryVariance |
| 19 | rs49815821 | 19753183 | 16063270 | 26731527 | T | C | 0.897 | 5.659287 | 2.19E-06 | 46 | AngularVelocityVariance;LimbDuty;LimbDutyVariance;AmplitudeNoseVariance;StepWidthVariance;StrideLengthVariance;TemporalSymmetry;TemporalSymmetryVariance |
| 19 | rs49721453 | 20547056 | 16882375 | 27178781 | T | C | 0.763 | 5.28326 | 5.21E-06 | 43 | AngularVelocityVariance;LimbDuty;AmplitudeNoseVariance;StepWidthVariance;StrideLengthVariance;TemporalSymmetry;TemporalSymmetryVariance |
| 19 | rs47772749 | 20974497 | 13819664 | 28816217 | C | A | 0.098 | 15.49383 | 3.21E-16 | 61 | AngularVelocityVariance;LimbDuty;LimbDutyVariance;AmplitudeNoseVariance;StepWidth;StepWidthVariance;StrideLengthVariance;TemporalSymmetry;TemporalSymmetryVariance |
| 19 | rs36255152 | 21156644 | 12802559 | 24704117 | C | A | 0.099 | 4.812539 | 1.54E-05 | 84 | AngularVelocityVariance;LimbDuty;LimbDutyVariance;AmplitudeNoseVariance;StepWidth;StepWidthVariance;StrideLengthVariance;TemporalSymmetry;TemporalSymmetryVariance |
| 19 | rs36521179 | 41688939 | 34435990 | 50459206 | G | A | 0.103 | 5.348407 | 4.48E-06 | 185 | AngularVelocityVariance;TemporalSymmetryVariance |
| 19 | rs37124448 | 41732752 | 32775347 | 51384614 | T | C | 0.862 | 5.383099 | 4.14E-06 | 199 | AngularVelocityVariance;TemporalSymmetryVariance |
| 19 | rs30419213 | 55474602 | 45479657 | 61261300 | T | A | 0.695 | 7.10042 | 7.94E-08 | 118 | AngularVelocityVariance;AmplitudeTailBaseVariance;AmplitudeNose;AmplitudeNoseVariance;StrideLengthVariance;AmplitudeTailTipVariance |
| 19 | rs48127753 | 60857703 | 51016990 | 61140081 | T | C | 0.205 | 5.159734 | 6.92E-06 | 61 | AngularVelocityVariance;AmplitudeTailBaseVariance;AmplitudeNose;AmplitudeNoseVariance;StrideLengthVariance;AmplitudeTailTipVariance |

FIG. 22 continued

| | | | | | | | | | | | |
|---|---|---|---|---|---|---|---|---|---|---|---|
| X | rs33267035 | 5499679 | 5499679 | 5685659 | G | A | 0.623 | 5.810697 | 1.55E-06 | 1 | StrideLength |
| X | rs33299759 | 6416711 | 6416711 | 7970889 | T | G | 0.911 | 18.07233 | 8.47E-19 | 33 | LimbDutyVariance;StepWidthVariance |
| X | rs33306146 | 6653690 | 6653690 | 11852163 | G | A | 0.924 | 4.816246 | 1.53E-05 | 87 | DistanceTraveled;LimbDutyVariance;StepLength;StepWidth;StepWidthVariance;StrideLength;StrideLengthVariance;TemporalSymmetryVariance |
| X | rs33393875 | 8247714 | 8247714 | 11206714 | T | C | 0.907 | 11.94645 | 1.13E-12 | 37 | DistanceTraveled;LimbDutyVariance;StepLength;StepWidth;StepWidthVariance;StrideLength;StrideLengthVariance;TemporalSymmetryVariance |
| X | rs31351762 | 10259365 | 9582564 | 12671555 | G | A | 0.51 | 9.769273 | 1.70E-10 | 22 | StepLength;StepWidth;StrideLength |
| X | rs29855684 | 38577202 | 38335621 | 48379547 | G | C | 0.075 | 9.963 | 1.09E-10 | 28 | LimbDutyVariance;StepLength;StepWidth;StrideLength |
| X | rs30131968 | 47751136 | 47609127 | 49069245 | G | A | 0.556 | 11.54335 | 2.86E-12 | 17 | LimbDutyVariance;StepLength;StrideLength;AmplitudeTailTip |
| X | rs30181470 | 48802212 | 48802212 | 48802212 | C | A | 0.092 | 9.014081 | 9.68E-10 | NA | StepLength;StrideLength |
| X | rs31364910 | 49231624 | 48448266 | 59024738 | T | A | 0.243 | 7.946553 | 1.13E-08 | 66 | AngularVelocityVariance;StepLength;StepWidth;StepWidthVariance;StrideLength;StrideLengthVariance;AmplitudeTailTip |
| X | rs3667254 | 50678357 | 50678357 | 50730575 | T | A | 0.776 | 7.411901 | 3.87E-08 | NA | StrideLength;AmplitudeTailTip |
| X | rs30325286 | 51778462 | 51778462 | 51887299 | G | A | 0.234 | 7.967495 | 1.08E-08 | 1 | StepLength;StrideLength;AmplitudeTailTip |
| X | rs30368366 | 52411391 | 51898123 | 59479322 | T | C | 0.737 | 9.572435 | 2.68E-10 | 45 | AngularVelocityVariance;StepLength;StepWidth;StrideLength;StrideLengthVariance;AmplitudeTailTip |
| X | rs30426904 | 53089031 | 53089031 | 53089031 | C | A | 0.203 | 6.612245 | 2.44E-07 | 1 | StrideLength;AmplitudeTailTip |
| X | rs29116718 | 55849810 | 55849810 | 56762966 | T | C | 0.292 | 5.301339 | 5.00E-06 | 10 | AmplitudeTailTip |
| X | rs29060797 | 58156097 | 51112225 | 68126383 | T | G | 0.499 | 8.071683 | 8.48E-09 | 66 | AngularVelocityVariance;StepLength;StepWidth;StrideLength;StrideLengthVariance;AmplitudeTailTip |
| X | rs29059271 | 58446963 | 58446963 | 58446963 | T | C | 0.804 | 8.634321 | 2.32E-09 | NA | AngularVelocityVariance;StepLength;StrideLength;StrideLengthVariance |
| X | rs29055062 | 61830222 | 61830222 | 61830222 | G | A | 0.734 | 7.225472 | 5.95E-08 | NA | StrideLength;AmplitudeTailTip |
| X | rs29052980 | 62862435 | 62862435 | 64161107 | T | G | 0.555 | 5.774446 | 1.68E-06 | 1 | StrideLength;AmplitudeTailTip |
| X | rs13483786 | 64615642 | 64615642 | 65450873 | C | A | 0.505 | 5.702378 | 1.98E-06 | 1 | AmplitudeTailTip |
| X | rs29043964 | 69266803 | 60256642 | 69683516 | T | C | 0.692 | 8.004568 | 9.90E-09 | 21 | StepLength;StrideLength;AmplitudeTailTip |
| X | rs29040622 | 72384270 | 62396060 | 72530856 | T | C | 0.526 | 5.599758 | 2.51E-06 | 34 | StepLength;StrideLength;AmplitudeTailTip |

FIG. 22 continued

| | | | | | | | | | | | |
|---|---|---|---|---|---|---|---|---|---|---|---|
| X | rs29035802 | 75917865 | 65974073 | 85883993 | T | C | 0.722 | 7.928052 | 1.18E-08 | 135 | AmplitudeTailBase;LimbDutyVariance;StepLength;StepWidth;StepWidthVariance;StrideLength;StrideLengthVariance;TemporalSymmetryVariance;AmplitudeTailTip |
| X | rs29032033 | 76178554 | 76178554 | 84003257 | G | C | 0.437 | 6.283945 | 5.20E-07 | 21 | LimbDutyVariance;StepLength;StepWidth;StepWidthVariance;StrideLength;StrideLengthVariance;TemporalSymmetryVariance;AmplitudeTailTip |
| X | rs3659975 | 77065449 | 77065449 | 77065449 | G | A | 0.689 | 5.679323 | 2.09E-06 | NA | StrideLength;AmplitudeTailTip |
| X | rs29031554 | 78703262 | 69232896 | 81075935 | G | A | 0.925 | 11.49582 | 3.19E-12 | 119 | AmplitudeTailBase;LimbDutyVariance;StepLength;StepWidth;StepWidthVariance;StrideLength;StrideLengthVariance;TemporalSymmetryVariance;AmplitudeTailTip |
| X | rs29066669 | 86323418 | 76621306 | 88527250 | T | C | 0.468 | 6.828481 | 1.48E-07 | 26 | LimbDutyVariance;StepLength;StepWidth;StepWidthVariance;StrideLength;StrideLengthVariance;TemporalSymmetryVariance;AmplitudeTailTip |
| X | rs29066573 | 86919754 | 77105278 | 90882720 | G | C | 0.775 | 7.25551 | 5.55E-08 | 29 | LimbDutyVariance;StepLength;StepWidth;StepWidthVariance;StrideLength;TemporalSymmetryVariance;AmplitudeTailTip |
| X | rs29071883 | 92685669 | 85002760 | 1.02E+08 | G | C | 0.447 | 7.433616 | 3.68E-08 | 85 | LimbDutyVariance;StepWidthVariance;StrideLength;AmplitudeTailTip |
| X | rs13483891 | 95903369 | 95903369 | 1.01E+08 | C | A | 0.442 | 4.852711 | 1.40E-05 | 31 | LimbDutyVariance;StepWidthVariance;AmplitudeTailTip |
| X | rs31832285 | 100897243 | 1.01E+08 | 1.02E+08 | C | A | 0.087 | 8.184301 | 6.54E-09 | 24 | LimbDutyVariance;StepWidthVariance;AmplitudeTailTip |
| X | rs29081428 | 103232846 | 1.03E+08 | 1.03E+08 | T | C | 0.075 | 11.49582 | 3.19E-12 | NA | StepLength;StepWidth;StrideLength |
| X | rs29079803 | 104140953 | 1.04E+08 | 1.04E+08 | T | C | 0.199 | 10.42377 | 3.77E-11 | 1 | DistanceTraveled;AngularVelocityVariance;StrideLength;StrideLengthVariance |
| X | rs29078218 | 105681574 | 99051769 | 1.06E+08 | T | A | 0.377 | 6.55778 | 2.77E-07 | 68 | DistanceTraveled;AngularVelocityVariance;LimbDutyVariance;StepLength;StepWidth;StepWidthVariance;StrideLength;StrideLengthVariance;AmplitudeTailTip |
| X | rs33877320 | 105962632 | 1.06E+08 | 1.06E+08 | T | C | 0.436 | 5.890358 | 1.29E-06 | 3 | StrideLength;AmplitudeTailTip |

FIG. 22 continued

| | | | | | | | | | | | |
|---|---|---|---|---|---|---|---|---|---|---|---|
| X | rs29092747 | 108506054 | 99227885 | 1.12E+08 | T | C | 0.243 | 7.047237 | 8.97E-08 | 96 | DistanceTraveled;AngularVelocityVariance;LimbDutyVariance;StepLength;StepWidth;StepWidthVariance;StrideLength;StrideLengthVariance;AmplitudeTailTip |
| X | rs29092740 | 108621203 | 1.07E+08 | 1.14E+08 | T | A | 0.923 | 8.719104 | 1.91E-09 | 28 | StepLength;StrideLength;AmplitudeTailTip |
| X | rs29105711 | 115987986 | 1.16E+08 | 1.16E+08 | T | C | 0.206 | 6.648288 | 2.25E-07 | NA | StrideLength;AmplitudeTailTip |
| X | rs29103983 | 116871170 | 1.1E+08 | 1.27E+08 | G | A | 0.488 | 8.910162 | 1.23E-09 | 32 | AngularVelocityVariance;AmplitudeTailBase;StepLength;StrideLength;StrideLengthVariance;AmplitudeTailTip |
| X | rs29107230 | 122283365 | 1.22E+08 | 1.22E+08 | G | A | 0.117 | 7.981285 | 1.04E-08 | NA | AngularVelocityVariance;StepLength;StrideLength;StrideLengthVariance |
| X | rs29114868 | 130288103 | 1.3E+08 | 1.3E+08 | G | A | 0.792 | 6.776963 | 1.67E-07 | 1 | StrideLength;AmplitudeTailTip |
| X | rs29115435 | 130506997 | 1.3E+08 | 1.39E+08 | C | A | 0.787 | 7.105585 | 7.84E-08 | 74 | StepLength;StepWidth;StepWidthVariance;StrideLength;AmplitudeTailTip;AmplitudeTailTipVariance |
| X | rs29114821 | 131092252 | 1.27E+08 | 1.32E+08 | T | G | 0.496 | 8.396526 | 4.01E-09 | 4 | StepLength;StrideLength;AmplitudeTailTip |
| X | rs29273601 | 131928937 | 1.32E+08 | 1.34E+08 | T | C | 0.175 | 8.798613 | 1.59E-09 | NA | StepLength;StrideLength;AmplitudeTailTip |
| X | rs29274796 | 131971761 | 1.27E+08 | 1.33E+08 | G | A | 0.65 | 6.09288 | 8.07E-07 | 3 | StepLength;StrideLength;AmplitudeTailTip |
| X | rs29270985 | 133734147 | 1.34E+08 | 1.41E+08 | T | G | 0.278 | 7.028132 | 9.37E-08 | 94 | StepLength;StepWidth;StepWidthVariance;StrideLength;AmplitudeTailTip;AmplitudeTailTipVariance |
| X | rs29265976 | 135798945 | 1.34E+08 | 1.41E+08 | T | C | 0.625 | 9.668979 | 2.14E-10 | 94 | StepLength;StepWidth;StepWidthVariance;StrideLength;AmplitudeTailTip;AmplitudeTailTipVariance |
| X | rs29264170 | 136596781 | 1.36E+08 | 1.41E+08 | T | C | 0.435 | 6.172741 | 6.72E-07 | 38 | StrideLength;AmplitudeTailTip;AmplitudeTailTipVariance |
| X | rs29256169 | 140696912 | 1.38E+08 | 1.42E+08 | G | C | 0.384 | 5.048788 | 8.94E-06 | 30 | StrideLength;AmplitudeTailTip |
| X | rs29288776 | 141181918 | 1.41E+08 | 1.41E+08 | T | C | 0.239 | 6.639778 | 2.29E-07 | 7 | StrideLength;AmplitudeTailTip |
| X | rs29289031 | 142111113 | 1.37E+08 | 1.44E+08 | T | G | 0.179 | 9.024787 | 9.45E-10 | 48 | LimbDutyVariance;StepLength;StrideLength;TemporalSymmetryVariance;AmplitudeTailTip |
| X | rs29279837 | 145498175 | 1.44E+08 | 1.54E+08 | G | A | 0.84 | 6.084613 | 8.23E-07 | 54 | LimbDutyVariance;StepLength;StepWidthVariance;StrideLength;AmplitudeTailTip |

FIG. 22 continued

| | | | | | | | | | | | |
|---|---|---|---|---|---|---|---|---|---|---|---|
| X | rs29276505 | 146887038 | 1.39E+08 | 1.57E+08 | G | A | 0.381 | 10.85737 | 1.39E-11 | 112 | LimbDutyVariance;StepLength;StepWidth;StepWidthVariance;StrideLength;TemporalSymmetryVariance;AmplitudeTailTip |
| X | rs29292574 | 152670879 | 1.43E+08 | 1.53E+08 | C | A | 0.469 | 5.480189 | 3.31E-06 | 53 | LimbDutyVariance;StepLength;StepWidthVariance;StrideLength;AmplitudeTailTip |
| X | rs29292272 | 152986021 | 1.52E+08 | 1.53E+08 | G | A | 0.923 | 9.048902 | 8.94E-10 | 9 | StepLength;StrideLength;AmplitudeTailTip |
| X | rs29291411 | 153558225 | 1.44E+08 | 1.54E+08 | G | A | 0.732 | 6.823561 | 1.50E-07 | 53 | LimbDutyVariance;StepLength;StepWidthVariance;StrideLength;AmplitudeTailTip |
| X | rs29309642 | 159218203 | 1.57E+08 | 1.64E+08 | T | C | 0.145 | 7.691047 | 2.04E-08 | 35 | AmplitudeTailBase;AmplitudeTailTip |
| X | rs31411512 | 163784458 | 1.55E+08 | 1.64E+08 | T | C | 0.783 | 5.85816 | 1.39E-06 | 41 | AmplitudeTailBase;AmplitudeTailTip |
| X | rs31556818 | 166348315 | 1.64E+08 | 1.66E+08 | G | A | 0.236 | 7.442562 | 3.61E-08 | 14 | StrideLength;AmplitudeTailTip |
| X | rs31640630 | 167176755 | 1.57E+08 | 1.68E+08 | T | A | 0.089 | 18.07233 | 8.47E-19 | 59 | AmplitudeTailBase;LimbDutyVariance;StepWidthVariance;StrideLength;AmplitudeTailTip |
| X | rs13484112 | 168827808 | 1.69E+08 | 1.69E+08 | T | C | 0.149 | 10.55678 | 2.77E-11 | 1 | StepLength;StrideLength |
| X | rs31788089 | 169323841 | 1.69E+08 | 1.69E+08 | T | C | 0.917 | 5.536526 | 2.91E-06 | 3 | StepLength;StepWidthVariance;StrideLength |

GAIT AND POSTURE ANALYSIS

REFERENCE TO RELATED APPLICATIONS

This application is a U.S. national phase application of International Patent Application no. PCT/US2021/065425, filed Dec. 29, 2021, which claims the benefit under 35 U.S.C. § 119(e) of U.S. Provisional application Ser. No. 63/144,052, filed Feb. 1, 2021, and U.S. Provisional application Ser. No. 63/131,498, filed Dec. 29, 2020, the disclosures of which are incorporated by reference herein in their entirety.

GOVERNMENT SUPPORT

This invention was made with government support under R21DA048634 and UM1OD023222 awarded by the National Institutes of Health. The government has certain rights in the invention.

FIELD OF THE INVENTION

The invention, in some aspects, relates to automated gait and posture analysis of subjects by processing video data.

BACKGROUND

In humans, the ability to quantitate gait and posture at high precision and sensitivity has shown that they can be used to determine proper function of numerous neural and muscular systems. Many psychiatric, neurodegenerative, and neuromuscular illnesses are associated with alterations in gait and posture, including autism spectrum disorder, schizophrenia, bipolar disorder, and Alzheimer's disease. This is because proper gait, balance, and posture are under the control of multiple nervous system processes, which include critical sensory centers that process visual, vestibular, auditory, proprioceptive, and visceral inputs. Regions of the brain that directly control movement, such as the cerebellum, motor cortex, and brain stem, respond to cognitive and emotionality cues. Thus, gait and posture integrity reflects proper neural functioning of many neural systems in humans. In rodent models of human psychiatric conditions, there has not been any demonstrated utility of gait and posture metrics as in humans. This may be due to the lack of readily implementable technology with sufficient accuracy to detect gait and posture differences between different mouse strains.

SUMMARY OF THE INVENTION

According to one aspect of the invention, a computer-implemented method is provided, the method including: receiving video data representing a video capturing movements of a subject; processing the video data to identify point data tracking movement, over a time period, of a set of body parts of the subject; determining, using the point data, a plurality of stance phases and a corresponding plurality of swing phases represented in the video data during the time period; determining, based on the plurality of stance phases and the plurality of swing phases, a plurality of stride intervals represented in the video data during the time period; determining, using the point data, metrics data for the subject, the metrics data being based on each stride interval of the plurality of stride intervals; comparing the metrics data for the subject to control metrics data; and determining, based on the comparing, a difference between the subject's metrics data and the control metrics data. In certain embodiments, the set of body parts includes the nose, base of neck, mid spine, left hind paw, right hind paw, base of tail, middle of tail and tip of tail; and wherein the plurality of stance phases and the plurality of swing phases are determined based on the change in movement speed of the left hind paw and the right hind paw. In certain embodiments, the method also includes determining a transition from a first stance phase of the plurality of stance phases and a first swing phase of the plurality of swing phases based on a toe-off event of the left hind paw or the right hind paw; and determining a transition from a second swing phase of the plurality of swing phases to a second stance phase of the plurality of stance phases based on a foot strike event of the left hind paw or the right hind paw. In some embodiments, the metrics data correspond to gait measurements of the subject during each stride interval. In some embodiments, the set of body parts includes a left hind paw and a right hind paw, and wherein determining the metrics data includes: determining, using the point data, a step length for each stride interval, the step length representing a distance that the right hind paw travels past a previous left hind paw strike; determining, using the point data, a stride length using for the each stride interval, the stride length representing a distance that the left hind paw travels during the each stride interval; between the left forepaw and the left hind paw for the each stride interval from a toe-off event to a foot-strike event; determining, using the point data, a step width for the each stride interval, the step width representing a distance between the left hind paw and the right hind paw. In some embodiments, the set of body parts includes a tail base, and wherein determining the metrics data includes determining, using the point data, speed data of the subject based on movement of the tail base for the each stride interval. In certain embodiments, the set of body parts includes a tail base, and wherein determining the metrics data includes: determining, using the point data, a set of speed data of the subject based on movement of the tail base during a set of frames representing a stride interval of the plurality of stride intervals; and determining a stride speed, for the stride interval, by averaging the set of speed data. In some embodiments, the set of body parts includes a right hind paw and a left hind paw, and wherein determining the metrics data includes: determining, using the point data, first stance duration representing an amount of time that the right hind paw is in contact with ground during a stride interval of the plurality of stride intervals; determining a first duty factor based on the first stance duration and the duration of the stride interval; determining, using the point data, second stance duration representing an amount of time that the left hind paw is in contact with ground during the stride interval; determining a second duty factor based on the second stance duration and the duration of the stride interval; and determining an average duty factor for the stride interval based on the first duty factor and the second duty factor. In some embodiments, the set of body parts includes a tail base and a neck base, and wherein determining the metrics data includes: determining, using the point data, a set of vectors connecting the tail base and the neck base during a set of frames representing a stride interval of the plurality of stride intervals; and determining, using the set of vectors, an angular velocity of the subject for the stride interval. In certain embodiments, the metrics data correspond to posture measurements of the subject during each stride interval. In some embodiments, the set of body parts includes a spine center of the subject, wherein a stride interval of the plurality of stride intervals is associated with a set of frames of the video data, and wherein determining the metrics data includes determining, using the point data, a displacement vector for the stride interval, the displacement vector connecting the spine center represented in a first frame of the set of frames and the spine center represented in a last frame of the set of frames. In some embodiments, the set of body parts further includes a nose of the subject, and wherein determining the metrics data includes determining, using the point data, a set of lateral displacements of the nose for the stride interval based on a perpendicular distance of the nose from the displacement vector for each frame in the set of frames. In certain embodiments, the lateral displacement of the nose is further based on a body length of the subject. In some embodiments, determining the metrics data further includes determining a tail tip displacement phase offset by: performing an interpolation using the set of lateral displacements of the nose to generate a smooth curve lateral displacement of the nose for the stride interval; determining, using the smooth curve lateral displacement of the nose, when a maximum displacement of the nose occurs during the stride interval; and determining a percent stride location representing a percent of the stride interval that is completed when the maximum displacement of the nose occurs. In some embodiments, the set of body parts further includes a tail base of the subject, and wherein determining the metrics data includes: determining, using the point data, a set of lateral displacements of the tail base for the stride interval based on a perpendicular distance of the tail base from the displacement vector for each frame in the set of frames. In some embodiments, determining the metrics data further includes determining a tail base displacement phase offset by: performing an interpolation using the set of lateral displacements of the tail base to generate a smooth curve lateral displacement of the tail base for the stride interval; determining, using the smooth curve lateral displacement of the tail base, when a maximum displacement of the tail base occurs during the stride interval; and determining a percent stride location representing a percent of the stride interval that is completed when the maximum displacement of the tail base occurs. In certain embodiments, the set of body parts also includes a tail tip of the subject, and wherein determining the metrics data includes: determining, using the point data, a set of lateral displacements of the tail tip for the stride interval based on a perpendicular distance of the tail tip from the displacement vector for each frame in the set of frames. In some embodiments, determining the metrics data also includes determining a tail tip displacement phase offset by: performing an interpolation using the set of lateral displacements of the tail tip to generate a smooth curve lateral displacement of the tail tip for the stride interval; determining, using the smooth curve lateral displacement of the tail tip, when a maximum displacement of the tail tip occurs during the stride interval; and determining a percent stride location representing a percent of the stride interval that is completed when the maximum displacement of the tail tip occurs. In some embodiments, processing the video data includes processing the video data using a machine-learning model. In certain embodiments, processing the video data includes processing the video data using a neural network model. In certain embodiments, the video captures subject-determined movements of the subject in an open arena with a top-down view. In some embodiments, the control metrics data is obtained from a control organism or plurality thereof. In some embodiments, the subject is an organism and the control organism and the subject organism are the same species. In certain embodiments, the species is a member of the Order Rodentia, and optionally is rat or mouse. In certain embodiments, the control organism is a laboratory strain of the species. In some embodiments, the laboratory strain is one listed in FIG. 14E. In some embodiments, a statistically significant difference in the subject's metrics data compared to the control metrics data indicates a difference in the phenotype of the subject compared to the phenotype of the control organism. In some embodiments, the phenotypic difference indicates the presence of a disease or condition in the subject. In certain embodiments, the phenotypic difference indicates a difference between the genetic background of the subject and the genetic background of the control organism. In some embodiments, a statistically significant difference in the subject's metrics data and the control metrics data indicates a difference in the genotype of the subject compared to the genotype of the control organism. In certain embodiments, the difference in the genotype indicates a strain difference between the subject and the control organism. In certain embodiments, the difference in the genotype indicates the presence of a disease or condition in the subject. In some embodiments, the disease or condition is Rett syndrome, Down syndrome, amyotrophic lateral sclerosis (ALS), autism spectrum disorder (ASD), schizophrenia, bipolar disorder, a neurodegenerative disorder, dementia, or a brain injury. In some embodiments, the control organism and the subject organism are the same gender. In certain embodiments, the control organism and the subject organism are not the same gender. In some embodiments, the control metrics data corresponds to elements including: control stride length, control step length and control step width, wherein the subject's metrics data includes elements including stride lengths for the subject during the time period, step lengths for the subject during the time period and step widths for the subject during the time period, and wherein the difference between the one or more of the elements of the control data and the metrics data is indicative of a phenotypic difference between the subject and the control.

According to another aspect of the invention, methods of assessing one or more of an activity and behavior of a subject known to have, suspected of having, or at risk of having a disease or condition, are provided, the method including: obtaining metrics data for the subject, wherein a means for the obtaining comprises a computer-generated method of any embodiment of an aforementioned method or system of the invention, and based at least in part on the obtained metrics data, determining presence or absence of the disease or condition. In some embodiments the method also includes selecting a therapeutic regimen for the subject, based at least in part on the determined presence of the disease or condition. In some embodiments, the method also includes administering the selected therapeutic regimen to the subject. In some embodiments, the method also includes obtaining the metrics data for the subject at a time subsequent to the administration of the therapeutic regimen, and optionally comparing the initial obtained metrics data and the subsequent obtained metrics data and determining efficacy of the administered therapeutic regimen. In some embodiments, the method also includes repeating, increasing, or decreasing administration of the selected therapeutic regimen to the subject, based at least in part on the comparison of the initial and subsequent metrics data obtained for the subject. In some embodiments, the method also includes comparing the obtained metrics data to control metrics data. In some embodiments the disease or condition is: a neurodegenerative disorder, neuromuscular disorder, neuropsychiatric disorder, ALS, autism, Down syndrome, Rett syndrome, bipolar disorder, dementia, depression, a hyperkinetic disorder, an anxiety disorder, a developmental disorder, a sleep disorder, Alzheimer's disease, Parkinson's disease, a physical injury, etc. Additional diseases and disorders and animal models that can be assessed using a method and/or system of the invention are known in the art, see for example: Barrot M. Neuroscience 2012; 211: 39-50; Graham, D. M., Lab Anim (NY) 2016; 45: 99-101; Sewell, R. D. E., Ann Transl Med 2018; 6: S42. 2019 Jan. 8; and Jourdan, D., et al., Pharmacol Res 2001; 43: 103-110.

According to another aspect of the invention, a method of identifying a subject as an animal model for a disease or condition is provided, the method including obtaining metrics data for the subject, wherein a means for the obtaining comprises a computer-generated method of any one embodiment of an aforementioned method or system of the invention, and based at least in part on the obtained metrics data, determining one or more characteristics of the disease or condition in the subject, wherein the presence of the one or more characteristics of the disease or condition in the subject, identifies the subject as an animal model for the disease or condition. In some embodiments, the method also includes additional assessment of the subject. In some embodiments the disease or condition is: a neurodegenerative disorder, neuromuscular disorder, neuropsychiatric disorder, ALS, autism, Down syndrome, Rett syndrome, bipolar disorder, dementia, depression, a hyperkinetic disorder, an anxiety disorder, a developmental disorder, a sleep disorder, Alzheimer's disease, Parkinson's disease, a physical injury, etc. In some embodiments, the method also includes comparing the obtained metrics data to a control metrics data, and identifying one or more similarities a similarity or differences in the obtained metrics data and the control metrics data, wherein identified similarities or differences assist in identifying the subject as an animal model for the disease or condition.

According to another aspect of the invention, a method of determining the presence of an effect of a candidate compound on a disease or condition is provided, the method including: obtaining first metrics data for a subject, wherein a means for the obtaining includes a computer-generated method of any embodiment of the aforementioned computer generated aspect of the invention, and wherein the subject has the disease or condition or is an animal model for the disease or condition; administering to the subject the candidate compound; obtaining post-administration metrics data for the organism; comparing the first and post-administration metrics data, wherein a difference in the first and post-administration metrics data identifies an effect of the candidate compound on the disease or condition. In some embodiments, the method also includes additional testing of the compound's effect in treatment of the disease or condition.

According to another aspect of the invention, a method of identifying the presence of an effect of a candidate compound on a disease or condition is provided, the method including: administering the candidate compound to a subject that has the disease or condition or that is an animal model for the disease or condition; obtaining metrics data for the subject, wherein a means for the obtaining includes a computer-generated method of any embodiment of the aforementioned computer generated aspect of the invention; comparing the obtained metrics data to a control metrics data, wherein a difference in the obtained metrics data and the control metrics data identifies the presence of an effect of the candidate compound on the disease or condition.

According to another aspect of the invention, a system is provided, the system including: at least one processor; and at least one memory comprising instructions that, when executed by the at least one processor, cause the system to: receive video data representing a video capturing movements of a subject; processing the video data to identify point data tracking movement, over a time period, of a set of body parts of the subject; determine, using the point data, a plurality of stance phases and a corresponding plurality of swing phases represented in the video data during the time period; determine, based on the plurality of stance phases and the plurality of swing phases, a plurality of stride intervals represented in the video data during the time period; determine, using the point data, metrics data for the subject, the metrics data being based on each stride interval of the plurality of stride intervals; compare the metrics data for the subject to control metrics data; and determine, based on the comparing, a difference between the subject's metrics data and the control metrics data. In some embodiments, the set of body parts includes the nose, base of neck, mid spine, left hind paw, right hind paw, base of tail, middle of tail and tip of tail; and wherein the plurality of stance phases and the plurality of swing phases are determined based on the change in movement speed of the left hind paw and the right hind paw. In certain embodiments, the at least one memory also includes instructions that, when executed by the at least one processor, further cause the system to: determine a transition from a first stance phase of the plurality of stance phases and a first swing phase of the plurality of swing phases based on a toe-off event of the left hind paw or the right hind paw; and determine a transition from a second swing phase of the plurality of swing phases to a second stance phase of the plurality of stance phases based on a foot strike event of the left hind paw or the right hind paw. In certain embodiments, the metrics data correspond to gait measurements of the subject during each stride interval. In some embodiments, the set of body parts includes a left hind paw and a right hind paw, and wherein the instruction that causes the system to determine the metrics data further causes the system to: determine, using the point data, a step length for each stride interval, the step length representing a distance that the right hind paw travels past a previous left hind paw strike; determine, using the point data, a stride length using for the each stride interval, the stride length representing a distance that the left hind paw travels during the each stride interval; determine, using the point data, a step width for the each stride interval, the step width representing a distance between the left hind paw and the right hind paw. In some embodiments, the set of body parts includes a tail base, and wherein the instruction that causes the system to determine the metrics data further causes the system to: determine, using the point data, speed data of the subject based on movement of the tail base for the each stride interval. In certain embodiments, the set of body parts includes a tail base, and wherein the instruction that causes the system to determine the metrics data further causes the system to: determine, using the point data, a set of speed data of the subject based on movement of the tail base during a set of frames representing a stride interval of the plurality of stride intervals; and determine a stride speed, for the stride interval, by averaging the set of speed data. In certain embodiments, the set of body parts includes a right hind paw and a left hind paw, and wherein the instruction that causes the system to determine the metrics data further causes the system to: determine, using the point data, first stance duration representing an amount of time that the right hind paw is in contact with ground during a stride interval of the plurality of stride intervals; determine a first duty factor based on the first stance duration and the duration of the stride interval; determine, using the point data, second stance duration representing an amount of time that the left hind paw is in contact with ground during the stride interval; determine a second duty factor based on the second stance duration and the duration of the stride interval; and determine an average duty factor for the stride interval based on the first duty factor and the second duty factor. In some embodiments, the set of body parts includes a tail base and a neck base, and wherein the instruction that causes the system to determine the metrics data further causes the system to: determine, using the point data, a set of vectors connecting the tail base and the neck base during a set of frames representing a stride interval of the plurality of stride intervals; and determine, using the set of vectors, an angular velocity of the subject for the stride interval. In some embodiments, the metrics data correspond to posture measurements of the subject during each stride interval. In some embodiments, the set of body parts includes a spine center of the subject, wherein a stride interval of the plurality of stride intervals is associated with a set of frames of the video data, and wherein the instruction that causes the system to determine the metrics data further causes the system to determine, using the point data, a displacement vector for the stride interval, the displacement vector connecting the spine center represented in a first frame of the set of frames and the spine center represented in a last frame of the set of frames. In certain embodiments, the set of body parts also includes a nose of the subject, and wherein the instruction that causes the system to determine the metrics data further causes the system to: determine, using the point data, a set of lateral displacements of the nose for the stride interval based on a perpendicular distance of the nose from the displacement vector for each frame in the set of frames. In some embodiments, the lateral displacement of the nose is further based on a body length of the subject. In some embodiments, the instruction that causes the system to determine the metrics data further causes the system to determine a tail tip displacement phase offset by: performing an interpolation using the set of lateral displacements of the nose to generate a smooth curve lateral displacement of the nose for the stride interval; determining, using the smooth curve lateral displacement of the nose, when a maximum displacement of the nose occurs during the stride interval; and determining a percent stride location representing a percent of the stride interval that is completed when the maximum displacement of the nose occurs. In certain embodiments, the set of body parts also includes a tail base of the subject, and wherein the instruction that causes the system to determine the metrics data further causes the system to: determine, using the point data, a set of lateral displacements of the tail base for the stride interval based on a perpendicular distance of the tail base from the displacement vector for each frame in the set of frames. In some embodiments, the instruction that causes the system to determine the metrics data further causes the system to determine a tail base displacement phase offset by: performing an interpolation using the set of lateral displacements of the tail base to generate a smooth curve lateral displacement of the tail base for the stride interval; determining, using the smooth curve lateral displacement of the tail base, when a maximum displacement of the tail base occurs during the stride interval; and determining a percent stride location representing a percent of the stride interval that is completed when the maximum displacement of the tail base occurs. In certain embodiments, the set of body parts also includes a tail tip of the subject, and wherein the instruction that causes the system to determine the metrics data further causes the system to: determine, using the point data, a set of lateral displacements of the tail tip for the stride interval based on a perpendicular distance of the tail tip from the displacement vector for each frame in the set of frames. In some embodiments, the instruction that causes the system to determine the metrics data further causes the system to determine a tail tip displacement phase offset by: performing an interpolation using the set of lateral displacements of the tail tip to generate a smooth curve lateral displacement of the tail tip for the stride interval; determining, using the smooth curve lateral displacement of the tail tip, when a maximum displacement of the tail tip occurs during the stride interval; and determining a percent stride location representing a percent of the stride interval that is completed when the maximum displacement of the tail tip occurs. In certain embodiments, the instruction that causes the system to process the video data further causes the system to process the video data using a machine learning model. In some embodiments, the instruction that causes the system to process the video data further causes the system to process the video data using a neural network model. In some embodiments, the video captures subject-determined movements of the subject in an open arena with a top-down view. In certain embodiments, the control metrics data is obtained from a control organism or plurality thereof. In some embodiments, the subject is an organism and the control organism and the subject organism are the same species. In some embodiments, the species is a member of the Order Rodentia, and optionally is rat or mouse. In certain embodiments, the control organism is a laboratory strain of the species. In certain embodiments, the laboratory strain is one listed in FIG. 14E. In some embodiments, a statistically significant difference in the subject's metrics data compared to the control metrics data indicates a difference in the phenotype of the subject compared to the phenotype of the control organism. In some embodiments, the phenotypic difference indicates the presence of a disease or condition in the subject. In certain embodiments, the phenotypic difference indicates a difference between the genetic background of the subject and the genetic background of the control organism. In some embodiments, a statistically significant difference in the subject's metrics data and the control metrics data indicates a difference in the genotype of the subject compared to the genotype of the control organism. In some embodiments, the difference in the genotype indicates a strain difference between the subject and the control organism. In some embodiments, the difference in the genotype indicates the presence of a disease or condition in the subject. In certain embodiments, the disease or condition is Rett syndrome, Down syndrome, amyotrophic lateral sclerosis (ALS), autism spectrum disorder (ASD), schizophrenia, bipolar disorder, a neurodegenerative disorder, dementia, or a brain injury. In certain embodiments, the control organism and the subject organism are the same gender. In some embodiments, the control organism and the subject organism are not the same gender. In some embodiments, the control metrics data corresponds to elements including: control stride length, control step length and control step width, wherein the subject's metrics data includes elements including stride lengths for the subject during the time period, step lengths for the subject during the time period and step widths for the subject during the time period, and wherein the difference between the one or more of the elements of the control data and the metrics data is indicative of a phenotypic difference between the subject and the control.

BRIEF DESCRIPTION OF THE DRAWINGS

For a more complete understanding of the present disclosure, reference is now made to the following description taken in conjunction with the accompanying drawings.

FIG. 7A-C shows schematic diagrams and graphs illustrating a deep convolutional neural network for pose estimation. FIG. 7A shows HRNet-W32 neural network architecture for performing pose estimation. FIG. 7B shows the inference pipeline, which sends video, frames into the HRNet and generates twelve keypoint heatmaps as output. FIG. 7C presents training loss curves show network convergence without overfitting.

FIG. 8A-B shows spatial and temporal characteristics of gait (based on figure from Green et al., Dev Med Child Neurol (2009) 51:311). FIG. 8A is illustration showing how three spatial stride metrics were derived from hind paw foot strike positions: Step Length, Step Width and Stride Length. FIG. 8B is a Hildebrand Plot in which all metrics shown in this plot have percent stride time for units. This illustrates the relationship between foot strike and toe-off events with the stance and swing phases of stride. FIG. 8C shows a single frame of input video with hind paw tracks plotted fifty frames in the past and fifty frames in the future. The location of hind foot strike events is indicated with black circles. The outermost line of the three is the Hind Paw Right, the middle line of the three is the Tail Base, and the innermost line of the three is the Hind Paw Left. FIG. 8D-F shows three plots showing different aspects of the mouse's movement over the same one hundred-frame interval. The centered vertical line indicates the current frame (displayed in FIG. 8C). FIG. 8D shows three lines indicating speed of the left hind paw, the right hind paw, and the base of tail. The vertical dark lines in the plot indicate the inferred start frame of each stride. FIG. 8G illustrates the distribution of confidence values for each of the 12 points that were estimated. FIG. 8H provides an aggregate view of Hildebrand plot for hind paws binned according to angular velocity. FIG. 8I shows results similar to FIG. 8H except binned by speed. FIG. 8J illustrates that limb duty factor changes as a function of speed.

FIG. 9A-I provides schematic diagrams and graphs illustrating extraction of cyclic whole-body posture metrics during gait cycle. Several metrics relate to the cyclic lateral displacement observed in pose key points. The measures of lateral displacement were defined as an orthogonal offset from the relevant stride displacement vector. The displacement vector was defined as the line connecting the mouse's center of spine on the first frame of a stride to the mouse's center of spine on the last frame of stride. This offset was calculated at each frame of a stride and then a cubic interpolation was performed in order to generate a smooth displacement curve. The phase offset of displacement was defined as the percent stride location where maximum displacement occurs on this smoothed curve. The lateral displacement metric assigned to stride was the difference between maximum displacement value and minimum displacement value observed during a stride. Lateral displacement of (FIG. 9A) the tail tip and (FIG. 9B) the nose was measured. Displacement could also be averaged across many strides within a cohort to form a consensus view such as (FIG. 9D) C57BL/6J vs. (FIG. 9E) NOR/LtJ or many strides were averaged within individuals: (FIG. 9F) C57BL/6J vs. (FIG. 9G) NOR/LtJ. In FIG. 9H and FIG. 9I illustrate the diversity of lateral displacement between a set of strains selected from the strain survey. The light (translucent) bands for these two plots represent the 95% confidence interval of the mean for each respective strain.

FIG. 10A shows q-values (left) and effect sizes (right) obtained from a liner mixed effects model and circular-linear model adjusting for body length and age. In FIG. 10B Kernel density estimates and cumulative distribution functions of speed distributions were compared to test for differences in stride speeds between controls and mutants. In FIG. 10C total distance covered and speed were compared between controls and mutants using linear and linear mixed models respectively adjusting for body length and age. FIG. 10D illustrates results of body length adjusted gait metrics that were found to be different for linear mixed effects model. FIG. 10E shows results of lateral displacement of nose and tail tip for Ts65Dn strain. The solid lines represent the mean displacement of stride while the light (translucent) bands provides a 95% confidence interval for the mean.

FIG. 11A shows q-values (left) and effect sizes (right) that were obtained from model M1 for linear phenotypes and circular-linear models for circular phenotypes. FIG. 11B shows q-values (left) and effect sizes (right) obtained from model M3 for linear phenotypes and circular-linear models for circular phenotypes. In FIG. 11C, total distance covered were speed are compared between controls and mutants using linear and linear mixed models respectively adjusting for body length and age. In each pair shown, the left data is that of the control and the right data is that of the mutant. FIG. 11D shows body length adjusted gait metrics that were found to be different for linear mixed effects model. FIG. 11E illustrates use of the first two principal components to build a 2D representation of the multidimensional space in which controls and mutants are best separated. FIG. 11F shows cumulative distribution of speed in the ASD models. The upper curves are Controls and lower curves are Mutant. Cntnap2, Fmr1, Del4Aam have lower speed of strides, whereas Shank3 has higher stride speeds.

In FIG. 12A, each boxplot corresponds to a strain, with vertical position indicating residuals of stride length adjusted for body length. Strains are ordered by their median residual stride length value. FIG. 12B shows z-scores of body length adjusted gait metrics for all strains color coded by the cluster membership (see FIG. 12C). FIG. 12C shows use of K-means algorithm to build, using the first two principal components, a 2D representation of the multidimensional space in which strains are best separated. Top right region is cluster 1, lower region is cluster 2, and top left region shown is cluster 3. FIG. 12D provides a consensus view of lateral displacement of nose and tail tip across the clusters. The solid lines represent the mean displacement of stride while the translucent bands provides a 95% confidence interval for the mean. FIG. 12E are post-clustering plots summarizing the residual gait metrics across different clusters. In each set of three, left is cluster 1, middle is cluster 2, and right is cluster 3.

FIG. 13A provides heritability estimates for each phenotype mean (left) and variance (right). FIG. 13B-D provide Manhattan plots of all mean phenotypes (FIG. 13B), variance phenotypes (FIG. 13C), and all of them combined (FIG. 13D); colors correspond to the phenotype with the lowest p-value for the single nucleotide polymorphism (SNP).

FIG. 14A-D provides listings of animal strains used in certain implementations of the invention. FIG. 14A shows control strains and official identifies for gait mutants. FIG. 14B shows control strains and official identifiers for autism mutants. FIG. 14C shows a table summarizing body length and weight of animals in experiments. FIG. 14D provides a listing that summarizes animals used in the strain survey studies.

FIG. 15A is a heat map summarizing the effect sizes and q-values obtained from model M3: Phenotype~Genotype+TestAge+Speed+BodyLength+(1|MouseID/TestAge). FIG. 15B shows kernel density (left) and cumulative density (right) curves of speed across all strains. FIG. 15C is a plot showing positive association between body length and sex across different gait mutant strains. In each pair of results, Controls are on left of pair and Mutants are on right of pair. FIG. 15D shows body length (M1), speed (M2), body length and speed (M3) adjusted residuals for limb duty factor and step length for Mecp2 gait mutant. FIG. 15E shows body length (M1), speed (M2), body length and speed (M3) adjusted residuals for step width and stride length for Mecp2 gait mutant.

FIG. 16A is a heat map summarizing the effect sizes and q-values obtained from model M2: Phenotype~Genotype+TestAge+Speed+(1|MouseID/TestAge). FIG. 16B shows kernel density curves of speed across all strains. FIG. 16C is a plot showing positive association between body length and sex across different gait mutant strains. In each pair of results, Controls are on left of pair and Mutants are on right of pair. FIG. 16D shows body length (M1), speed (M2), body length and speed (M3) adjusted residuals for step length and stride length for Shank3 autism mutant. FIG. 16E shows body length (M1), speed (M2), body length and speed (M3) adjusted residuals for step length and stride length for Del4Aam autism mutant. In each pair of results shown Controls are on left of pair and Mutants are on right of pair.

FIG. 19 provides a listing summarizing effect sizes and FDR adjusted p-values obtained from models M1, M2, M3 for all phenotypes and gait strains.

FIG. 20 provides a listing summarizing effect sizes and FDR adjusted p-values obtained from models M1, M2, M3 for all phenotypes and autism strains FIG. 21A shows the majority indicated that there may be 2 or 3 clusters in the strain survey data. One major criterion for choosing the optimal number of clusters is to maximize the between-cluster distances while keeping the within-cluster distances small. To this end, within-sum-of-squares (WSS) was examined (shown in FIG. 21B); Caliński-Harabasz (CH) index shown in FIG. 21C) [Caliński, T. & Harabasz, Communications in Statistics-theory and Methods 3, 1-27 (1974)]; and gap statistic [Tibshirani, R. et al. Journal of the Royal Statistical Society: Series B (Statistical Methodology) 63, 411-423 (2001)] (shown in FIG. 21D) versus the number of clusters employed. All these indicated that 3 clusters is the optimal choice.

FIG. 22 shows a table of significant GWAS hits for gait and posture phenotypes. The information includes results of studies showing Quantitative Trait Loci (QTL) peak SNP, QTL peak SNP position, QTL start position, QTL end position Allele 1, Allele 2, Allele 1 frequency, p wald, protein coding genes, and groups in which the QTL was found to be significant.

DETAILED DESCRIPTION

Figure 1:
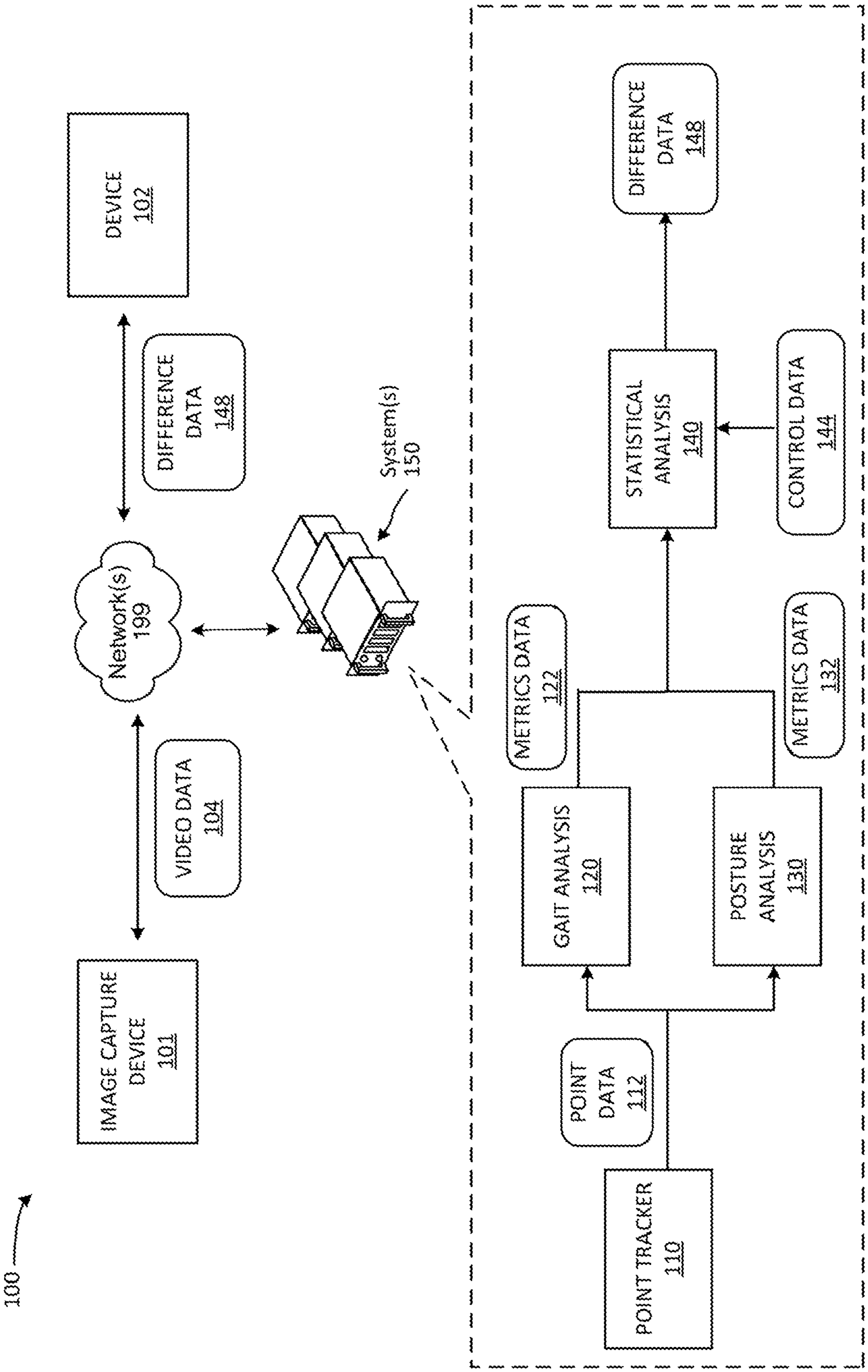
FIG. 1 is a conceptual diagram of an example system for determining subject gait and posture metrics, according to embodiments of the present disclosure.

The invention includes, in part, a method for processing video data to first track body parts of a subject, determine data representing gait metrics and posture metrics, and then performing statistical analysis to determine any differences/deviations from a control. Methods and systems of the invention provide a reliable and scalable automated system for extracting gait-level and posture-level features, and dramatically lowers time and labor costs associated with experiments for neurogenetics behavior and also reduces variability in such experiments.

Analysis of human and animal movement, including gait, has a storied past. Aristotle was the first to write a philosophical treatise on animal movement and gait using physical and metaphysical principles. During the Renaissance, Borelli applied the laws of physics and biomechanics to muscles, tendons, and joints of the entire body to understand gait. The first application of imaging technologies to the study of gait is credited to the work of Muybridge and Marey, who took sequential photographic images of humans and animals in motion in order to derive quantitative measurements of gait. Modern animal gait analysis methods are credited to Hildebrandt, who in the 1970s classified gait based on quantified metrics. He defined a gait cycle in terms of contact of limb to the ground (stance and swing phases). Fundamentally, this concept has not changed over the past 40 years: while current methods of mouse gait analysis have increased efficiency of the imaging approaches of Muybridge and Marey, they are fundamentally still based on the timing of limbs contacting the ground. This is in contrast to human gait and posture analysis, which, since the time of Borelli, has focused on body posture, and is akin to the quantitation of whole body movement rather than just contact with the ground. This difference between mouse and human is probably due in part to the difficulty in automatically estimating the posture of rodents, which appear as deformable objects due to their fur, which obscures joint positions. In addition, unlike humans, parts of mice cannot be easily marked with wearables for localization. In rodents, recent methods have made progress in determination of whole body coordination, however, these still require specialized equipment and force the animal to walk in a fixed direction in a corridor or treadmill or a narrow corridor for proper imaging and accurate determination of limb position. This is highly unnatural, and animals often require training to perform this behavior properly, limiting the use of this type of assay in correlating to human gait. Imaging from the side leads to perspective hurdles, which are overcome by limiting the movement of the animal to one depth field. Furthermore, as the animal defecates and urinates, or when bedding is present, the resulting occlusion makes long term monitoring from this perspective impractical. Indeed, ethologically relevant gait data in which animals can move freely often produce results that differ from treadmill-based assays. Furthermore, commercial treadmill- or corridor-based systems for gait analysis often produce a plethora of measures that show differing results with same animal models. The exact causes of these disparities are challenging to determine with closed, proprietary systems. Thus, there is currently a lack of an easily and broadly implementable tool to measure gait and posture in free-moving animals.

The open field assay is one of the oldest and most commonly used assays in behavioral neurogenetics. In rodents, it has classically been used to measure endophenotypes associated with emotionality, such as hyperactivity, anxiety, exploration, and habituation in rodents. For video-based open field assays, rich and complex behaviors of animal movement are abstracted to a simple point in order to extract behavioral measures. This oversimplified abstraction is necessary mainly due to technological limitations that have prohibited accurate extraction of complex poses from video data. New technology has the potential to overcome this limitation. Gait, an important indicator of neural function, is not typically analyzed, by conventional systems, in the open field mainly due to the technical difficulty of determining limb position when animals are moving freely. The ability to combine open field measures with gait and posture analysis would offer key insights into neural and genetic regulation of animal behavior in an ethologically relevant manner. The invention of the present disclosure leverages modern machine learning models, such as neural networks, to carry out subject gait and posture analysis in the open field. The invention relates to systems and methods to measure gait and whole body posture parameters from a top-down perspective that is invariant to the high level of visual diversity seen in a subject, such as a mouse, including coat color, fur differences, and size differences. Altogether, the invention provides a system that is sensitive, accurate, and scalable and can detect previously undescribed differences in gait and posture in mouse models of diseases and conditions.

The present disclosure relates to techniques for gait and posture analysis that includes several modular components, one of which, in some embodiments, is a neural network (e.g., a deep convolutional neural network) that has been trained to perform pose estimation using top-down videos of an open field. The neural network may provide multiple two-dimensional markers (in some embodiments, twelve such markers) of a subject's anatomical location (also referred to as "keypoints"), for each frame of video describing the pose of the subject at each time point. Another one of the modular components may be capable of processing the time series of poses and identifying intervals that represent individual strides. Another one of the modular components may be capable of extracting several gait metrics on a per-stride basis, and another modular component may be capable of extracting several posture metrics. Finally, another modular component may be configured to perform statistical analysis on the gait metrics and the posture metrics, as well as enabling aggregation of large amounts of data in order to provide consensus views of the structure of a subject's gait.

The system 100 of the present disclosure may operate using various components as illustrated in FIG. 1. The system 100 may include an image capture device 101, a device 102 and one or more systems 150 connected across one or more networks 199. The image capture device 101 may be part of, included in, or connected to another device (e.g., device 1600), and may be a camera, a high speed video camera, or other types of devices capable of capturing images and videos. The device 101, in addition to or instead of an image capture device, may include a motion detection sensor, infrared sensor, temperature sensor, atmospheric conditions detection sensor, and other sensors configured to detect various characteristics/environmental conditions. The device 102 may be a laptop, a desktop, a tablet, a smartphone, or other types of computing devices, and may include one or more components described in connection with device 1600 below.

The image capture device 101 may capture video (or one or more images) of one or more subjects on whom the formalin assay is performed, and may send video data 104 representing the video to the system(s) 150 for processing as described herein. The system(s) 150 may include one or more components shown in FIG. 1, and may be configured to process the video data 104 to determine gait and posture behaviors of the subject(s) over time. The system(s) 150 may determine difference data 148 representing one or more differences in the subject gait and/or posture and a control gait and/or posture. The difference data 148 may be send to the device 102 for output to a user to observe the results of processing the video data 104.

Details of the components of the system(s) 150 are described below. The various components may be located on the same or different physical devices. Communication between the various components may occur directly or across a network(s) 199. Communication between the device 101, the system(s) 150 and the device 102 may occur directly or across a network(s) 199. One or more components shown as part of the system(s) 150 may be located at the device 102 or at a computing device (e.g., device 1600) connected to the image capture device 101. In an example embodiment, the system(s) 150 may include a point track component 110, a gait analysis component 120, a posture analysis component 130, and a statistical analysis component 140. In other embodiments, the system(s) 150 may include fewer or more components than shown in FIG. 1 to perform the same or similar functionality as described below.

Figure 2:
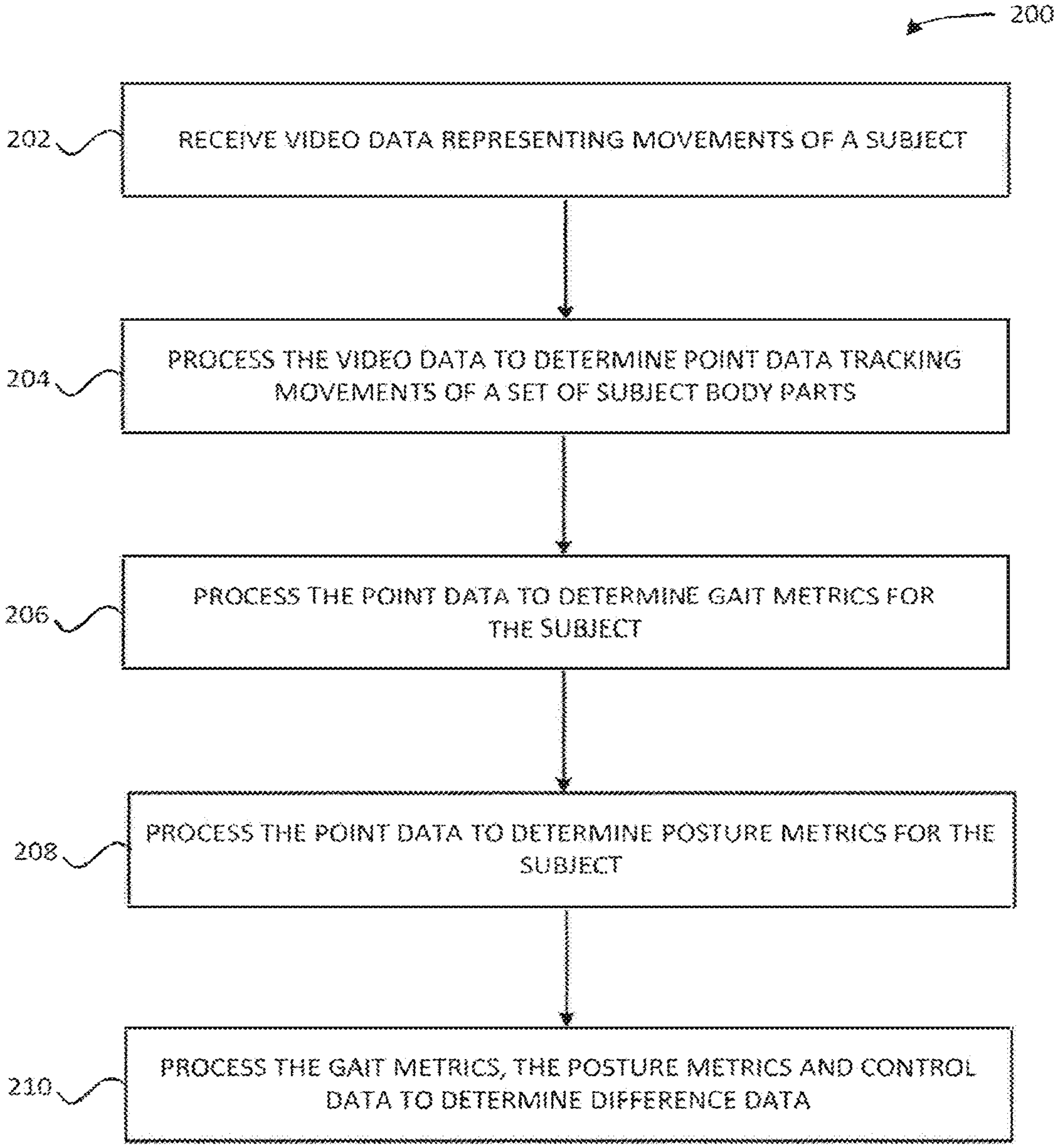
FIG. 2 is a flowchart illustrating an example process that may be performed by a system shown in FIG. 1 for analyzing video data of a subject(s) to determine subject gait and posture metrics, according to embodiments of the present disclosure.

FIG. 2 is a flowchart illustrating an example process 200 that may be performed by the system 100 shown in FIG. 1 for analyzing video data 104 of a subject to determine gait and posture metrics, according to embodiments of the present disclosure. At a high level, the process 200 begins with the image capture device 101 recording a video(s) of a subject's movements. In some embodiments, the video data 104 is a top-down perspective of the subject. In some embodiments, the subject(s) may be in an enclosure that has an open arena, for example, without a treadmill, a tunnel, etc. to direct the subject(s) in a particular fashion. This allows for observing subjects without having to train subjects to perform certain movements, such as walking on a treadmill or moving within a tunnel. At a step 202, the system(s) 150 may receive the video data 104 from the image capture device 101 (or a device 1600 connected to the image capture device 101 or within which the image capture device 101 is included). At a step 204, the point tracker component 110 of the system(s) 150 may process the video data 104 to determine point data 112. The point data 112 may represent data tracking movements of a set of subject body parts over a time period represented in the video data 104. Further details on the point tracker component 110 are described below in relation to FIG. 3. At a step 206, the gait analysis component 120 of the system(s) 150 may process the point data 112 to determine metrics data 122. The metrics data 122 may represent gait metrics for the subject. Further details on the gait analysis component 120 are described below in relation to FIG. 4. At a step 208, the posture analysis component 130 of the system(s) 150 may process the point data 112 to determine metrics data 132. The metrics data 132 may represent posture metrics for the subject. Further details on the posture analysis component 130 are described below in relation to FIG. 5. In some embodiments, the step 208 may be performed before the step 206. In some embodiments, the steps 206 and 208 may be performed in parallel, for example, the gait analysis component 120 may process the point data 112 while the posture analysis component 130 is processing the point data 112. In some embodiments, depending on system configuration, only one of the step 206 and 208 may be performed. For example, in some embodiments, the system(s) 150 may be configured to only determine gait metrics, and thus, only the step 206 may be performed by the gait analysis component 120. In another example, in some embodiments, the system(s) 150 may be configured to only determine posture metrics, and thus, only the step 208 may be performed by the gait analysis component 120. At a step 210, the statistical analysis component 140 of the system(s) 150 may process the metrics data 122, the metrics data 132 and control data 144 to determine difference data 148. Further details on the statistical analysis component 140 are described below.

Figure 3:
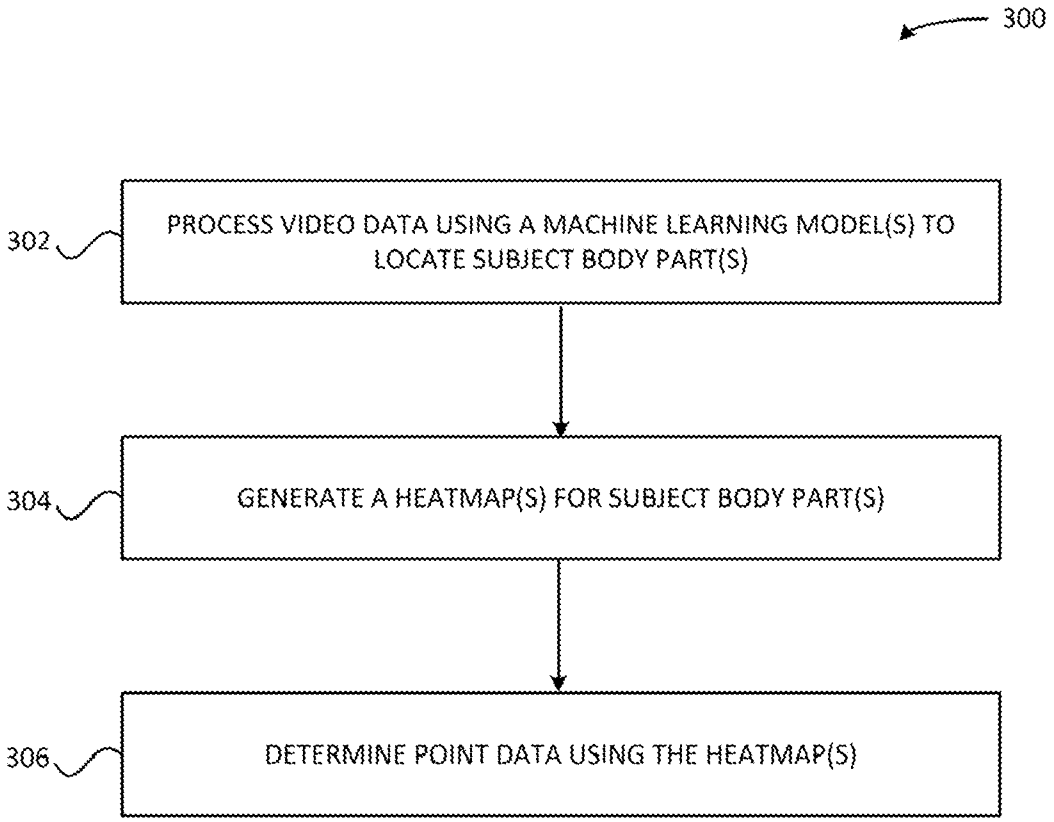
FIG. 3 is a flowchart illustrating an example process that may be performed by a point tracker component shown in FIG. 1 for tracking subject body parts in the video data, according to embodiments of the present disclosure.

FIG. 3 is a flowchart illustrating an example process 300 that may be performed by the point tracker component 110 for tracking subject body parts in the video data 104, according to embodiments of the present disclosure. At a step 302, the point tracker component 110 may process the video data 104 using a machine learning model(s) to locate subject body part(s). At a step 304, the point tracker component 110 may generate a heatmap(s) for the subject body part(s) based on processing the video data 104 using the machine learning model(s). The point tracker component 110 may use the machine learning model(s) to estimate a two-dimensional pixel coordinate where a subject body part appears within a video frame of the video data 104. The point tracker component 110 may generate a heatmap estimating a location of one subject body part for one video frame. For example, the point tracker component 110 may generate a first heatmap, where each cell in the heatmap may correspond to a pixel within the video frame, and may represent a likelihood of a first subject body part (e.g., a right forepaw) being located at the respective pixel. Continuing with the example, the point tracker component 110 may generate a second heatmap, where each cell may represent a likelihood of a second subject body part (e.g., a left forepaw) being located at the respective pixel. At a step 306, the point tracker component 110 may determine the point data 112 using the generated heatmap(s). The heatmap cell with the highest/maximum value may identify the pixel coordinate where the respective subject body part is located within the video frame.

The point tracker component 110 may be configured to locate two-dimensional coordinates of a set of subject body parts, identified as keypoints, in an image or video. In some embodiments, the set of subject body parts may be predefined and may be based on which keypoints are visually salient, such as ears or nose, and/or which keypoints capture important information for analyzing the gait and posture of the subject, such as limb joints or paws. In an example embodiment, the set of subject body parts may include twelve keypoints. In other embodiments, the set of subject body parts may include fewer than or more than twelve keypoints. In an example embodiment, the set of subject body parts may include: nose, left ear, right ear, base of neck, left forepaw, right forepaw, mid spine, left hind paw, right hind paw, base of tail, mid tail and tip of tail (as illustrated in FIG. 7B).

The point tracker component 110 may implement one or more pose estimation techniques. The point tracker component 110 may include one or more machine learning models configured to process the video data 104. In some embodiments, the one or more machine learning models may be a neural network such as, a deep neural network, a deep convolutional neural network, a recurrent neural network, etc. In other embodiments, the one or more machine learning models may be other types of models than a neural network. The point tracker component 110 may be configured to determine the point data 112 with high accuracy and precision because the metrics data 122, 132 may sensitive to errors in the point data 112. The point tracker component 110 may implement an architecture that maintains high-resolution features throughout the machine learning model stack, thereby preserving spatial precision. In some embodiments, the point tracker component 110 architecture may include one or more transpose convolutions to cause matching between a heatmap output resolution and the video data 104 resolution. The point tracker component 110 may be configured to determine the point data 112 in near real-time speeds and may run a high processing capacity GPU. The point tracker component 110 may be configured such that modifications and extensions can be made easily. In some embodiments, the point tracker component 110 may be configured to generate an inference at a fixed scale, rather than processing at multiple scales, to save computing resources and time.

In some embodiments, the video data 104 may track movements of one subject, and the point tracker component 110 may not be configured to perform any object detection techniques/algorithms. In other embodiments, the video data 104 may track movements of more than one subject, and the point track component 110 may be configured to perform object detection techniques to identify one subject from another subject within the video data 104.

In some embodiments, the point tracker component 110 may generate multiple heatmaps, each heatmap representing an inference of where one keypoint representing one subject body part is located within a frame of the video data 104. In one example, the video data 104 may have a 480×480 frame, and the point tracker component 110 may generate twelve 480×480 heatmaps. The maximum value in each heatmap may represent the highest confidence location for each respective keypoint. In some embodiments, the point tracker component 110 may take the maximum value of each of the twelve heatmaps and output that as the point data 112, thus, the point data 112 may include twelve (x,y) coordinates.

In some embodiments, the point tracker component 110 may be trained for a loss function, for example, a Gaussian distribution centered on the respective keypoint. The output of the neural network of the point tracker component 110 may be compared with the keypoint-centered Gaussian distribution, and the loss may be calculated as the mean squared difference between the respective keypoint and the heatmap generated by the point tracker component 110. In some embodiments, the point tracker component 110 may be trained using an optimization algorithm, for example, a stochastic gradient descent optimization algorithm. The point tracker component 110 may be trained using training video data of subjects having varying physical characteristics, such as, different coat color, different body lengths, different body sizes, etc.

The point tracker component 110 may estimate given keypoints with varying levels of confidence depending on the position of the subject body part on the subject body. For example, the location of the hind paws may be estimated with a higher confidence than the location of the forepaws because the forepaws may be more occluded than the hind paws in a top-down perspective. In another example, visually salient body parts, like the spine center, may have a lower confidence since it may be more difficult for the point tracker component 110 to locate accurately.

Now referring to the gait analysis component 120 and the posture analysis component 130. As used herein, gait metrics may refer to metrics derived from the subject's paw movements. Gait metrics may include, but is not limited to, step width, step length, stride length, speed, angular velocity, and limb duty factor. As used herein, posture metrics may refer to metrics derived from the movements of the subject's whole body. In some embodiments, the posture metrics may be based on movements of the subject nose and tail. Posture metrics, may include, but is not limited to, lateral displacement of nose, lateral displacement of tail base, lateral displacement of tail tip, nose lateral displacement phase offset, tail base displacement phase offset, and tail tip displacement phase offset.

Figure 4:
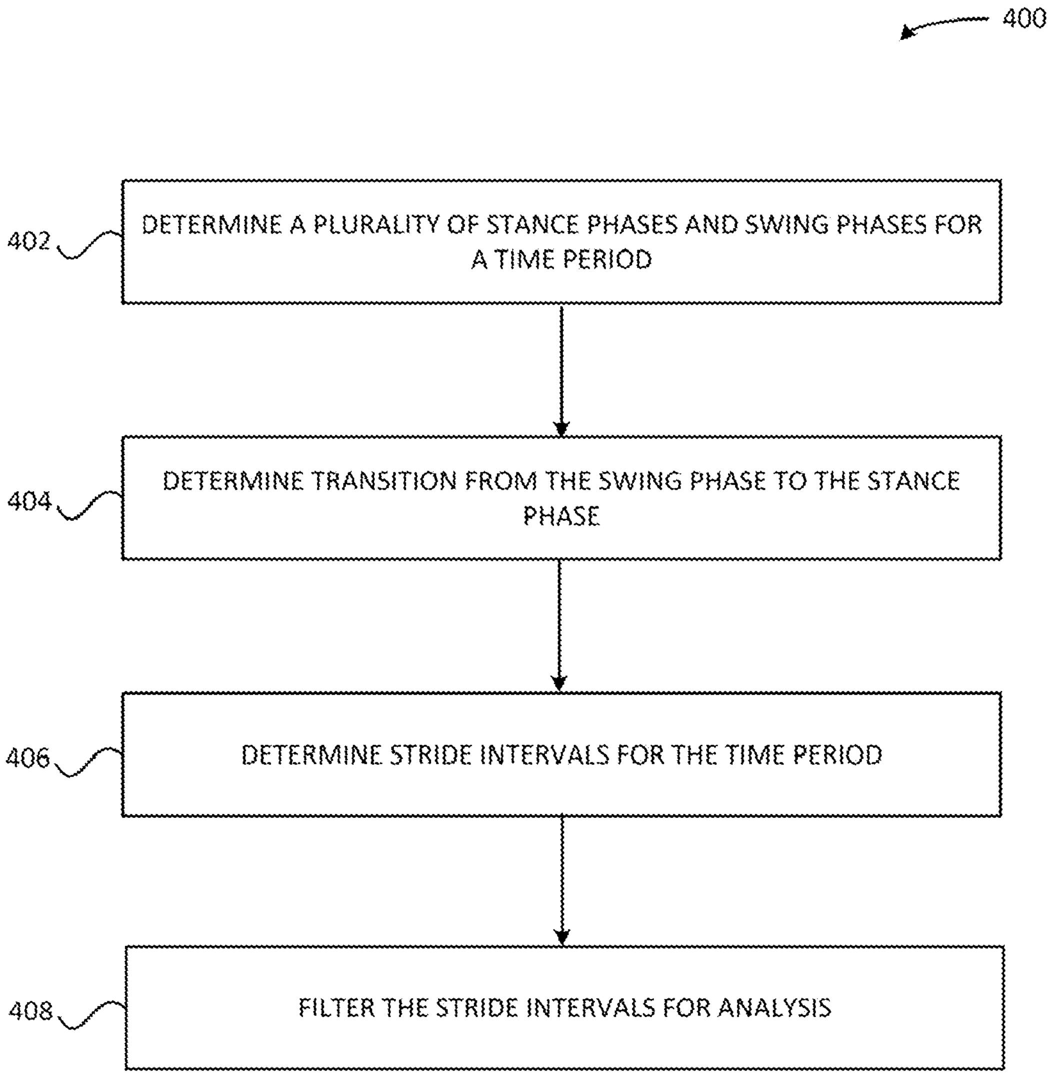
FIG. 4 is a flowchart illustrating an example process that may be performed by the system shown in FIG. 1 for determining stride intervals, according to embodiments of the present disclosure.

The gait analysis component 120 and the posture analysis component 130 may determine one or more of the gait metrics and the posture metrics on a per-stride basis. The system(s) 150 may determine a stride interval(s) represented in a video frame of the video data 104. In some embodiments, the stride interval may be based on a stance phase and a swing phase. FIG. 4 is a flowchart illustrating an example process 400 that may be performed by the gait analysis component 120 and/or the posture analysis component 130 to determine a set of stride intervals for analysis.

Figure 8A:
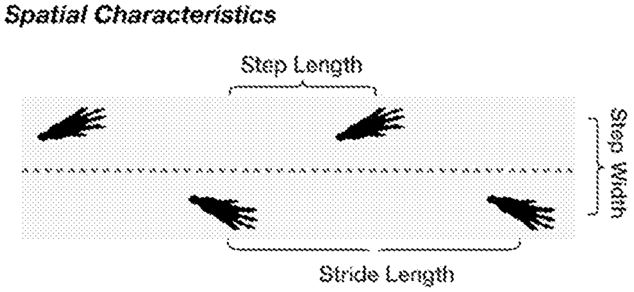
FIG. 8A-J shows schematic diagrams and graphs illustrating deriving gait phenotypes from video pose estimation.
Figure 8B:
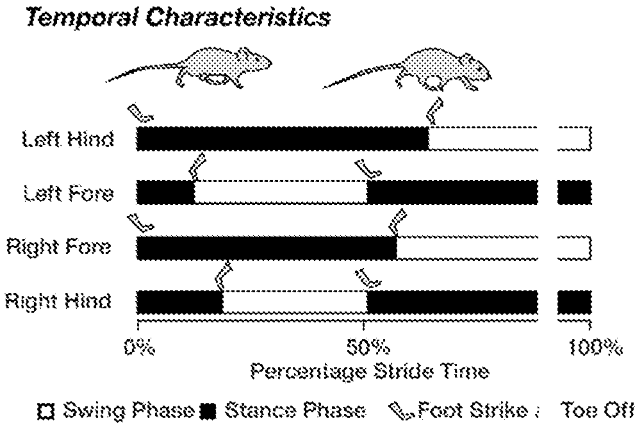
Figure 8C:
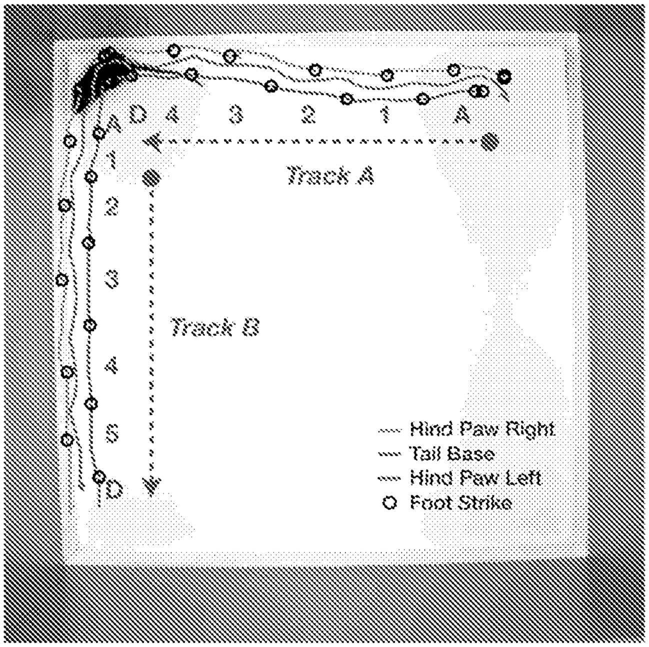

In example embodiments, the approach for detecting stride intervals is based on the cyclic structure of gait. During a stride cycle, each of the paws may have a stance phase and a swing phase. During the stance phase, the subject's paw is supporting the weight of the subject and is in static contact with the ground. During the swing phase, the paw is moving forward and is not supporting the subject's weight. The transition from a stance phase to a swing phase is referred to herein as a toe-off event, and the transition from a swing phase to a stance phase is referred to herein as a foot-strike event. FIG. 8A-C illustrates an example stance phase, an example swing phase, an example toe-off event and an example foot-strike event.

At a step 402, the system(s) 150 may determine a plurality of stance and swing phases represented in a time period. In an example embodiment, the stance and swing phases may be determined for the hind paws of the subject. The system(s) 150 may calculate a paw speed and may infer that a paw is in the stance phase when the speed falls below a threshold value, and may infer that the paw is in the swing phase when it exceeds that threshold value. At a step 404, the system(s) 150 may determine that the foot strike events occur at the video frame where the transition from the swing phase to the stance phase occurs. At a step 406, the system(s) 150 may determine the stride intervals represented in the time period. A stride interval may span over multiple video frames of the video data 104. The system(s) 150, for example, may determine that a time period of 10 seconds has 5 stride intervals, and that one of the 5 stride intervals is represented in 5 consecutive video frames of the video data 104. In an example embodiment, the left hind foot strike event may be defined as the event that separates/differentiates stride intervals. In another example embodiment, the right hind foot strike event may be defined as the event that separates/differentiates the stride intervals. In yet another example embodiment, a combination of the left hind foot strike event and the right hind foot strike event may be used to define the separate stride intervals. In some other embodiments, the system(s) 150 may determine the stance and swing phases for the fore paws, may calculate a paw speed based on the fore paws, and may differentiate between the stride intervals based on the right and/or left forepaw foot strike event. In some other embodiments, the transition from the stance phase to the swing phase—the toe-off event—may be used to separate/differentiate the stride intervals.

In some embodiments, it may be preferred to determine the stride intervals based on a hind foot strike event, rather than a forepaw strike event due to the keypoint inference quality (determined by the point tracker component 110) for the forepaws, in some cases, being of low confidence. This is may be a result of the forepaws being occluded more often than the hind paws from within a top-down view, and therefore the forepaws being more difficult to accurately locate.

At a step 408, the system(s) 150 may filter the determined stride intervals to determine which stride intervals are used to determine the metrics data 122, 132. In some embodiments, such filtering may remove spurious or low confidence stride intervals. In some embodiments, the criteria for removing the stride intervals may include, but is not limited to: low confidence keypoint estimate, physiologically unrealistic keypoint estimates, missing right hind paw strike event, and insufficient overall body speed of subject (e.g., a speed under 10 cm/sec).

In some embodiments, the filtering of the stride intervals may be based on a confidence level in determining the keypoints used to determine the stride intervals. For example, stride intervals determined with a confidence level below a threshold value may be removed from the set of stride intervals used to determine the metrics data 122, 132.

In some embodiments, the first and last strides are removed in a continuous sequence of strides to avoid starting and stopping behaviors from adding noise to the data to be analyzed. For example, a sequence of seven strides will result in at most five strides being used for analysis.

Figure 5:
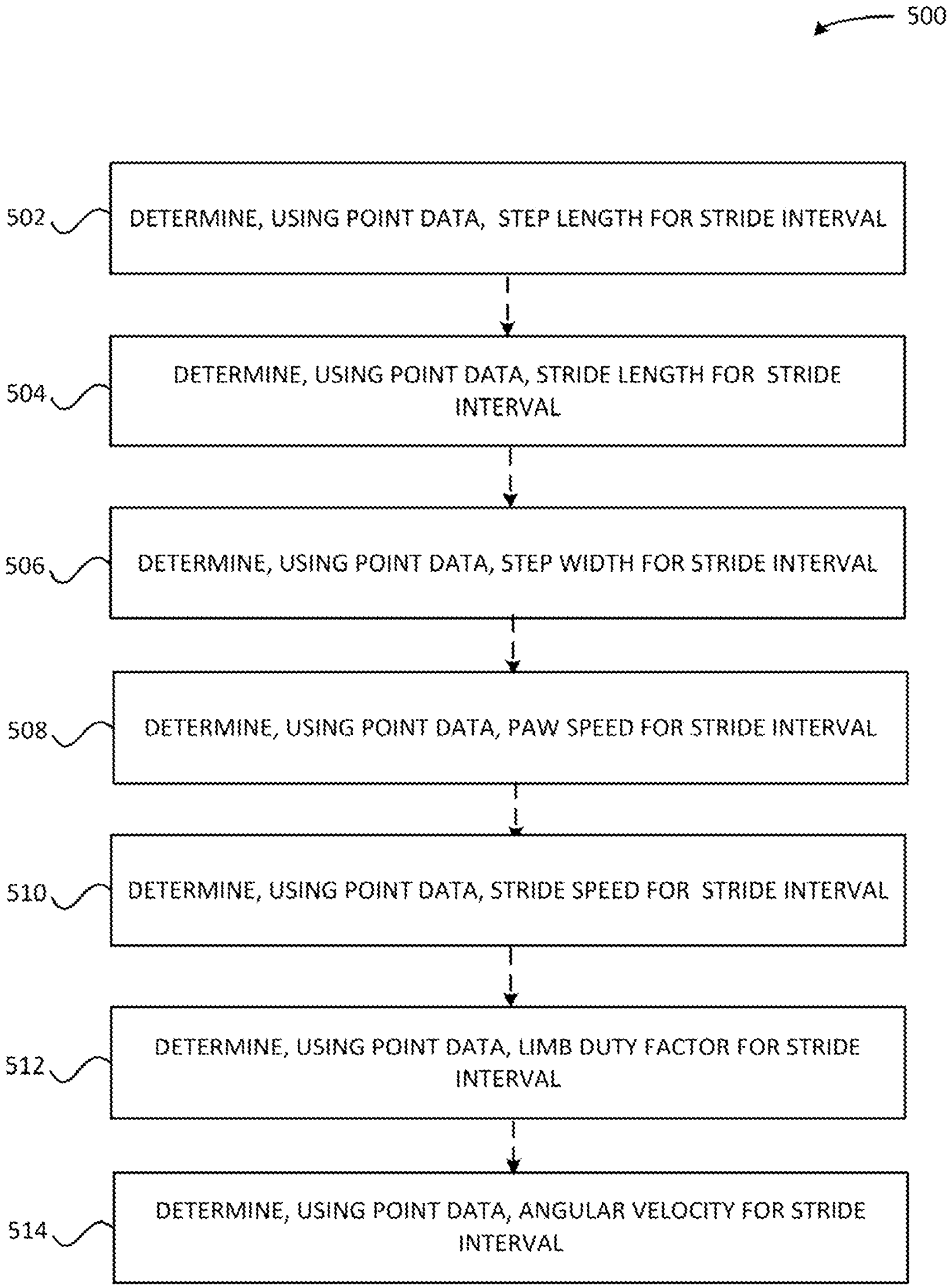
FIG. 5 is a flowchart illustrating an example process that may be performed by a gait analysis component shown in FIG. 1 for determining subject gait metrics, according to embodiments of the present disclosure.

After determining the stride intervals represented in the video data 104, the system(s) 150 may determine the gait metrics and the posture metrics. FIG. 5 is a flowchart illustrating an example process 500 that may be performed by the gait analysis component 120 for determining subject gait metrics, according to embodiments of the present disclosure. The steps of the process 500 may be performed in the optional sequence shown in FIG. 5. In other embodiments, the steps of the process 500 may be performed in a different sequence. In yet other embodiments, the steps of the process 500 may be performed in parallel.

At a step 502, the gait analysis component 120 may determine, using the point data 112, a step length for a stride interval determined to be analyzed at the step 408 shown in FIG. 4. The gait analysis component 120 may determine a step length for each stride interval for the time period. In some embodiments, the point data 112 may be for the keypoints representing a left hind paw, a left forepaw, a right hind paw and a right forepaw. In some embodiments, the step length may be a distance between the left forepaw and the right hind paw for the stride interval. In some embodiments, the step length may be a distance between the right forepaw and the left hind paw for the stride interval. In some embodiments, the step length may be a distance that the right hind paw travels past the previous left hind paw strike.

At a step 504, the gait analysis component 120 may determine, using the point data 112, a stride length for a stride interval determined to be analyzed at the step 408. The gait analysis component 120 may determine a stride length for each stride interval for the time period. In some embodiments, the point data 112 may be for the keypoints representing a left hind paw, a left forepaw, a right hind paw and a right forepaw. In some embodiments, the stride length may be a distance between the left forepaw and the left hind paw for the each stride interval. In some embodiments, the stride length may be a distance between the right forepaw and the right hind paw. In some embodiments, the stride length may be the full distance that the left hind paw travels for a stride from a toe-off event to a foot-strike event.

At a step 506, the gait analysis component 120 may determine, using the point data 112, a step width for a stride interval determined to be analyzed at the step 408. The gait analysis component 120 may determine a step width for each stride interval for the time period. In some embodiments, the point data 112 may be for the keypoints representing a left hind paw, a left forepaw, a right hind paw and a right forepaw. In some embodiments, the step width is a distance between the left fore paw and the right fore paw. In some embodiments, the step width is a distance between the left hind paw and the right hind paw. In some embodiments, the step width is an averaged lateral distance separating hind paws. This may be calculated as length of the shortest line segment that connects the right hind paw strike to the line that connects the left hind paw's toe-off location to its subsequent foot strike position.

At a step 508, the gait analysis component 120 may determine, using the point data 112, a paw speech for a stride interval determined to be analyzed at the step 408. The gait analysis component 120 may determine a paw speed for each stride interval for the time period. In some embodiments, the point data 112 may be for the keypoints representing a left hind paw, a right hind paw, a left forepaw, and a right forepaw. In some embodiments, the paw speed may be a speed of one of the paws during the stride interval. In some embodiments, the paw speed may be a speed of the subject and may be based on a tail base of the subject.

At a step 510, the gait analysis component 120 may determine, using the point data 112, a stride speed for a stride interval determined to be analyzed at the step 408. The gait analysis component 120 may determine a stride speed for each stride interval for the time period. In some embodiments, the point data 112 may be for the keypoints representing a tail base. In some embodiments, the stride speed may be determined by determining a set of speed data for the subject based on the movement of the subject tail base during a set of video frames representing the stride interval. Each speed data in the set of speed data may correspond to one frame of the set of video frames. The stride speed may be calculated by averaging (or combining in another manner) the set of speed data.

At a step 512, the gait analysis component 120 may determine, using the point data 112, a limb duty factor for a stride interval determined to be analyzed at the step 408. The gait analysis component 120 may determine a limb duty factor for each stride interval for the time period. In some embodiments, the point data 112 may be for the keypoints representing a right hind paw and a left hind paw. In some embodiments, the limb duty factor for the stride interval may be an average of a first duty factor and a second duty factor. The gait analysis component 120 may determine a first stance time representing an amount of time that the right hind paw is in contact with the ground during the stride interval, and then may determine the first duty factor based on the first stance time and the length of time for the stride interval. The gait analysis component 120 may determine a second stance time representing an amount of time that the left hind paw is in contact with the ground during the stride interval, and then may determine the second duty factor based on the second stance time and the length of time for the stride interval. In other embodiments, the limb duty factor may be based on the stance time and duty factors of the forepaws.

At a step 514, the gait analysis component 120 may determine, using the point data 112, an angular velocity for a stride interval determined to be analyzed at the step 408. The gait analysis component 120 may determine an angular velocity for each stride interval for the time period. In some embodiments, the point data 112 may be for the keypoints representing a tail base and a neck base. The gait analysis component 120 may determine a set of vectors connecting the tail base and the neck base, where each vector in the set corresponds to a frame of a set of frames for the stride interval. The gait analysis component 120 may determine the angular velocity based on the set of vectors. The vectors may represent an angle of the subject, and a first derivative of the angle value may be the angular velocity for the frame. In some embodiments, the gait analysis component 120 may determine a stride angular velocity by averaging the angular velocities for the frames for the stride intervals.

Figure 6:
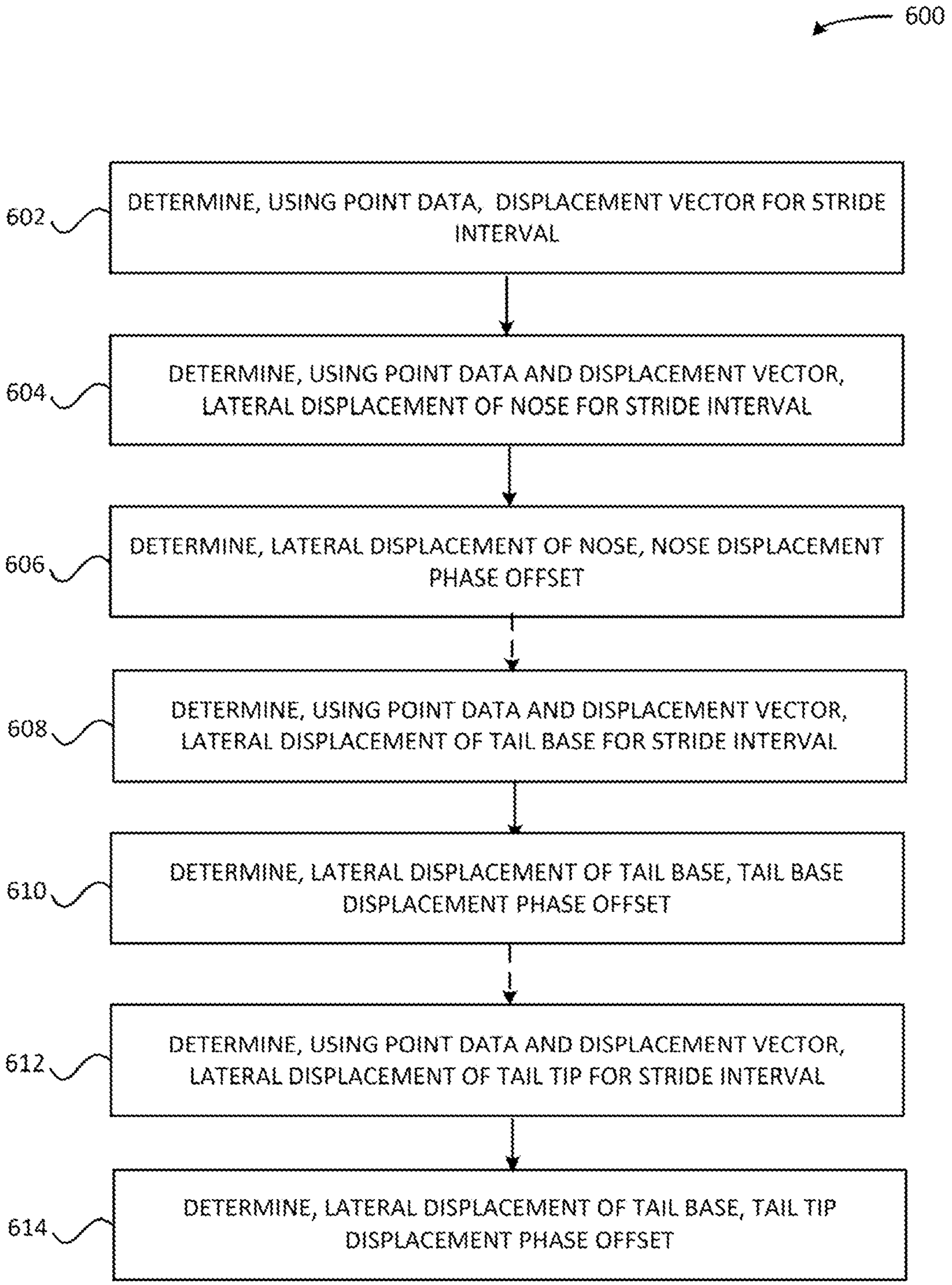
FIG. 6 is a flowchart illustrating an example process that may be performed by a posture analysis component shown in FIG. 1 for determining subject posture metrics, according to embodiments of the present disclosure.

FIG. 6 is a flowchart illustrating an example process 600 that may be performed by the posture analysis component 130 for determining subject posture metrics, according to embodiments of the present disclosure. At a high level, the posture analysis component 130 may determine lateral displacements of a nose, a tail tip and a tail base on the subject for individual stride intervals. Based on the lateral displacements of the nose, the tail tip, and the tail base, the posture analysis component 130 may determine a displacement phase offset of each of the respective subject body part. In that respective, the steps of the process 600 may be performed in a different sequence than that shown in FIG. 6. For example, the posture analysis component 130 may determine the lateral displacement of the nose and the nose displacement phase offset after determining or in parallel of determining the lateral displacement of the tail tip and the tail tip displacement phase offset.

To determine the lateral displacements, the posture analysis component 130 may first, at a step 602, determine using the point data 112, a displacement vector for a stride interval determined to be analyzed at the step 408. The posture analysis component 130 may determine the displacement vector for each stride interval for the time period. In some embodiments, the point data 112 may be for the keypoints representing a spine center of the subject. The stride interval may span over multiple video frames. In some embodiments, the displacement vector may be a vector connecting the spine center in a first video frame of the stride interval and the spine center in the last video frame of the stride interval.

At a step 604, the posture analysis component 130 may determine, using the point data 112 and the displacement vector (from the step 602), a lateral displacement of the subject nose for the stride interval. The posture analysis component 130 may determine the lateral displacement of the nose for each stride interval for the time period. In some embodiments, the point data 112 may be for the keypoints representing a spine center and a nose of the subject. In some embodiments, the posture analysis component 130 may determine a set of lateral displacements of the nose, where each lateral displacement of the nose may correspond to a video frame of the stride interval. The lateral displacement may be a perpendicular distance of the nose, in the respective video frame, from the displacement vector for the stride interval. In some embodiments, the posture analysis component 130 may subtract the minimum distance from the maximum distance and divide that by the subject body length so that the displacement measured in larger subjects may be comparable to the displacement measured in smaller subjects.

At a step 606, the posture analysis component 130 may determine, using the set of lateral displacements of the nose for the stride interval, a nose displacement phase offset. The posture analysis component 130 may perform an interpolation using the set of lateral displacements of the nose to generate a smooth curve lateral displacement of the nose for the stride interval, then may determine, using the smooth curve lateral displacement of the nose, when a maximum displacement of the nose occurs during the stride interval. The posture analysis component 130 may determine a percent stride location representing a percent of the stride interval that is completed when the maximum displacement of the nose occurs. In some embodiments, the posture analysis component 130 may perform a cubic spline interpolation in order to generate the smooth curve for the displacement, and because of the cubic interpolation the maximum displacement may occur at time points between video frames.

At a step 608, the posture analysis component 130 may determine, using the point data 112 and the displacement vector (from the step 602), a lateral displacement of the subject tail base for the stride interval. The posture analysis component 130 may determine the lateral displacement of the tail base for each stride interval for the time period. In some embodiments, the point data 112 may be for the keypoints representing a spine center and a tail base of the subject. In some embodiments, the posture analysis component 130 may determine a set of lateral displacements of the tail base, where each lateral displacement of the tail base may correspond to a video frame of the stride interval. The lateral displacement may be a perpendicular distance of the tail base, in the respective video frame, from the displacement vector for the stride interval. In some embodiments, the posture analysis component 130 may subtract the minimum distance from the maximum distance and divide that by the subject body length so that the displacement measured in larger subjects may be comparable to the displacement measured in smaller subjects.

At a step 610, the posture analysis component 130 may determine, using the set of lateral displacements of the tail base for the stride interval, a tail base displacement phase offset. The posture analysis component 130 may perform an interpolation using the set of lateral displacements of the tail base to generate a smooth curve lateral displacement of the tail base for the stride interval, then may determine, using the smooth curve lateral displacement of the tail base, when a maximum displacement of the nose occurs during the stride interval. The posture analysis component 130 may determine a percent stride location representing a percent of the stride interval that is completed when the maximum displacement of the tail base occurs. In some embodiments, the posture analysis component 130 may perform a cubic spline interpolation in order to generate the smooth curve for the displacement, and because of the cubic interpolation the maximum displacement may occur at time points between video frames.

At a step 612, the posture analysis component 130 may determine, using the point data 112 and the displacement vector (from the step 602), a lateral displacement of the subject tail tip for the stride interval. The posture analysis component 130 may determine the lateral displacement of the tail tip for each stride interval for the time period. In some embodiments, the point data 112 may be for the keypoints representing a spine center and a tail tip of the subject. In some embodiments, the posture analysis component 130 may determine a set of lateral displacements of the tail tip, where each lateral displacement of the tail tip may correspond to a video frame of the stride interval. The lateral displacement may be a perpendicular distance of the tail tip, in the respective video frame, from the displacement vector for the stride interval. In some embodiments, the posture analysis component 130 may subtract the minimum distance from the maximum distance and divide that by the subject body length so that the displacement measured in larger subjects may be comparable to the displacement measured in smaller subjects.

At a step 614, the posture analysis component 130 may determine, using the set of lateral displacements of the tail tip for the stride interval, a tail base displacement phase offset. The posture analysis component 130 may perform an interpolation using the set of lateral displacements of the tail tip to generate a smooth curve lateral displacement of the tail tip for the stride interval, then may determine, using the smooth curve lateral displacement of the tail tip, when a maximum displacement of the nose occurs during the stride interval. The posture analysis component 130 may determine a percent stride location representing a percent of the stride interval that is completed when the maximum displacement of the tail tip occurs. In some embodiments, the posture analysis component 130 may perform a cubic spline interpolation in order to generate the smooth curve for the displacement, and because of the cubic interpolation the maximum displacement may occur at time points between video frames.

In reference to the statistical analysis component 140 of the system(s) 150, the statistical analysis component 140 may take as input the metrics data 122 (determined by the gait analysis component 120) and the metrics data 132 (determined by the posture analysis component 130). In some embodiments of the invention the statistical analysis component 140 may only take the metrics data 122, based on the system being configured for processing gait metrics data only. In other embodiments, the statistical analysis component 140 may only take the metrics data 132 based on the system being configured for processing posture metrics data only.

Subject body size and subject speed can affect the gait and/or posture of the subject. For example, a subject that moves faster will have a different gait than a subject that moves slow. As a further example, a subject with a larger body will have a different gait than a subject with a smaller body. However, in some cases a difference (as compared to a control subject gait) in stride speed may be a defining feature of gait and posture changes due to genetic or pharmacological perturbation. The system(s) 150 collects multiple repeated measurements for each subject (via the video data 104 and a subject in an open area), and each subject has a different number of strides giving rise to imbalanced data. Averaging over repeated strides, which yields one average value per subject, may be misleading as it removes variation and introduces false confidence. At the same time, classical linear models do not discriminate between stable intra-subject variations and inter-subject fluctuations, which can bias the statistical analysis. To address these issues, the statistical analysis component 140, in some embodiments, employ a linear mixed model(s) (LMM) to dissociate within-subject variation from genotype-based variation between subjects. In some embodiments, the statistical analysis component 140 may capture the main effects such as subject size, genotype, age, and may additionally capture a random effect for the intra-subject variation. The techniques of the invention collects multiple repeated measurements at different ages of the subject giving rise to a nested hierarchical data structure. Example statistical models implemented at the statistical analysis component 140 are shown below as models M1, M2 and M3. These models follow the standard LMM notation with (Genotype, BodyLength, Speed, TestAge) denoting the fixed effects and (SubjectID/TestAge) (where the test age is nested within the subject) denoting the random effect.

M1: Phenotype~Genotype+TestAge+BodyLength+(1|MouseID/TestAge)

M2: Phenotype~Genotype+TestAge+Speed+(1|MouseID/TestAge)

M3: Phenotype~Genotype+TestAge+Speed+BodyLength+(1|MouseID/TestAge)

The model M1 take age and body length as inputs, the model M2 take age and speed as inputs, and the model M3 take age, speed and body length as inputs. In some embodiments, the models of the statistical analysis component 140 does not include subject sex as an effect because the sex may be highly correlated with the body length/size of the subject. In other embodiments, the models of the statistical analysis component 140 may take subject sex as an input. Using the point data 112 (determined by the point tracker component 110), enables determination of subject body size and speed for these models. Therefore, no additional measurements are needed to these variables for the models.

One or more of the data included in the metrics data 122, 132 may be circular variables (e.g., stride length, angular velocities, etc.), and the statistical analysis component 140 may implement a function of linear variables using a circular-linear regression model. The linear variables, such as body length and speed, may be included as covariates in the model. In some embodiments, the statistical analysis component 140 may implement a multivariate outlier detection algorithm at the individual subject level to identify subjects with injuries and developmental effects.

The statistical analysis component 140 may, in some embodiments, also implement a linear discriminant analysis that processes the metrics data 122, 132 with respect to the control data 144 and outputs the difference data 148. The linear discriminant analysis allows for quantitatively distinguish between the subject gait and/or posture metrics and a control subject gait and/or posture metrics.

Stitching Video Feeds

In some embodiments, the video data 104 may be generated using multiple video feeds capturing movements of the subject from multiple different angles/views. The video data 104 may be generated by stitching/combining a first video of a top view of the subject and a second video of a side view of the subject. The first video may be captured using a first image capture device (e.g., device 101*a*) and the second video may be captured using a second image capture device (e.g., device 101*b*). Other views of the subject may include a right side view, a left side view, a top-down view, a bottom-up view, a front side view, a back side view, and other views. Videos from these different views may be combined to generate the video data 104 to provide a comprehensive/expansive view of the subject's movements that may result in more accurate and/or efficient classification of subject behavior by the automated phenotyping system. In some embodiments, videos from different views may be combined to provide a wide field of view with a short focal distance, while preserving a top-down perspective over the entirety of the view. In some embodiments, the multiple videos from different views may be processed using one or more ML models (e.g., neural networks) to generate the video data 104. In some embodiments, the system may generate 3D video data using 2D video/images.

In some embodiments, the videos captured by the multiple image capture devices 101 may be synced using various techniques. For example, the multiple image capture devices 101 may be synced to a central clock system and controlled by a master node. Synchronization of multiple video feeds may involve the use various hardware and software such as an adapter, a multiplexer, USB connections between the image capture devices, wireless or wired connections to the network(s) 199, software to control the devices (e.g., MotionEyeOS), etc.

In an example embodiment, the image capture device 101 may be an ultra-wide-angle lens (i.e., a FishEye lens) that produces strong visual distortion intended to create a wide panoramic or hemispherical image, and capable of achieving extremely wide angles of view. In an example implementation, the system to capture the videos for video data 104 may include 4 FishEye lens cameras connected to 4 single-board computing devices (e.g., a Raspberry Pi), and an additional image capture device to capture a top-down view. The system may synchronize these components using various techniques. One technique involves pixel/spatial interpolation, for example, where a point-of-interest (e.g., a body part on the subject) is located at (x, y), the system identifies, with respect to time, a position within the top-down view video along the x and y axes. In an example, the pixel interpolation for the x-axis may be calculated by the single-board computing device per the following equation:

$$(\text{Pi offset } \Delta X/\text{Pi offset } \Delta T)^*(\text{top-down view offset } \Delta T)+\text{the initial point}(x)$$

The equation then may be used to calculate the point-of-interest position for the y axis. In some embodiments, to address lens distortion during video calibration, padding may be added to one or more video feeds (instead of scaling the video feed).

Subjects

Some aspects of the invention include use of gait and posture analysis methods with a subject. As used herein, a the term "subject" may refer to a human, non-human primate, cow, horse, pig, sheep, goat, dog, cat, pig, bird, rodent, or other suitable vertebrate or invertebrate organism. In certain embodiments of the invention, a subject is a mammal and in certain embodiments of the invention, a subject is a human. In some embodiments, a subject used in method of the invention is a rodent, including but not limited to a: mouse, rat, gerbil, hamster, etc. In some embodiments of the invention, a subject is a normal, healthy subject and in some embodiments, a subject is known to have, at risk of having, or suspected of having a disease or condition. In certain embodiments of the invention, a subject is an animal model for a disease or condition. For, example though not intended to be limiting, in some embodiments of the invention a subject is a mouse that is an animal model for autism.

As a non-limiting example, a subject assessed with a method and system of the invention may be a subject that is an animal model for a condition such as a model for one or more of: psychiatric illness, neurodegenerative illness, neuromuscular illness, autism spectrum disorder, schizophrenia, bipolar disorder, Alzheimer's disease, Rett syndrome, ALS, and Down syndrome.

In some embodiments of the invention, a subject is a wild-type subject. As used herein the term "wild-type" means to the phenotype and/or genotype of the typical form of a species as it occurs in nature. In certain embodiments of the invention a subject is a non-wild-type subject, for example, a subject with one or more genetic modifications compared to the wild-type genotype and/or phenotype of the subject's species. In some instances, a genotypic/phenotypic difference of a subject compared to wild-type results from a hereditary (germline) mutation or an acquired (somatic) mutation. Factors that may result in a subject exhibiting one or more somatic mutations include but are not limited to: environmental factors, toxins, ultraviolet radiation, a spontaneous error arising in cell division, a teratogenic event such as but not limited to radiation, maternal infection, chemicals, etc.

In certain embodiments of methods of the invention, a subject is a genetically modified organism, also referred to as an engineered subject. An engineered subject may include a pre-selected and/or intentional genetic modification and as such exhibits one or more genotypic and/or phenotypic traits that differ from the traits in a non-engineered subject. In some embodiments of the invention, routine genetic engineering techniques can be used to produce an engineered subject that exhibits genotypic and/or phenotypic differences compared to a non-engineered subject of the species. As a non-limiting example, a genetically engineered mouse in which a functional gene product is missing or is present in the mouse at a reduced level and a method or system of the invention can be used to assess the genetically engineered mouse phenotype, and the results may be compared to results obtained from a control (control results).

In some embodiments of the invention, a subject may be monitored using a gait level determining method or system of the invention and the presence or absence of an activity disorder or condition can be detected. In certain embodiments of the invention, a test subject that is an animal model of an activity and/or movement condition may be used to assess the test subject's response to the condition. In addition, a test subject that is an animal model of a movement and/or activity condition may be administered a candidate therapeutic agent or method, monitored using a gait monitoring method and/or system of the invention and results can be used to determine an efficacy of the candidate therapeutic agent to treat the condition. The terms "activity" and "action" may be used interchangeably herein.

As described elsewhere here, trained models of the invention may be configured to detect behavior of a subject, regardless of the subject's physical characteristics. In some embodiments of the invention, one or more physical characteristics of a subject may be pre-identified characteristics. For example, though not intended to be limiting, a pre-identified physical characteristic may be one or more of: a body shape, a body size, a coat color, a gender, an age, and a phenotype of a disease or condition.

Controls and Candidate Compound Testing and Screening

Results obtained for a subject using the method or system of the invention can be compared to control results. Methods of the invention can also be used to assess a difference in a phenotype in a subject versus a control. Thus, some aspects of the invention provide methods of determining the presence or absence of a change in an activity in a subject compared to a control. Some embodiments of the invention include using gait and posture analysis of the invention to identify phenotypic characteristics of a disease or condition.

Results obtained using the method or system of the invention can be advantageously compared to a control. In some embodiments of the invention, one or more subjects can be assessed using an automated gait analysis method followed by retesting the subjects following administration of a candidate therapeutic compound to the subject(s). The term "test" subject may be used herein in relation to a subject that is assessed using a method or system of the invention. In certain embodiments of the invention, a result obtained using an automated gait analysis method to assess a test subject is compared to results obtained from the automated gait analysis methods performed on other test subjects. In some embodiments of the invention, a test subject's results are compared to results of the automated gait analysis method performed on the test subject at a different time. In some embodiments of the invention, a result obtained using an automated gait analysis method to assess a test subject is compared to a control result.

A control value may be a value obtained from testing a plurality of subjects using a gait analysis method of the invention. As used herein a control result may be a predetermined value, which can take a variety of forms. It can be a single cut-off value, such as a median or mean. It can be established based upon comparative groups, such as subjects that have been assessed using an automated gait analysis method of the invention under similar conditions as the test subject, wherein the test subject is administered a candidate therapeutic agent and the comparative group has not been contacted with the candidate therapeutic agent. Another example of comparative groups may include subjects known to have a disease or condition and groups without the disease or condition. Another comparative group may be subjects with a family history of a disease or condition and subjects from a group without such a family history. A predetermined value can be arranged, for example, where a tested population is divided equally (or unequally) into groups based on results of testing. Those skilled in the art are able to select appropriate control groups and values for use in comparative methods of the invention. Non-limiting examples of types of candidate compounds include chemicals, nucleic acids, proteins, small molecules, antibodies, etc.

A subject assessed using an automated gait analysis method or system of the invention may be monitored for the presence or absence of a change that occurs in a test condition versus a control condition. As non-limiting examples, in a subject, a change that occurs may include, but is not limited to one of more of: a frequency of movement, a response to an external stimulus, etc. Methods and systems of the invention can be used with test subjects to assess the effects of a disease or condition of the test subject and can be used to assess efficacy of candidate therapeutic agents to treat a disease or condition. As a non-limiting example of use of method of the invention to assess the presence or absence of a change in a test subject as a means to identify efficacy of a candidate therapeutic agent, a test subject known to be an animal model of a disease such as autism is assessed using an automated gait analysis method of the invention. The test subject is administered a candidate therapeutic agent and assessed again using the automated gait analysis method. The presence or absence of a change in the test subject's results indicates a presence or absence, respectively, of an effect of the candidate therapeutic agent on the autism in the test subject. Diseases and conditions that can be assessed using a gait analysis method of the invention include, but are not limited to: ALS, autism, Down syndrome, Rett syndrome, bipolar disorder, dementia, depression, a hyperkinetic disorder, an anxiety disorder, a developmental disorder, a sleep disorder, Alzheimer's disease, Parkinson's disease, a physical injury, etc.

It will be understood that in some embodiments of the invention, a test subject may serve as its own control, for example by being assessed two or more times using an automated gait analysis method of the invention and comparing the results obtained at two or more of the different assessments. Methods and systems of the invention can be used to assess progression or regression of a disease or condition in a subject, by identifying and comparing changes in gait characteristics in a subject over time using two or more assessments of the subject using an embodiment of a method or system of the invention.

Diseases and Disorders

Methods and systems of the invention can be used to assess activity and/or behavior of a subject known to have, suspected of having, or at risk of having a disease or condition. In some embodiments, the disease and/or condition is one associated with an abnormal level of an activity or behavior. In a non-limiting example, a test subject that may be subject with anxiety or a subject that is an animal model of anxiety may have one or more activities or behaviors that are associated with anxiety that can be detected using an embodiment of a method of the invention. Results of assessing the test subject can be compared to control results of the assessment, for example of a control subject that does not have anxiety, a control subject that is not a subject that is an animal model of anxiety, a control standard obtained from a plurality of subjects without the condition, etc. Differences in the results of the test subject and the control can be compared. Some embodiments of methods of the invention can be used to identify subjects that have a disease or condition that is associated with abnormal activity and/or behavior.

Onset, progression, and/or regression of a disease or a condition associated with an abnormal activity and/or behavior can also be assessed and tracked using embodiments of methods of the invention. For example in certain embodiments of methods of the invention, 2, 3, 4, 5, 6, 7, or more assessments of an activity and/or behavior of a subject are carried out at different times. A comparison of two or more of the results of the assessments made at different times can show differences in the activity and/or behavior of the subject. An increase in a determined level or type of an activity may indicate onset and/or progression in the subject of a disease or condition associated with the assessed activity. A decease in a determined level or type of an activity may indicate regression in the subject of a disease or condition associated with the assessed activity. A determination that an activity has ceased in a subject may indicate the cessation in the subject of the disease or condition associated with the assessed activity.

Certain embodiments of methods of the invention can be used to assess efficacy of a therapy to treat a disease or condition associated with abnormal activity and/or behavior. For example, a test subject may be administered a candidate therapy and methods of the invention used to determine in the subject, a presence or absence of a change in activity associated with the disease or condition. A reduction in an abnormal activity following administration of a candidate therapy may indicate efficacy of the candidate therapy against the disease or condition.

As indicated elsewhere herein, a gait analysis method of the invention may be used to assess a disease or condition in a subject and may also be used to assess animal models of diseases and conditions. Numerous different animal models for diseases and conditions are known in the art, including but not limited to numerous mouse models. A subject assessed with a system and/or method of the invention may be a subject that is an animal model for a disease or condition such as a model for a disease or condition such as, but not limited to: neurodegenerative disorders, neuromuscular disorders, neuropsychiatric disorders, ALS, autism, Down syndrome, Rett syndrome, bipolar disorder, dementia, depression, a hyperkinetic disorder, an anxiety disorder, a developmental disorder, a sleep disorder, Alzheimer's disease, Parkinson's disease, a physical injury, etc. Additional models of diseases and disorders that may be assessed using a method and/or system of the invention are known in the art, see for example: Barrot M. Neuroscience 2012; 211: 39-50; Graham, D. M., Lab Anim (NY) 2016; 45: 99-101; Sewell, R. D. E., Ann Transl Med 2018; 6: S42. 2019 Jan. 2008; and Jourdan, D., et al., Pharmacol Res 2001; 43: 103-110, the contents of which are incorporated herein by reference in their entirety.

In addition to testing subjects with known diseases or disorders, methods of the invention may also be used to assess new genetic variants, such as engineered organisms. Thus, methods of the invention can be used to assess an engineered organism for one or more characteristics of a disease or condition. In this manner, new strains of organisms, such as new mouse strains can be assessed and the results used to determine whether the new strain is an animal model for a disease or disorder.

EXAMPLES

Example 1. Model Development: Data Training, Testing, and Model Validation

Methods

Training Data

Labeled data consists of 8,910 480×480 grayscale frames containing a single mouse in the open field along with the twelve manually labeled pose keypoints per frame. Strains were selected from a diverse set of mouse strain with different appearance accounting for variation in coat color, body size and obesity. FIG. 8C shows a representative frame generated by the open field apparatus. The frames were generated from the same open field apparatus as was used to generate experimental data previously (Geuther, B. Q. et al., Commun Biol (2019) 2:1-11). Pose keypoint annotations were performed by several Kumar lab members. Frame images and keypoint annotations were stored together using an HDF5 format, which was used for neural network training. Frame annotations were split into a training dataset (7,910 frames) and a validation dataset (1,000 frames) for training.

Neural Network Training

The network was trained over 600 epochs and validations were performed at the end of every epoch. The training loss curves (FIG. 8C) show a fast convergence of the training loss without an overfitting of the validation loss. Transfer learning (Weiss, K. et al., J Big Data (2016) 3:9; Tan, C. et al. $27^{th}$ Intl Conference on Artificial Neural Networks (2018), 270-279, arXiv:1808.01974 [cs.LG]) was used on the network in order to minimize the labeling requirements and improve the generality of the model. Initially, the imagenet model was used, which was provided by the authors of the HRNet paper (hrnet_w32-36af842e.pth) and the weights were frozen up to the second stage during training. In order to further improve the generality of the network several data augmentation techniques were employed during training including: rotation, flipping, scaling, brightness, contrast and occlusion. The ADAM optimizer was used to train the network. The learning rate was initially set to $5\times10^{-4}$, then reduced to $5\times10^{-5}$ at the $400^{th}$ epoch and $5\times10^{-6}$ at the $500^{th}$ epoch.

Statistical Analysis

The following LMM model was considered for repeated measurements:

$$y_{ij} = x_{ij}^T\beta + \gamma_i + \varepsilon_{ij},\ i = 1, \ldots , n,\ j = 1, \ldots , n_i$$

where n is the total number of subjects; $y_{ij}$ is the $j^{th}$ repeat measurement on the $i^{th}$ subject, $n_i$ denotes the number of repeat measurements on subject i; $x_{ij}$ is a p×1 vector of covariates such as body length, speed, genotype, age; $\beta$ is a p×1 vector of unknown fixed population-level effects; $\gamma_i$ is a random intercept, which describes subject-specific deviation from the population mean effect; and $\varepsilon_{ij}$ is the error term that describes the intrasubject variation of the $i^{th}$ subject that is assumed to be independent of the random effect. To test fixed effects and get p-values, the F test with Satterthwaite's approximation to the denominator degrees of freedom was used. The LMM models were fit using the lme4 package in R (Bates, D. et al., J Stat Softw (2015) 67:1-48).

The circular phase variables in FIG. 14A were modeled as a function of linear variables using a circular-linear regression model. Analyzing circular data is not straightforward and statistical models developed for linear data do not apply to circular data [Calínski, T. & Harabasz, Communications in Statistics-theory and Methods 3, 1-27 (1974)]. The circular response variables were assumed to have been drawn from a von-Mises distribution with unknown mean direction $\mu$ and concentration parameter $\kappa$. The mean direction parameter was related to the variables X through the equation:

$$Y_i \sim \text{von Mises}(\mu_i,\kappa),\ \mu_i=\mu+g(\gamma_1 X_1+\ldots+\gamma_p X_p),\ i=1;\ldots,n$$

where g(u)=2 $\tan^{-1}$(u) is a link function such that for $-\infty<u<\infty$, $-\pi<g(u)<\pi$. The parameters $\mu$; $\gamma_1 \ldots \gamma_k$ and $\kappa$ were estimated via maximum likelihood. The model was fitted using the circular package in R [Tibshirani, R. et al. Journal of the Royal Statistical Society: Series B (Statistical Methodology) 63, 411-423 (2001)].

Animals

Animal strains used in experiments are shown in FIG. 14B-D.

Experimental Descriptions and Results

The approach to gait and posture analysis was composed of several modular components. At the base of the toolkit was a deep convolutional neural network that has been trained to perform pose estimation on top-down video of an open field. This network provided twelve two-dimensional markers of mouse anatomical location, or "keypoints", for each frame of video describing the pose of the mouse at each time point. Also developed, were downstream components capable of processing the time series of poses and identifying intervals that represent individual strides. These strides formed the basis of almost all of the phenotypic and statistical analyses that followed. The methods permit extraction of several important gait metrics on a per-stride basis because pose information was obtained for each stride interval (see FIG. 14A for a list of metrics). This resulted in significant power to perform statistical analysis on stride metrics as well as allowing aggregation of large amounts of data in order to provide consensus views of the structure of mouse gait.

Pose Estimation

Pose estimation located the 2D coordinates of a pre-defined set of keypoints in an image or video, and was a foundation of methods for quantifying and analyzing gait. The selected pose keypoints were either visually salient, such as ears or nose, or capture important information for understanding pose, such as limb joints or paws. Twelve keypoints were selected to capture mouse pose: nose, left ear, right ear, base of neck, left forepaw, right forepaw, mid spine, left hind paw, right hind paw, base of tail, mid tail and tip of tail (FIG. 7B).

Much effort has been spent developing and refining pose estimation techniques for human pose (Moeslund, T. B. et al., Comput Vis Image Underst (2006) 104:90-126; Dang, Q. et al., Tsinghua Sci Technol (2019) 24:663-676). Traditional approaches to pose estimation relied on techniques such as the use of local body part detectors and modeling of skeletal articulation. These approaches were limited in their ability to overcome complicating factors such as complex configurations and body part occlusion. Some of these shortcomings were addressed by developing a deep neural network for pose estimation was the DeepPose (Toshev, A. & Szegedy, C., Proc IEEE Conf Comp Vis Pattern Recognit (2014), 1653-1660). DeepPose was able to demonstrate improvements on the state-of-the-art performance for pose estimation using several benchmarks. After the publication of DeepPose, the majority of successful work on pose estimation leveraged deep convolutional neural network architectures. Some prominent examples include: DeeperCut (Insafutdinov, E., et al., European Conference on Computer Vision (2016), 34-50), Stacked Hourglass Networks (Newell, A. et al., European Conference on Computer Vision (2016), 483-499), and Deep High-Resolution architecture (HRNet) (Sun, K. et al., Proc IEEE Conf Comp Vis Pattern Recognit (2019), 5693-5703). Some concepts used in high performance pose estimation architectures developed for human pose estimation were considered in the development of the rodent pose estimation methods included in methods of the invention.

There were several important considerations on which the rodent pose estimation architecture selection was based.

- High accuracy and precision for pose inference: the gait inference method is sensitive to errors in pose estimation so it is desirable to reduce those errors as much as possible
- Speed of inference: should be able to infer at or near real time speeds (30 fps) on a modern high end GPU
- Simplicity and generality of architecture to facilitate modification and extension.
- Fixed scale inference: because all of the images are at fixed scale, approaches that are designed to work at multiple scales waste network capacity and inference time.
- Available open source implementation
- Modularity of architecture in order to facilitate potential future upgrades.

Based on these criteria the HRNet architecture (Sun, K. et al., Proc IEEE Conf Comp Vis Pattern Recognit (2019), 5693-5703) was selected for the network and it was modified for the experimental setup. The main differentiator of this architecture is that it maintains high-resolution features throughout the network stack, thereby preserving spatial precision (FIG. 7A). HRNet showed highly competitive performance in terms of both GPU efficiency and pose accuracy. The interface was also highly modular and is expected to allow for relatively simple network upgrades if needed. The smaller HRNet-W32 architecture was used rather than HRNet-W48 because it was shown to provide significant speed and memory improvements for only a small reduction in accuracy. Two 5×5 transpose convolutions were added to the head of the network to match the heatmap output resolution with the resolution of the video input (FIG. 7B). Because all of the experiments had a single mouse in an open field, it was not necessary to rely on object detection for instancing. Thus, this step was eliminated from the inference algorithm, which also led to clear runtime performance benefits. Instead of performing pose estimation after object detection, full resolution pose keypoint heatmaps were used to infer the posture of a single mouse at every frame. This means that for each 480×480 frame of video 12 480×480 heatmaps were generated (one heatmap per keypoint). The maximum value in each heatmap represented the highest confidence location for each respective point. Thus, taking the argmax of each of the 12 heatmaps resulted in 12 (x, y) coordinates.

In order to train the network, it was necessary to select a loss function and an optimization algorithm. For loss, the approach used in the original HRNet description (Sun, K. et al., Proc IEEE Conf Comp Vis Pattern Recognit (2019), 5693-5703) was used. For each keypoint label, a 2D gaussian distribution centered on the respective keypoint was generated. The output of the network was then prepared with the keypoint-centered Gaussian and calculated loss as the mean squared difference between the labeled keypoint Gaussian and the heatmap generated by the network. The network was trained using the ADAM optimization algorithm which is a variant of stochastic gradient descent (Kingma, D. P. & Ba, J. (2014) arXiv:1412.6980). FIG. 7C shows that the validation loss converges rapidly. Labels were intentionally generated that represented a wide diversity of mouse appearances, including variation in coat color, body length and obesity to ensure that the resulting network operates robustly across these differences. Eight thousand nine hundred and ten (8,910) frames across these diverse strains were hand labeled for training (see Methods). The resulting network was able to track dozens of mouse strains with varying body size, shape and coat color (Geuther, B. Q. et al., Commun Biol (2019) 2:1-11).

Stride Inference

The approach to detecting stride intervals was based on the cyclic structure of gait as described by Hildebrand (FIG. 8A) (Hildebrand, M. J Mammalogy (1977) 58:131-156; Hildebrand, M. Bioscience (1989) 39:766). During a stride cycle, each of the paws has a stance phase and a swing phase (Lakes, E. H. & Allen, K. D. Osteoarthr Cartil (2016) 24:1837-1849). During the stance phase, the mouse's paw is supporting the weight of the mouse and is in static contact with the ground. During the swing phase, the paw is moving forward and is not supporting the mouse's weight. Following Hildebrand, the transition from stance phase to swing phase is referred to as the toe-off event and the transition from swing phase to stance phase is referred to as the foot-strike event.

Figure 8D:
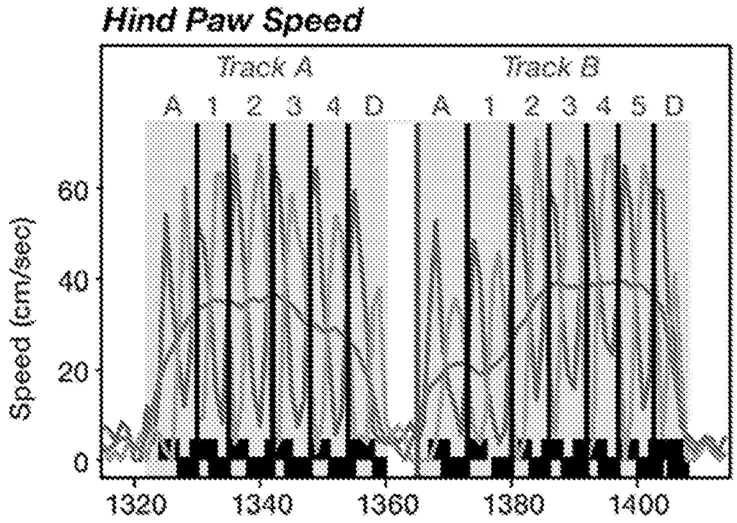
Figure 8E:
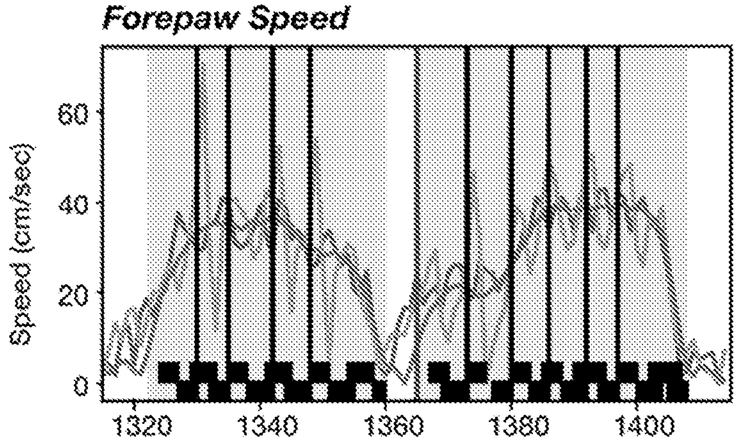
Figure 8F:
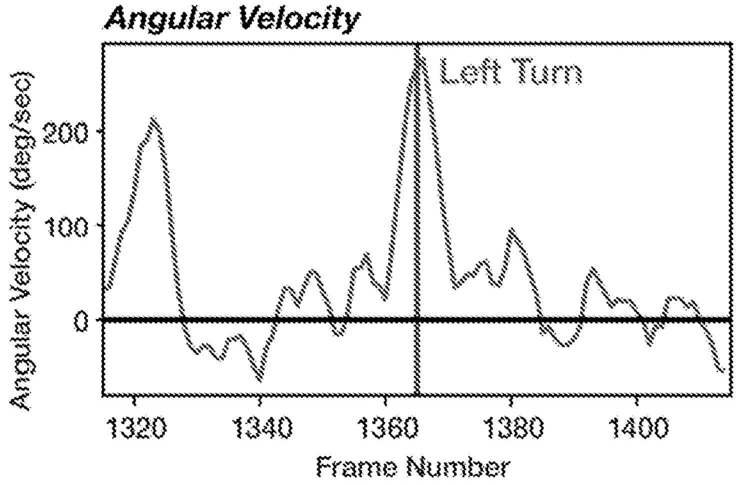
Figure 8G:
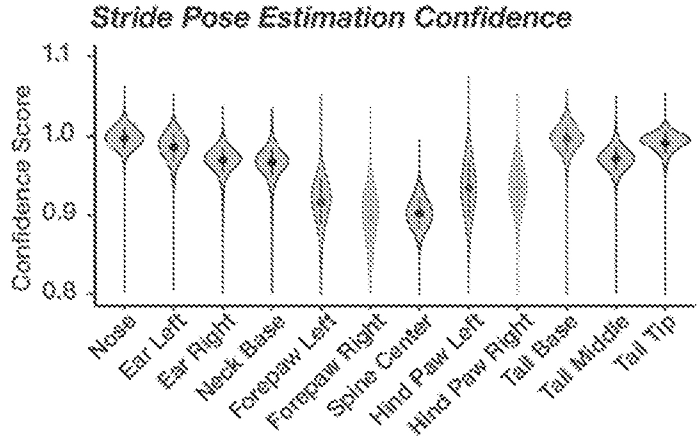

In order to calculate stride intervals, stance and swing phases were determined for the hind paws. Paw speed was calculated and it was inferred that a paw was in stance phase when the speed fell below a threshold and that it was in swing phase when it exceeded that threshold (FIG. 8C-F). It could then be determined that foot strike events occurred at the transition frame from swing phase to stance phase (FIG. 8C). The left hind foot strike was defined as the event that separates stride cycles. An example of the relationship between paw speed and foot strike events is shown in FIG. 8D for hind paws. Clean, high-amplitude oscillations of the hind paws, but not forepaws, were observed, as shown in FIG. 8E. This difference in inference quality between the forepaws and hind paws is likely due to the fact that forepaws are occluded more often than hind paws from the top-down view and are therefore more difficult to accurately locate. A corresponding decrease in confidence of forepaw inferences was observed as show in FIG. 8G. For this reason, forepaws were excluded from consideration when deriving stride intervals and instead the focus was on hind paws. A significant amount of filtering was also performed on strides to remove spurious or low quality stride cycles from the dataset (FIG. 8G). Criteria for removing strides included: low confidence or physiologically unrealistic pose estimates, missing right hind paw strike event, and insufficient overall body speed of mouse, which was any speed under 10 cm/sec. FIG. 8G shows the distribution of confidences for each keypoint. The filtering method used 0.3 as a confidence threshold. Very high confidence keypoints are close to 1.0. The first and last strides in a continuous sequence of strides were always removed to avoid starting and stopping behaviors from adding noise to the stride data (FIG. 8C-D, labeled A and D, in Track A and B). This meant that a sequence of seven strides would result in at most five strides being used for analysis. The distribution of keypoint confidence varies by keypoint type (FIG. 8G). Keypoints which tended to be occluded in a top-down view such as fore paws had confidence distributions shifted down compared to other keypoints. It was also observed that keypoints that were not visually salient, such as the spine center, would have lower confidence because they were more difficult to locate precisely. Finally, an instantaneous angular velocity was also calculated, which permitted determination of the directionality of each stride (FIG. 8F). The angular velocity was calculated by taking the first derivative of the angle formed by the line that connects the base of the mouse's tail to the base of its neck. Combined, this approach allowed identification of individual high quality strides of a mouse in the open field.

Figure 8H:
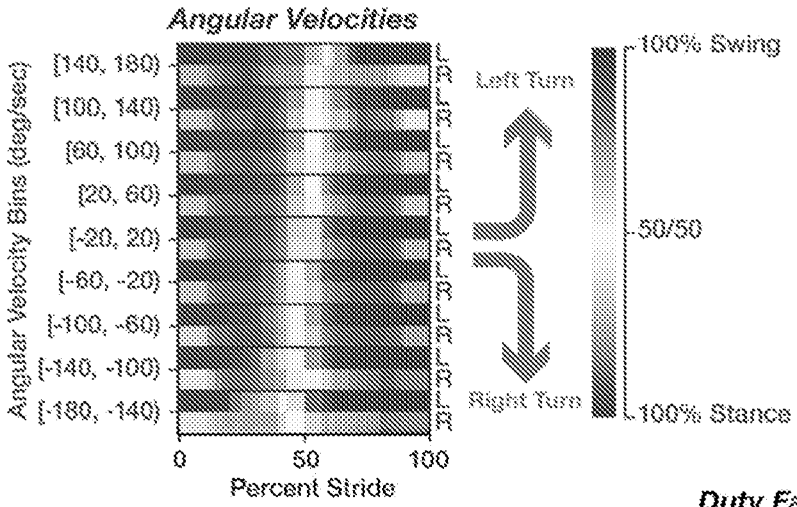
Figure 8I:
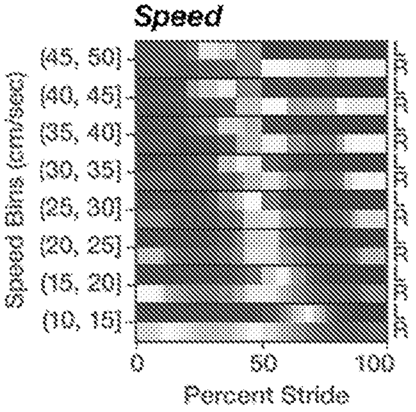
Figure 8J:
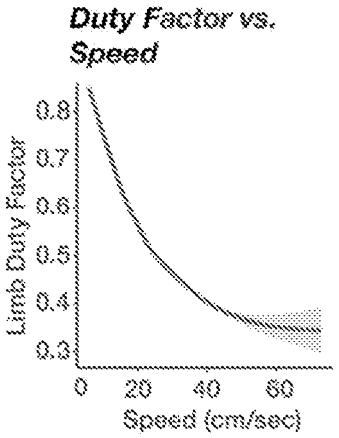

To validate that the gait quantitation was functioning properly, data from a commonly used inbred strain, C57BL/6NJ was analyzed. Percent of stance and swing were calculated from 15,667 strides from 31 animals using approximately 1-hour of open field video per mouse. Data from hind paws was analyzed because these showed the highest amplitude oscillations during stance and swing (FIG. 8D, E). The data was stratified into 9 angular velocity and 8 speed bins based on the tail base point (FIG. 8H, I, respectively). As expected, increase in stance percent over a stride of the left hind paw was determined when the animal is turning left. Reciprocally, when the animal was turning right, the stance percent of the right hind paw was increased (FIG. 8H). The strides were then analyzed in central angular velocity bin (−20 to 20 deg/sec) to determine if stance percent during a stride cycle decreased as the speed of the stride increased. It was determined that the stance time decreased as the stride speed increased (FIG. 8I). A duty factor was calculated for the hind paws to quantitate this relationship with speed (FIG. 8J). Combined, it was concluded that the methods were able to quantitatively and accurately extract strides from these open field videos from a top-down perspective.

After the stride intervals had been determined, frame poses could be used in conjunction with stance and swing phase intervals to derive several stride metrics as defined in FIG. 14A. All relevant spatiotemporal metrics were able to be extracted from the hind paws, which served as the primary data source for the statistical analyses (Lakes, E. H. & Allen, K. D. Osteoarthr Cartil (2016) 24:1837-1849).

Whole Body Posture Estimation During Gait Cycle

The top-down videos allow determination of the relative position of the spine with 6 keypoints (nose, neck base, spine center, tail base, tail middle, and tail tip). With these, the whole body pose during a stride cycle was extracted. Only three points were used (nose, base of tail, and tip of tail) to capture the lateral movement during a stride cycle (FIG. 9A-C). These measures were circular, with opposite phases of the nose and the tip of tail. For display, C57BL/6J and NOR/LtJ were used, which have different tip of tail phases during a stride cycle. It was possible to extract these phase plots for each stride, which provided high sensitivity (FIG. 9D-E). Because several hours of video were obtained across each strain, it was possible to extract thousands of strides enabling high level of sensitivity. These could be combined at one speed and angular velocity bin to determine a consensus stride phase plot for each animal and strain (FIG. 9F-G). Finally, these phase plots were compared between several strains and striking diversity was found among whole body posture during the gait cycle.

Several of the metrics related to the cyclic lateral displacement observed in pose keypoints (FIG. 9A-I). The measures of lateral displacement were defined as an orthogonal offset from the relevant stride displacement vector. The displacement vector was defined as the line connecting the mouse's center of spine on the first frame of a stride to the mouse's center of spine on the last frame of stride. This offset was calculated at each frame of a stride and then a cubic interpolation was performed in order to generate a smooth displacement curve. The phase offset of displacement was defined as the percent stride location where maximum displacement occurred on this smoothed curve. As an example, if a value of 90 for phase offset was not observed, it indicated that the peak lateral displacement occurred at the point where a stride cycle is 90% complete. The lateral displacement metric assigned to stride was the difference between maximum displacement value and minimum displacement value observed during a stride (FIG. 9A). This analysis was very sensitive and allowed detection of subtle, but highly significant difference is overall posture during a stride. The previous classical spatiotemporal measures based on Hildebrand's methods were used with the combined whole body posture metrics for the analysis. Because of the cyclic nature of phase-offset metrics, care was taken to apply circular statistics to these in the analysis. The other measures were analyzed using linear methods.

Statistical Analysis and Genetic Validation of Gait Measures

Following gait and posture extraction, a statistical framework was established for analysis of the data. In order to validate the methods, three mouse models were phenotyped, each having been previously been shown to have gait defects and to be a preclinical mode; of a human disease—Rett's syndrome, Amyotrophic Lateral Sclerosis (ALS or Lou Gehrig's disease), and Down syndrome. The three models, Mecp2 knockout, SOD1 G93A transgene, and Ts65Dn Trisomic, respectively, were tested with appropriate controls at two ages in a one hour open field assay (FIG. 14B). Gait metrics are highly correlated with animal size and speed of stride (Hildebrand, M. Bioscience (1989) 39:766) (FIG. 8I-J). However, in many cases a change in stride speed is a defining feature of gait change due to genetic or pharmacological perturbation. In addition, the methods were used to collect multiple repeated measurements for each subject (mouse) and each subject had a different number of (strides) giving rise to imbalanced data. Averaging over repeated strides, which yields one average value per subject, can be misleading as it removes variation and introduces false confidence. At the same time, classical linear models do not discriminate between stable intra-subject variations and inter-subject fluctuations, which severely bias the estimates. To address this, a linear mixed model (LMM) was used to dissociate within-subject variation from genotype-based variation between subjects (Laird, N. M. & Ware, J. H., Biometrics (1982) 38:963-974; Pinheiro, J. & Bates, D. Mixed-effects models in S and S-PLUS, New York: Springer-Verlag, 2000). Specifically, in addition to the main effects such as animal size, genotype, age, a random effect that captures the intra-subject variation is included. Finally, multiple repeated measurements have been taken at two different ages giving rise to a nested hierarchical data structure. The models (M1, M2 M3) follow the standard LMM notation with (Genotype, BodyLength, Speed, TestAge) denoting the fixed effects and (MouseID/TestAge) (test age nested within the animal) denoting the random effect. In order to compare the results with previously published data that do not take animal size and sometimes speed of stride into account, the results were statistically modeled with three models that only take age and body length (M1), age and speed (M2), age, speed, and body length (M3) (FIGS. 10 and 14). The models were: M1: Phenotype~Genotype+TestAge+BodyLength+(1|MouseID/TestAge); M2: Phenotype~Genotype+TestAge+Speed+(1|MouseID/TestAge); and M3: Phenotype~Genotype+TestAge+Speed+BodyLength+(1|MouseID/TestAge).

Sex was not included in the models as it is highly correlated with body length (measured using ANOVA and denoted by $\eta$, is strong for both SOD1 ($\eta$=0.81) and Ts65Dn ($\eta$=0.16 overall, $\eta$=0.89 for controls, $\eta$=0.61 for mutants). The Mecp2 males and females were analyzed separately. The circular phase variables in FIG. 14A were modeled as a function of linear variables using a circular-linear regression model (Fisher, N. I. & Lee, A. J., Biometrics (1992)

48:665-677). To adjust for linear variables such as body length and speed, they were included as covariates in the model (also see Methods). FIGS. 10 and 11 report p-values and normalized effect size. For clarity, exact statistics are reported in detail in FIGS. 19 and 20.

Validation Using a Rett Syndrome Model

Rett syndrome, an inherited neurodevelopmental disorder, is caused by mutations in the X-linked MECP2 gene (Amir, R. E. et al., Nat Genet (1999) 23:185-188). Studies included a commonly studied deletion of Mecp2 that recapitulates many of the features of Rett syndrome, including reduced movement, abnormal gait, limb clasping, low birth weight, and lethality (Guy, J. et al., Nature Genet, (2001) 27:322-326). Hemizygous males (n=8), heterozygous females (n=8), and littermate controls (n=8 of each sex) were tested (FIG. 14B). Null males are normal at birth and have an expected lifespan of about 50-60 days. They start to show age-dependent phenotypes by 3-8 weeks and lethality by 10 weeks. Heterozygous females have mild symptoms at a much older age (Guy, J. et al., Nature Genet, (2001) 27:322-326). Male mice were tested twice at 43 and 56 days and females at 43 and 86 days.

Figure 10A:
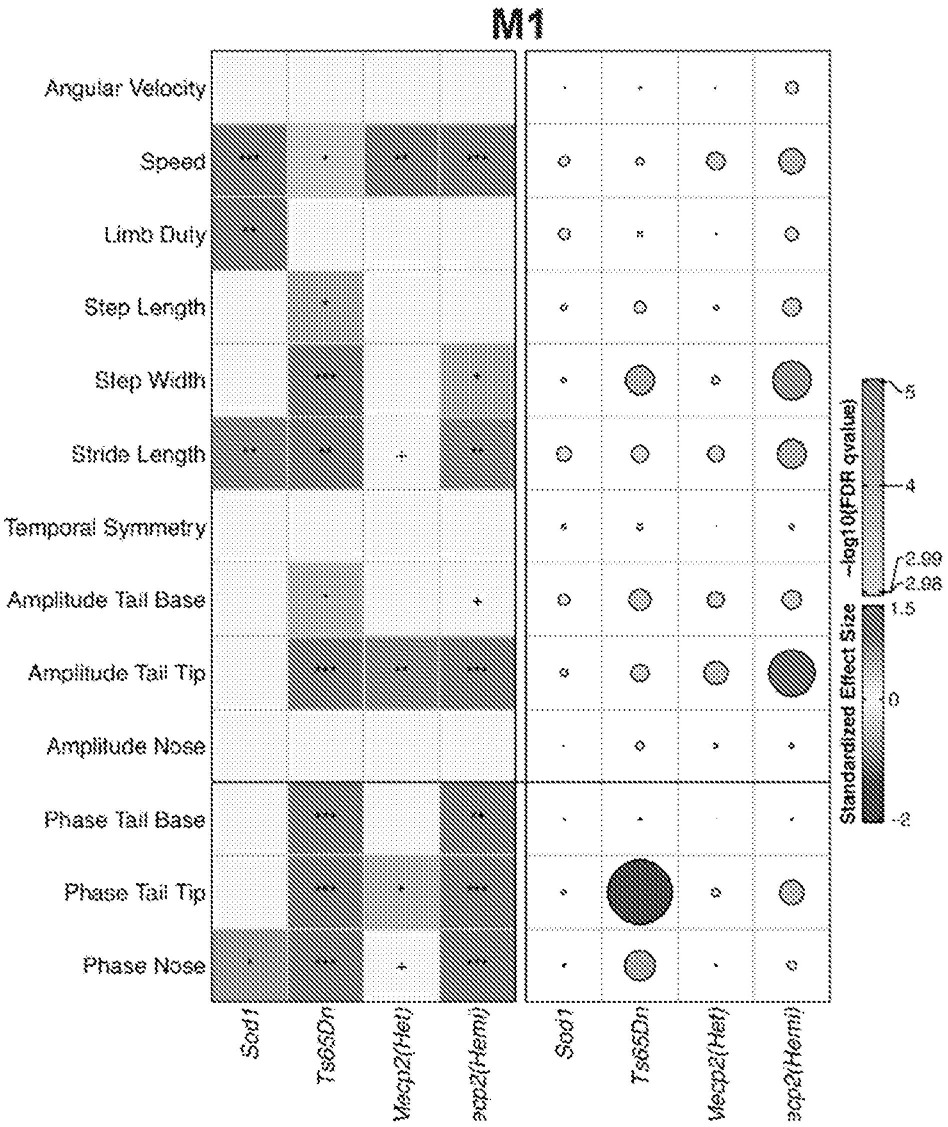
FIG. 10A-E shows results indicating genetic validation of gait mutants.
Figure 10B:
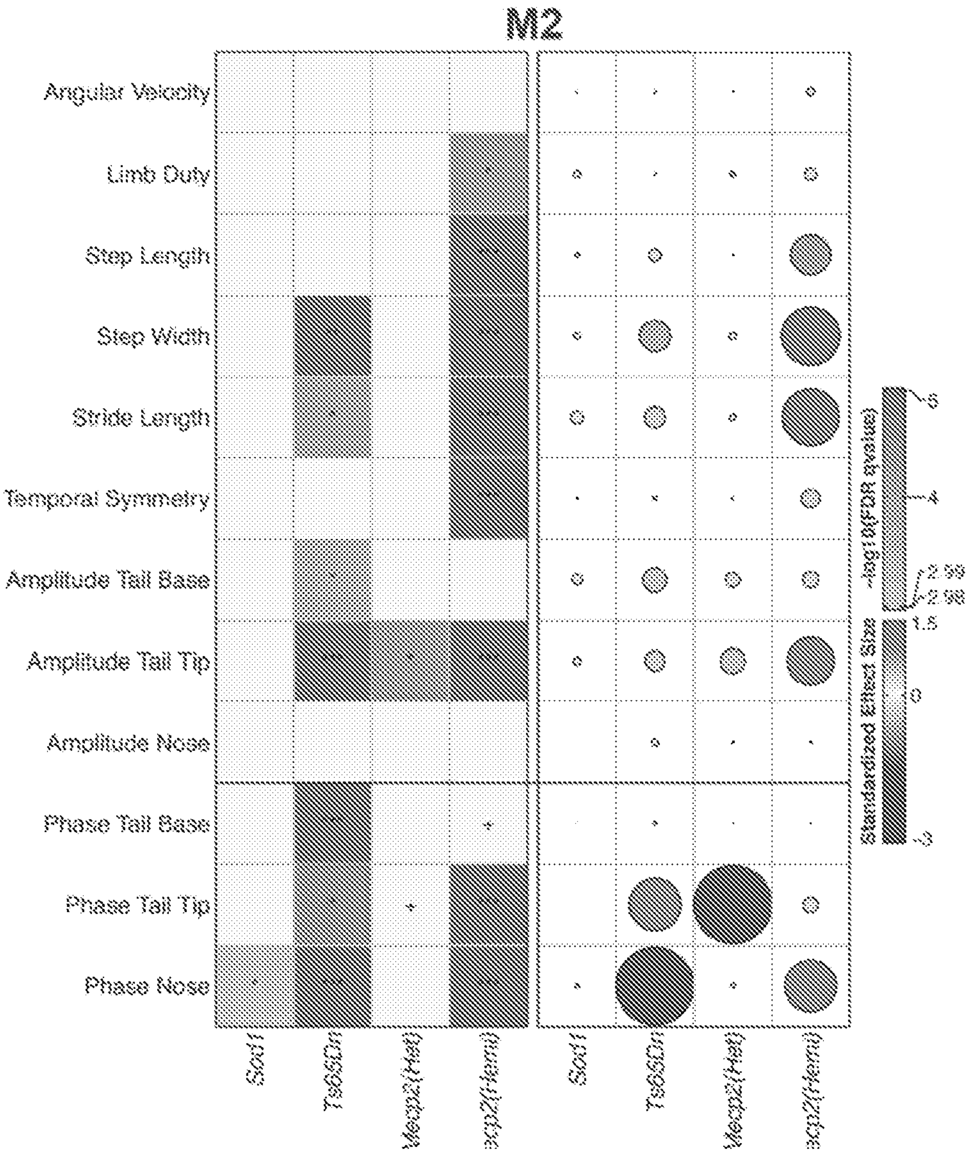
Figure 10C:
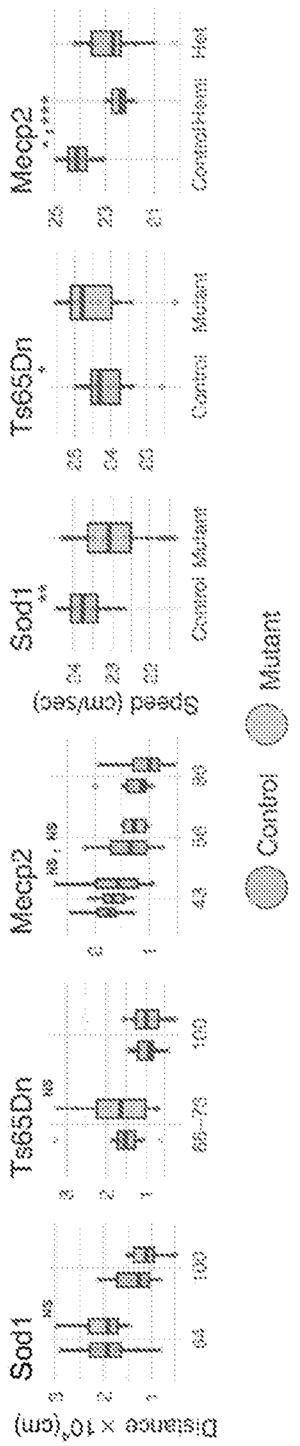
Figure 10D:
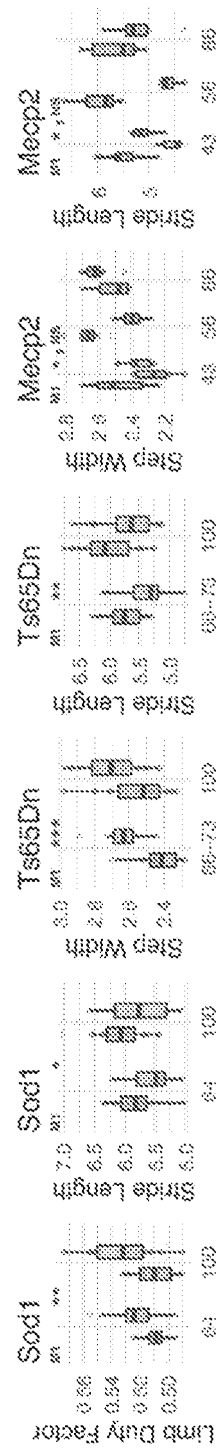

Studies of this knockout have shown changes in stride length and stance width in an age-dependent manner in hemizygous males (Kerr, B. et al., PLoS One (2010) 5(7): e11534; (2010); Robinson, L. et al., Brain (2012) 135:2699-2710). Recent analysis showed increased step width, reduced stride length, changes in stride time, step angle, and overlap distance (Gadalla, K. K. et al., PloS One (2014) 9(11):e112889). However, these studies did not adjust for the reduced body size seen in Mecp2 hemizygous males (FIG. 14D) and in some cases did not model speed of the stride. The most relevant comparison of the experimental data obtained to previously published data was using M2, which models speed but not body length (Gadalla, K. K. et al., PloS One (2014) 9(11):e112889; FIG. 14D). It was found that most of the gait metrics and several body coordination metrics were significantly different in the hemizygous males versus controls including limb duty factor, step and stride length, step width and temporal symmetry. However, most gait metrics are dependent on the size of the animal and the hemizygous males are 13% smaller in body length (FIG. 14D) (Guy, J. et al., Nature Genet, (2001) 27:322-326). In addition, the analysis was limited to stride speeds between 20-30 cm/s which allowed reduction in variation introduced by differences in speed. Therefore, a model that includes body length instead of speed as a covariate (M1, FIG. 10A) and one in which both body length and speed are included (M3, FIG. 15A) were also compared. Results of M2 model indicated significant difference in stride speed, step width, stride length, whole body coordination phenotypes (tail tip amplitude, phase of tail tip and nose) in hemizygous males (FIG. 10B). Most phenotypes were dependent on age with severe effects in males by 7 weeks (56 days) (FIG. 10D). The model that includes both speed and body length (M3) showed a significant decrease in step width and suggestive difference in stride length, and robust differences in whole body coordination metrics (tail tip amplitude, phase of tail tip, tail base, and nose) (FIG. 15). Very few significant differences were observed in Mecp2 heterozygous females and they were consistent across all three models. All three models consistently find tail tip amplitude to be significantly higher suggesting more lateral movement in the females (FIG. 10A-B and FIG. 15). Combined, these results demonstrated that the method permitted accurate detection of previously described differences in Mecp2. In addition, the whole body coordination metrics were able to detect differences that had not been previously described.

Validation Using an ALS Model

Mice carrying the SOD1-G93A transgene are a preclinical model of ALS with progressive loss of motor neurons (Gurney, M. E. et al., Science (1994) 264:1772-1775; Rosen, D. R. et al., Nature (1993) 362:59-62). The SOD1-G93A model has been shown to have changes in gait phenotypes, particularly of hindlimbs (Wooley, C. M. et al., Muscle & Nerve (2005) 32:43-50; Amende, I. et al., J Neuroeng Rehabilitation (2005) 2:20; Preisig, D. F. et al., Behavioural Brain Research (2016) 311:340-353; Tesla, R. et al., PNAS (2012) 109:17016-17021; Mead, R. J. et al., PLoS ONE (2011) 6:e23244; Vergouts, M. et al., Metabolic Brain Disease (2015) 30:1369-1377; Mancuso, R. et al., Brain Research (2011) 1406:65-73). The most salient phenotypes are an increase in stance time (duty factor), and decreased stride length in an age-dependent manner. However, several other studies have observed opposite results (Wooley, C. M. et al., Muscle & Nerve (2005) 32:43-50; Amende, I. et al., J Neuroeng Rehabilitation (2005) 2:20; Mead, R. J. et al., PLoS ONE (2011) 6:e23244; Vergouts, M. et al., Metabolic Brain Disease (2015) 30:1369-1377), and some have not seen significant gait effects (Guillot, T. S. et al., Journal of Motor Behavior (2008) 40: 568-577). These studies did not adjust for body size difference or in some cases for speed. SOD1-G93A transgenes and appropriate controls were tested at 64 and 100 days, during time of disease onset (Wooley, C. M. et al., Muscle & Nerve (2005) 32:43-50; Preisig, D. F. et al., Behavioural Brain Research (2016) 311:340-353; Vergouts, M. et al., Metabolic Brain Disease (2015) 30:1369-1377; Mancuso, R. et al., Brain Research (2011) 1406:65-73; Knippenberg, S. et al., Behavioural Brain Research (2010) 213: 82-87).

Surprisingly, it was found that the phenotypes differing between transgene carriers and controls varied considerably depending on the linear mixed model used. M1, which adjusts for body length and age but not speed, finds stride speed, length, and duty factor as significantly different (FIG. 10A). However, when speed was in the model (M2) or speed and body length were in the model (M3), the only differences were small changes in phase of tail tip and nose (FIGS. 10B and 15). This indicated that the changes seen in duty factor and stride length using M1 are due to changes in speed of the strides. These results argue that the major effect of the SOD1 transgene is on stride speed, which leads to changes in stride time and duty factor. Slight changes in whole body coordination are due to decrease in body size (FIG. 14D). The results were congruent with reports that gait changes may not be the most sensitive preclinical phenotype in this ALS model, and other phenotypes such as visible clinical signs and motor learning tasks such as rotarod are more sensitive measures (Mead, R. J. et al., PLoS ONE (2011) 6:e23244; Guillot, T. S. et al., Journal of Motor Behavior (2008) 40: 568-577). In sum, the testing results validated the statistical model and may help explain some of the discordant results in the literature.

Validation Using a Down Syndrome Model

Down syndrome, caused by trisomy of all or part of chromosome 21, has complex neurological and neurosensorial phenotypes (Haslam, R. H. Down syndrome: living and learning in the community. New York: Wiley-Liss, 107-14 (1995)). Although there are a spectrum of phenotypes such as intellectual disability, seizures, strabismus, nystagmus, and hypoacusis, the more noticeable phenotypes are developmental delays in fine motor skills (Shumway-Cook, A. & Woollacott, M. H. Physical Therapy 65:1315-

1322 (1985); Morris, A. et al., Journal of Mental Deficiency Research (1982) 26:41-46). These are often described as clumsiness or uncoordinated movements (Vimercati, S. et al., Journal of Intellectual Disability Research (2015) 59:248-256; Latash, M. L. Perceptual-motor behavior in Down Syndrome (2000) 199-223). One of the best studied models, Tn65Dn mice are trisomic for a region of mouse chromosome 16 that is syntenic to human chromosome 21 and recapitulate many of the features of Down syndrome (Reeves, R. et al., Nat Genet (1995) 11:177-184; Herault, Y. et al., Dis Model Mech (2017) 10:1165-1186). Tn65Dn mice have been studied for gait phenotypes using traditional inkblot footprint analysis or treadmill methods (Hampton, T. G. and Amende, I. J Mot Behav (2009) 42:1-4; Costa, A. C. et al., Physiol Behav (1999) 68:211-220; Faizi, M. et al., Neurobiol Dis (2011) 43, 397-413). The inkblot analysis showed mice with shorter and more "erratic" and "irregular" gait, similar to motor coordination deficits seen in patients (Costa, A. C. et al., Physiol Behav (1999) 68:211-220). Treadmill-based analysis revealed further changes in stride length, frequency, some kinetic parameters, and foot print size (Faizi, M. et al., Neurobiol Dis (2011) 43, 397-413; Hampton, T. G. et al., Physiol Behav (2004) 82:381-389). These previous analyses have not studied the whole body posture of these mice.

Figure 10E:
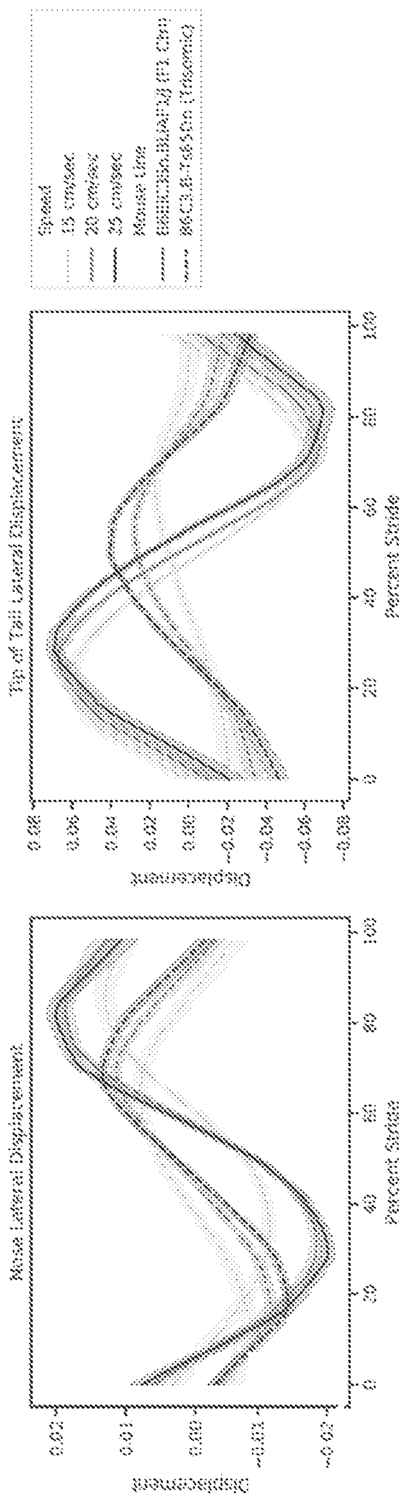
Figures 15A, 15B:
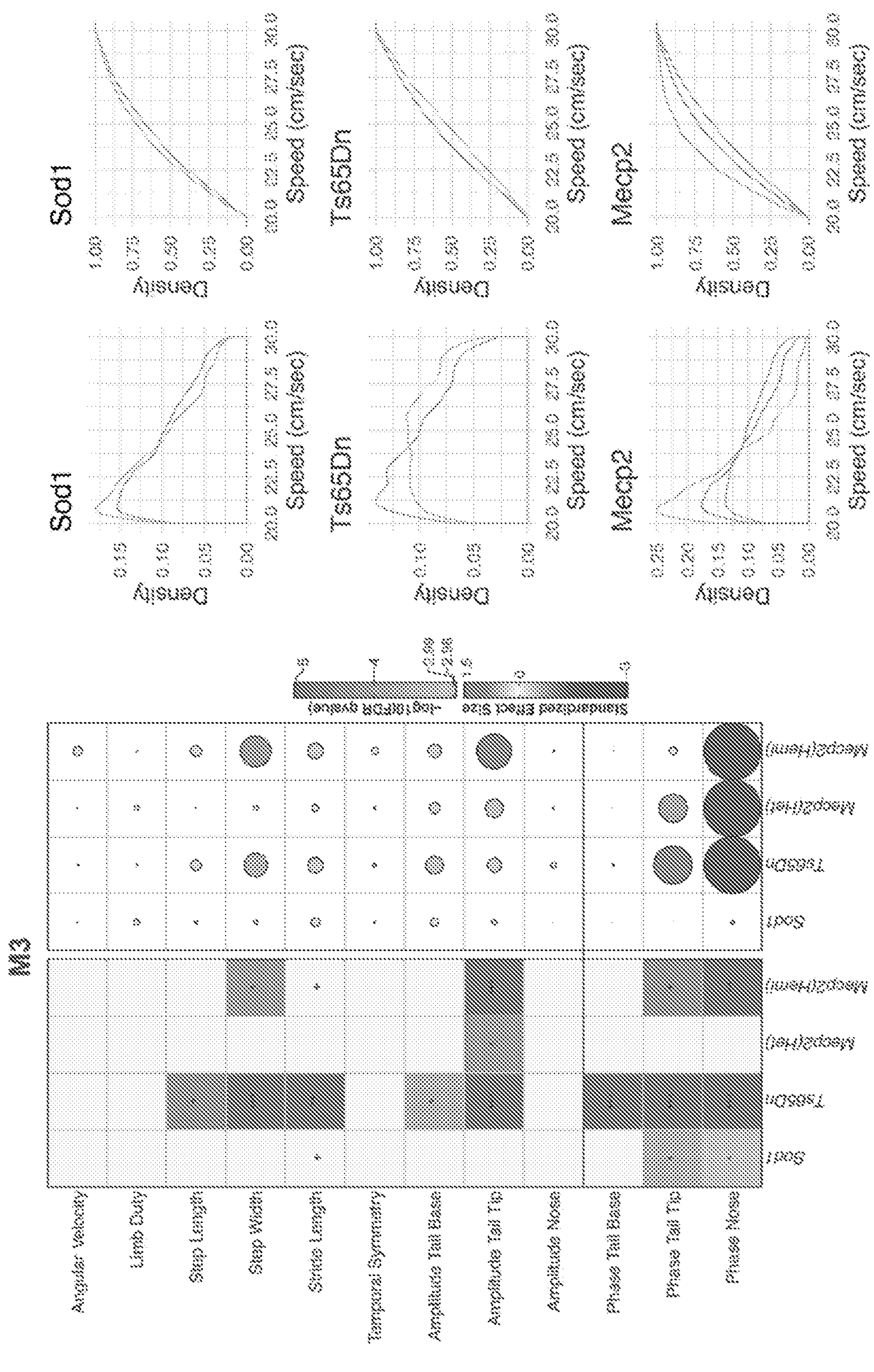
FIG. 15A-E provides heat maps, curves, and plots.
Figure 15C:
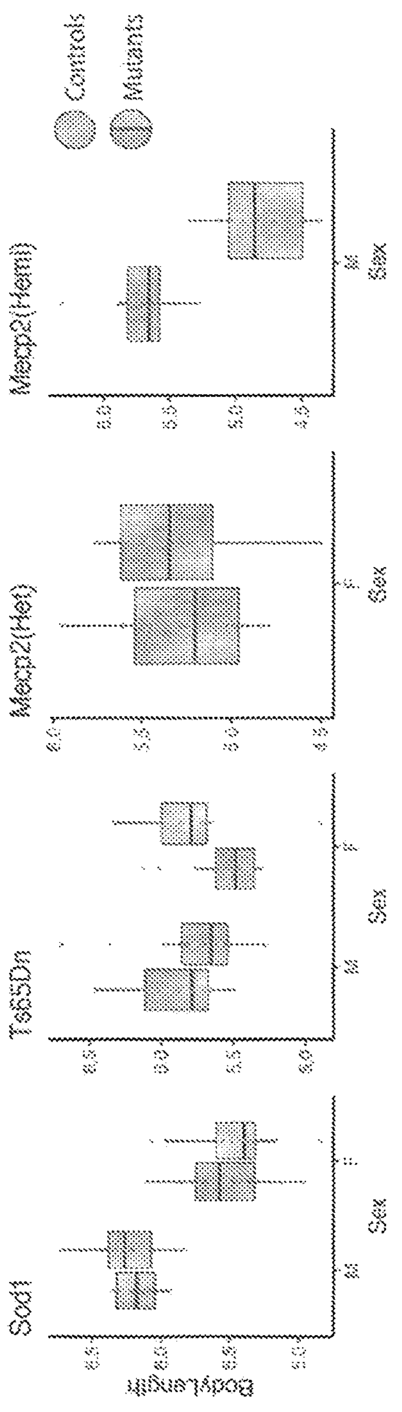
Figure 15D:
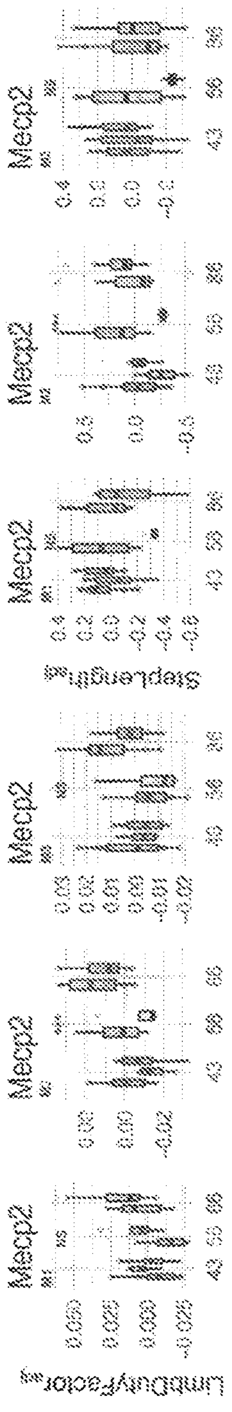
Figure 15E:
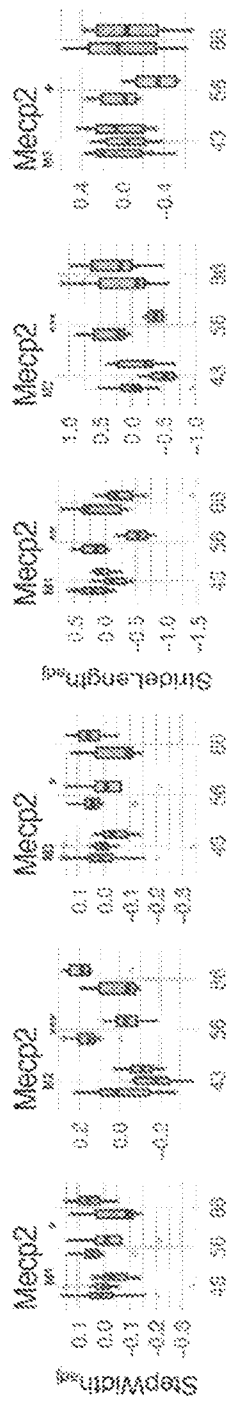

Using methods of the invention, Tn65Dn mice were analyzed along with control mice at approximately 10 and 14 weeks (FIG. 14B) and all three linear mixed models M1-M3 found consistent changes. The Ts65Dn mice are not hyperactive in the open field (FIG. 10C), although they have increased stride speed (FIG. 10A, C). This indicated that the Tn65Dn mice take quicker steps but travel the same distance as controls. Step width was increased and step and stride lengths were significantly reduced. The most divergent results from controls are obtained with M3, which accounts for speed and body length. In particular, whole body coordination phenotypes were highly affected in the Tn65Dn mice. The amplitude of tail base and tip, and the phase of tail base, tip, and nose were significantly decreased (FIG. 15A). The results confirmed this with a phase plot of nose and tail tip (FIG. 10E). Surprisingly, it was found that there were large differences in phase. The tail tip phase peak was near 30% of the stride cycle in controls and close to 60% in mutants at multiple speeds (FIG. 10E). Similar changes were seen in the phase plot for the nose. Combined, these results confirmed previous reported differences in traditional gait measures, and highlight the utility of the novel open field whole body coordination measures in broadening the assayable phenotypic features in models of human disease. Indeed, the most salient feature of the Tn65Dn gait was the alteration of whole body coordination, which previously was reported as a qualitative trait using inkblot analysis (Costa, A. C. et al., Physiol Behav (1999) 68:211-220) and is now quantifiable using methods of the invention.

Characterization of Autism Spectrum Disorder-Related Mutants

To further validate the analysis approach, gait was investigated in four autism spectrum disorder (ASD) mouse models, in addition to Mecp2 above that also falls on this spectrum. In humans, gait and posture defects are often seen in ASD patients and sometimes gait and motor defects precede classical deficiencies in verbal and social communication and stereotyped behaviors (Licari, M. K. et al., Autism Research (2020) 13:298-306; Green et al., Dev Med Child Neurol (2009) 51:311-316). Recent studies indicate that motor changes are often undiagnosed in ASD cases (Hughes, V. Motor problems in autism move into research focus. Spectrum News (2011)). It is unclear if these differences have genetic etiologies or are secondary to lack of social interactions that may help children develop learned motor coordination (Zeliadt, N., Autism in motion: Could motor problems trigger social ones. Scientific American, Spectrum, Mental Health (2017)). In mouse models of ASD, gait defects have been poorly characterized, and thus studies were performed to determine if any gait phenotypes occur in four commonly used ASD genetic models, which were characterized with appropriate controls at 10 weeks (FIG. 14C). Similar to the three models with known gait defects, these mutants and controls were tested in the one hour open field assay and gait and posture metrics were extracted (FIG. 14A). The results were modeled using the same approach used for gait mutants (M1 and M3 results are presented in FIG. 11, M2 results are in FIG. 16).

Figure 16B:
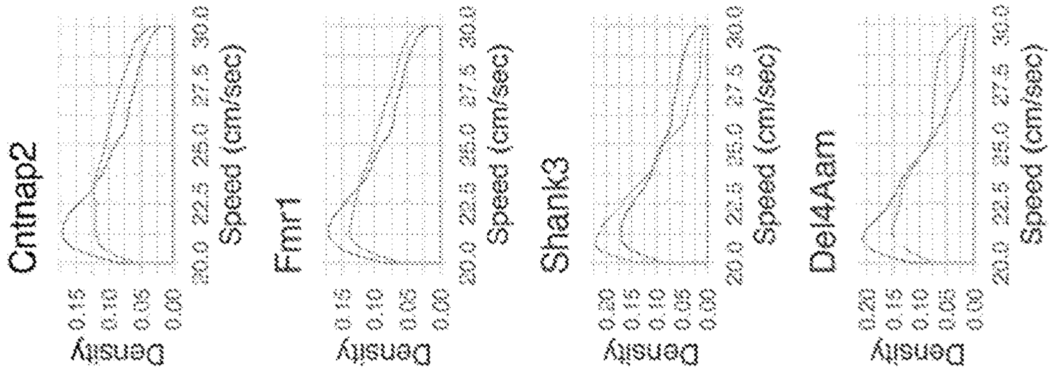
FIG. 16A-E provides heat maps, curves and plots.
Figure 16A:
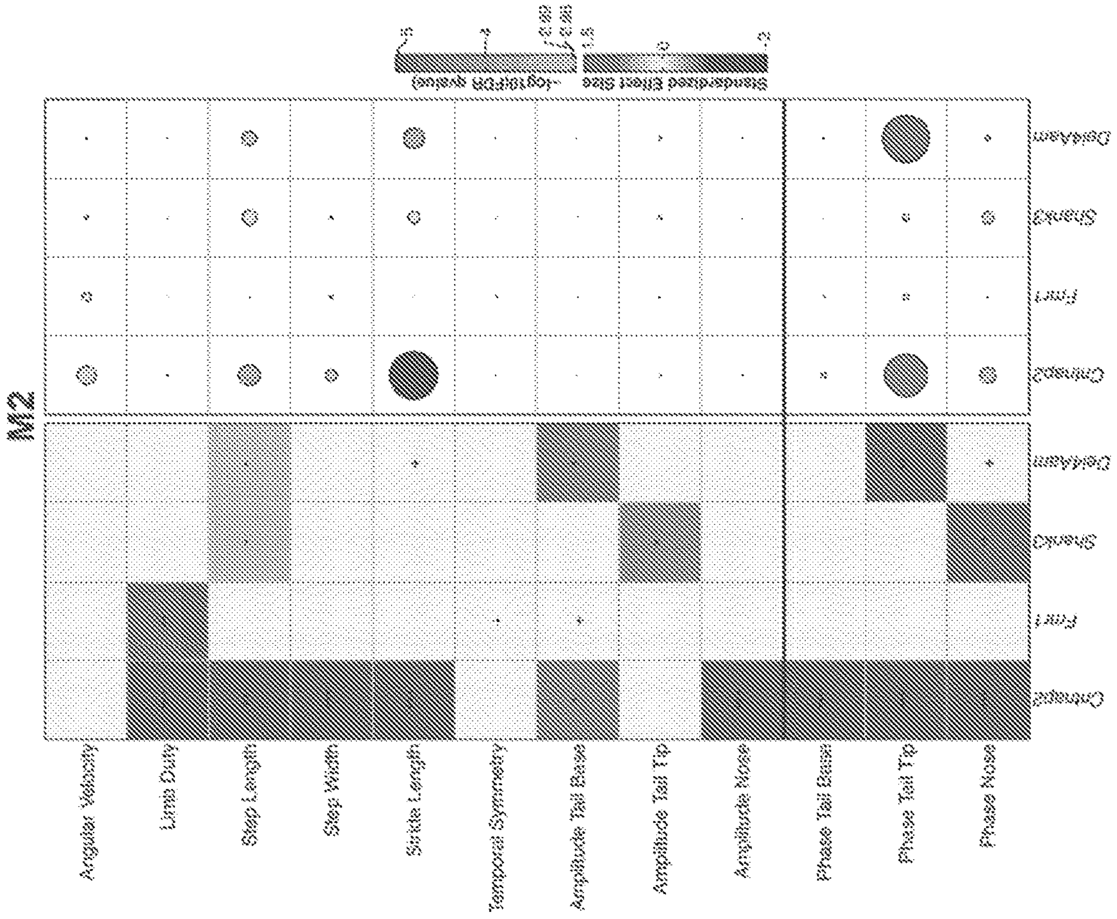
Figure 16C:
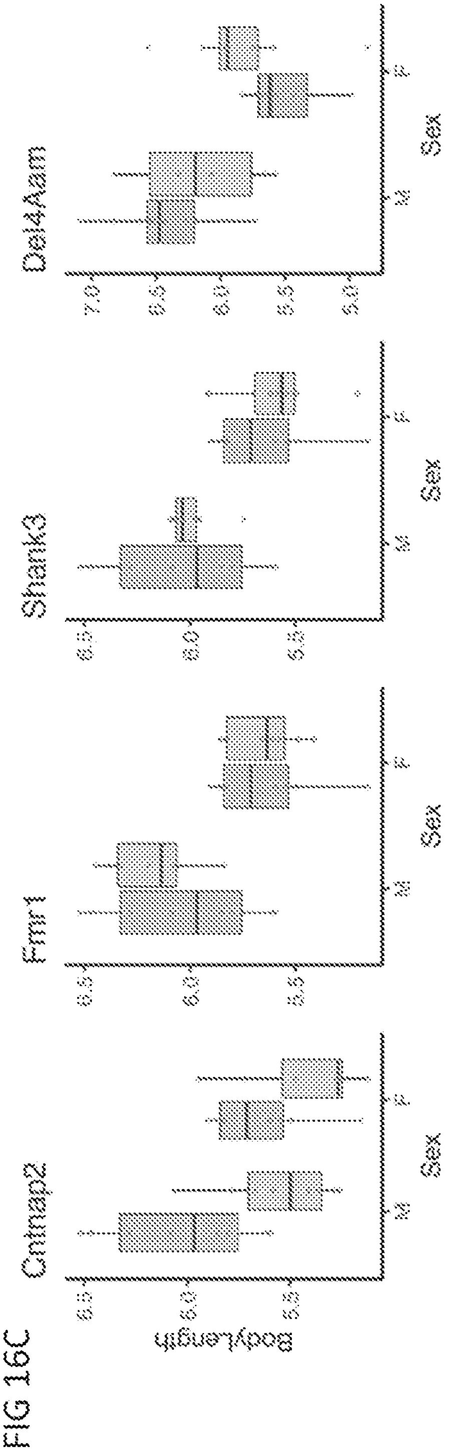
Figure 16D:
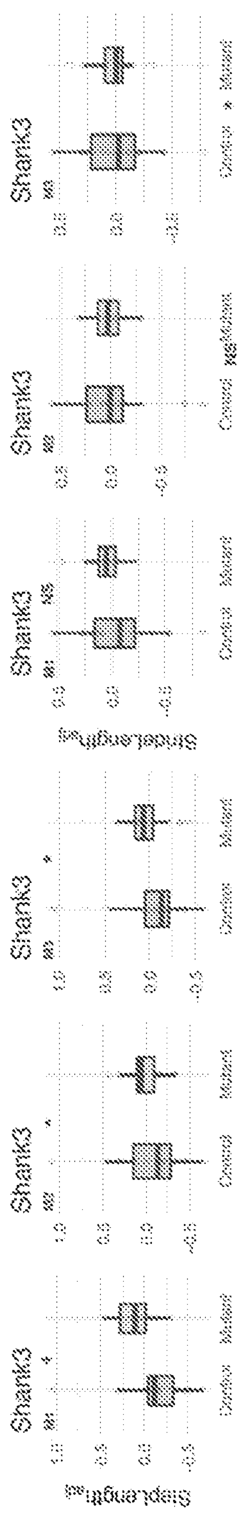
Figure 16E:
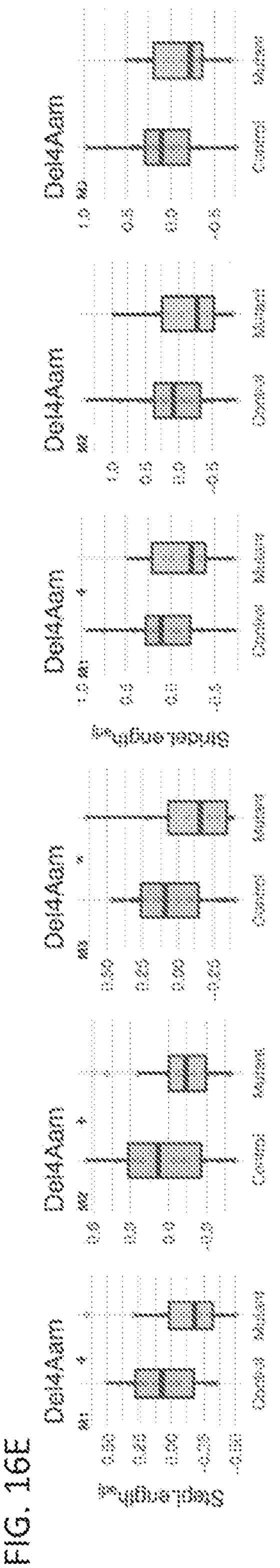
Figure 17A:
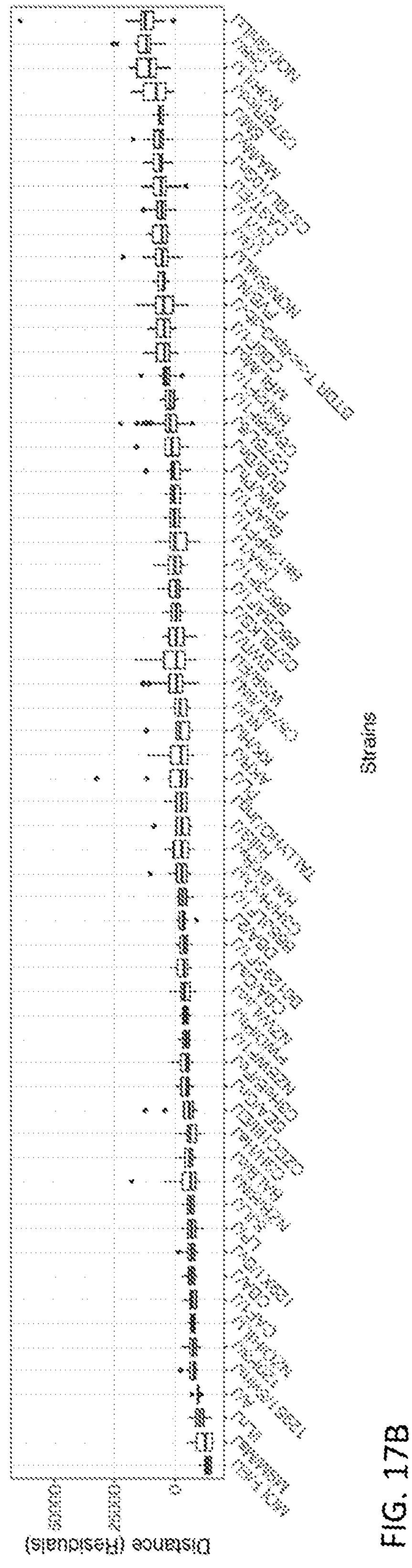
FIG. 17A-F shows results of body length adjusted phenotypes that were compared across 62 strains in the strain survey. The box plots are displayed in an ascending order with respect to the median measure from left to right. Each panel (FIG. 17A-F) corresponds to a different gait phenotype.
Figure 17B:
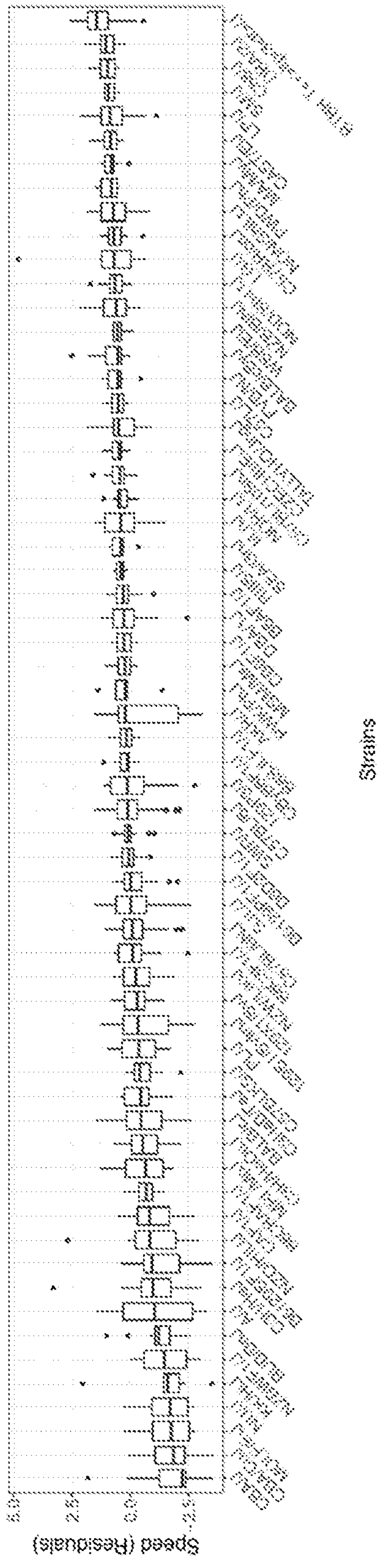
Figure 17C:
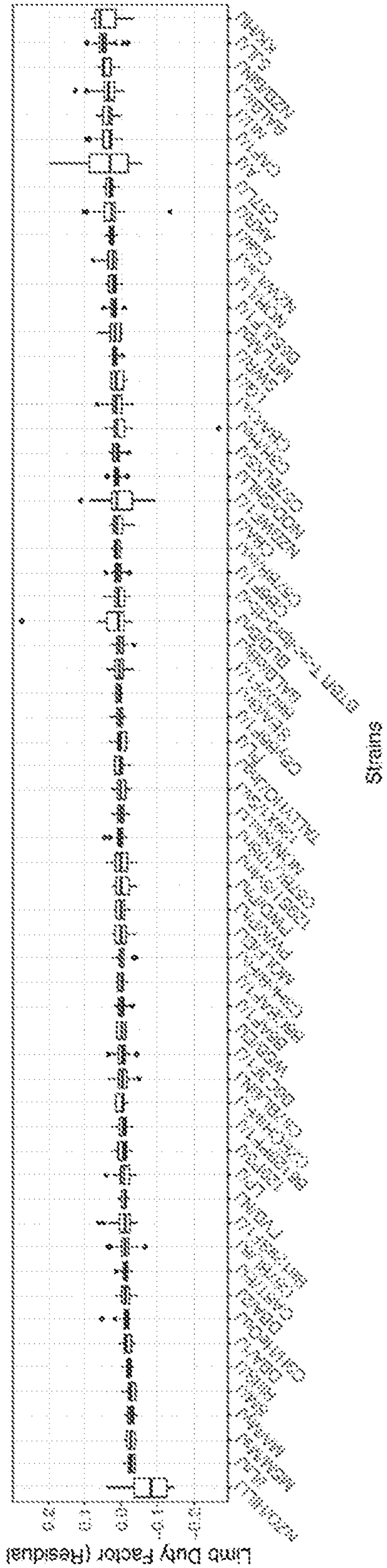
Figure 17D:
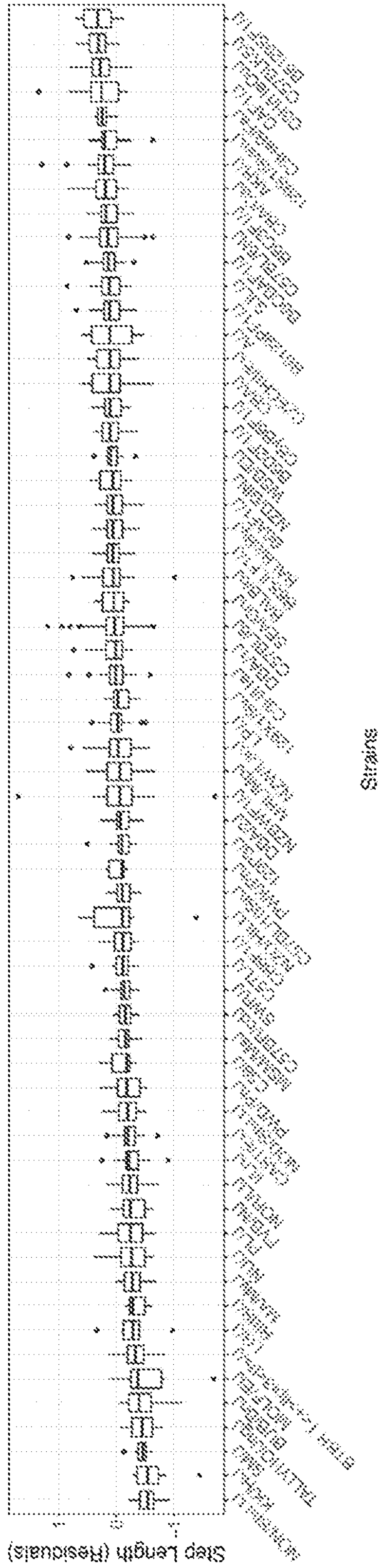
Figure 17E:
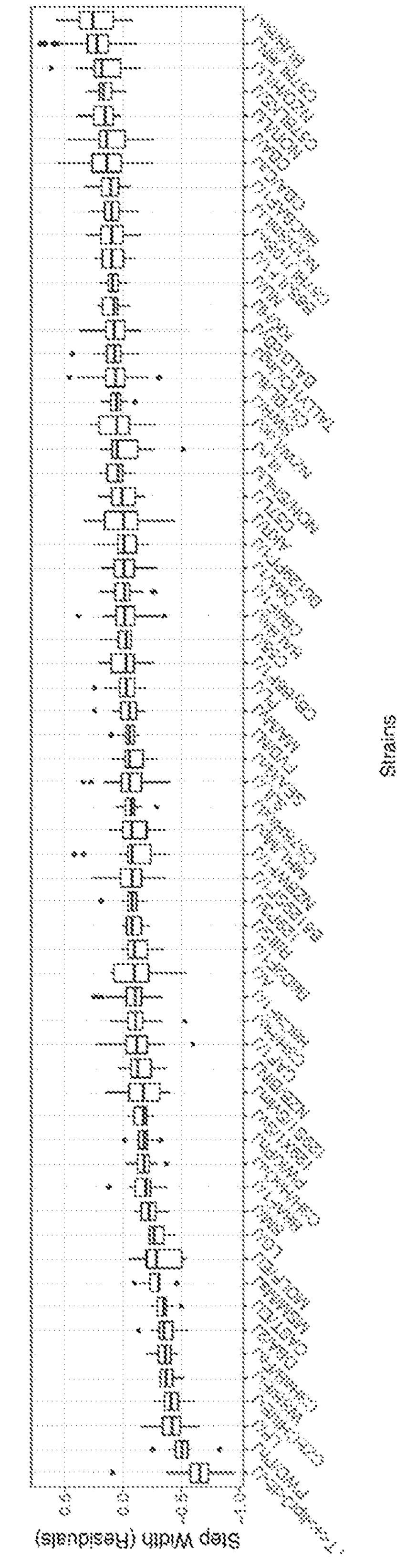
Figure 17F:
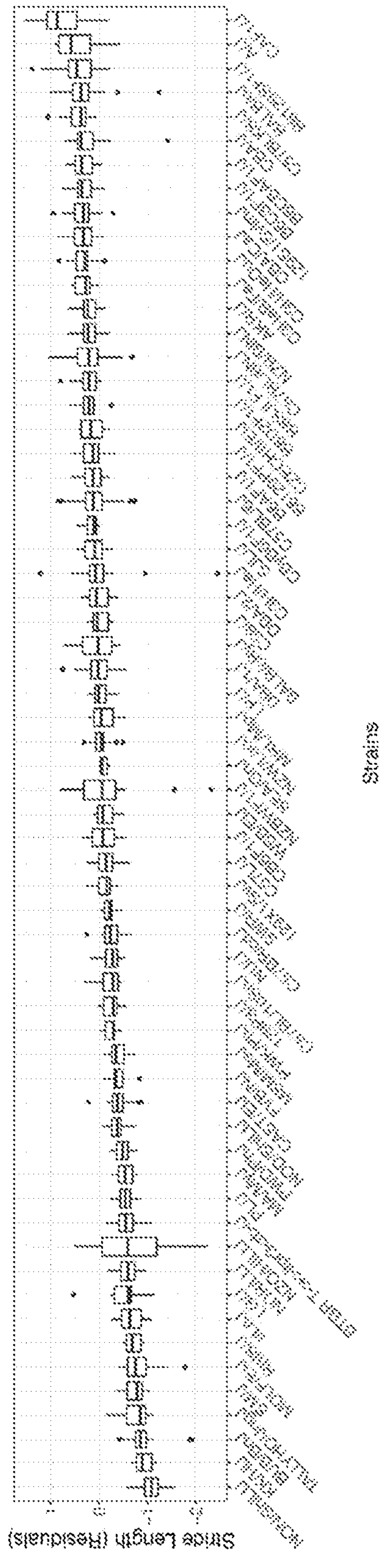
Figure 18A:
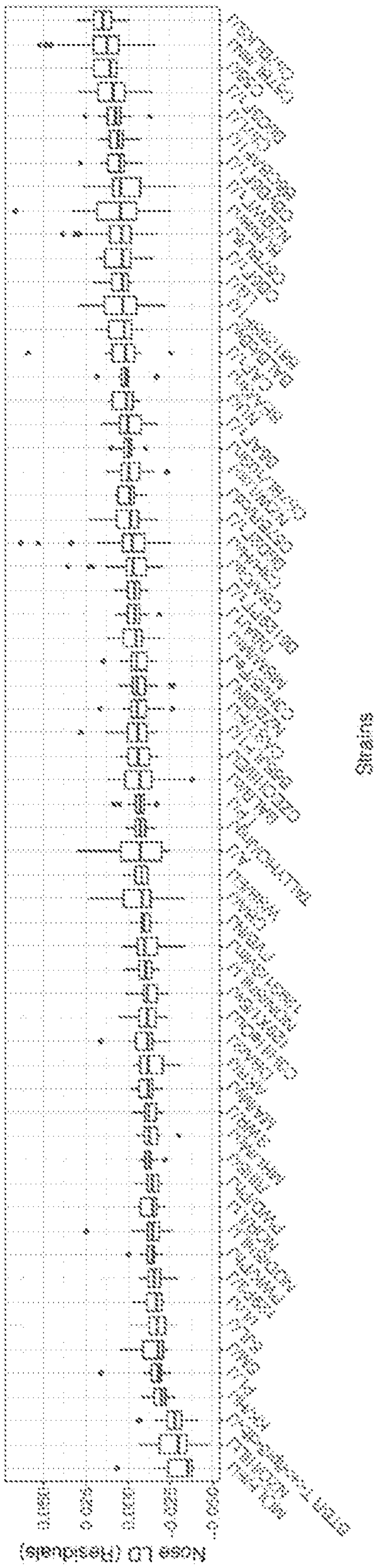
FIG. 18A-E shows results of body length adjusted phenotypes that were compared across 62 strains in the strain survey. The box plots are displayed in an ascending order with respect to the median measure from left to right. Each panel (FIG. 18A-E) corresponds to a different gait phenotype.
Figure 18B:
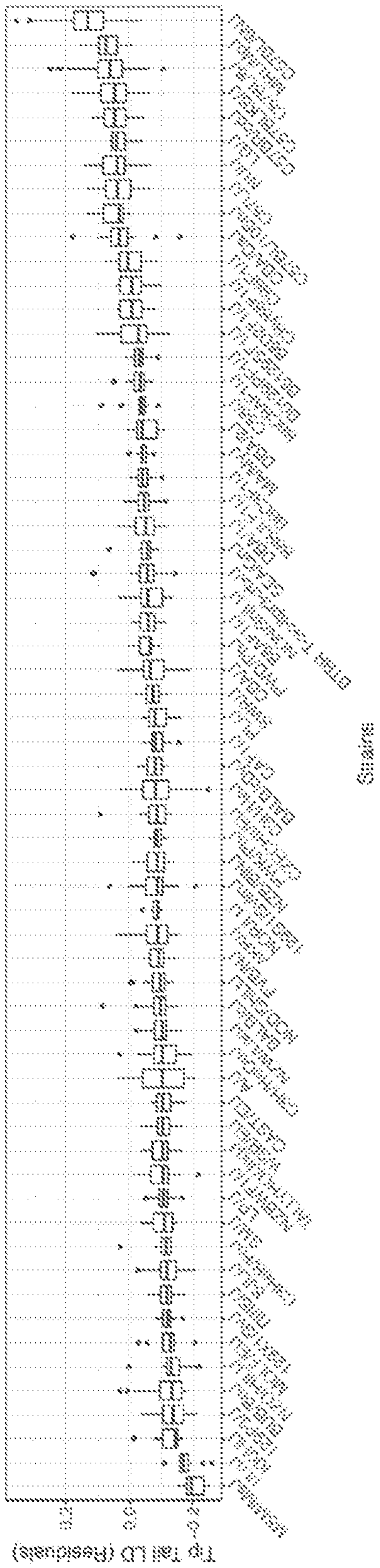
Figure 18C:
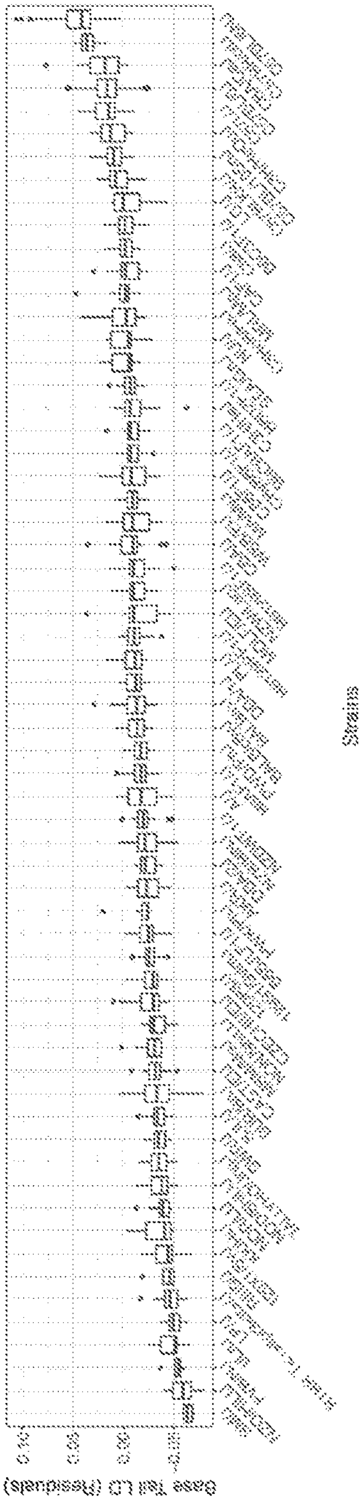
Figure 18D:
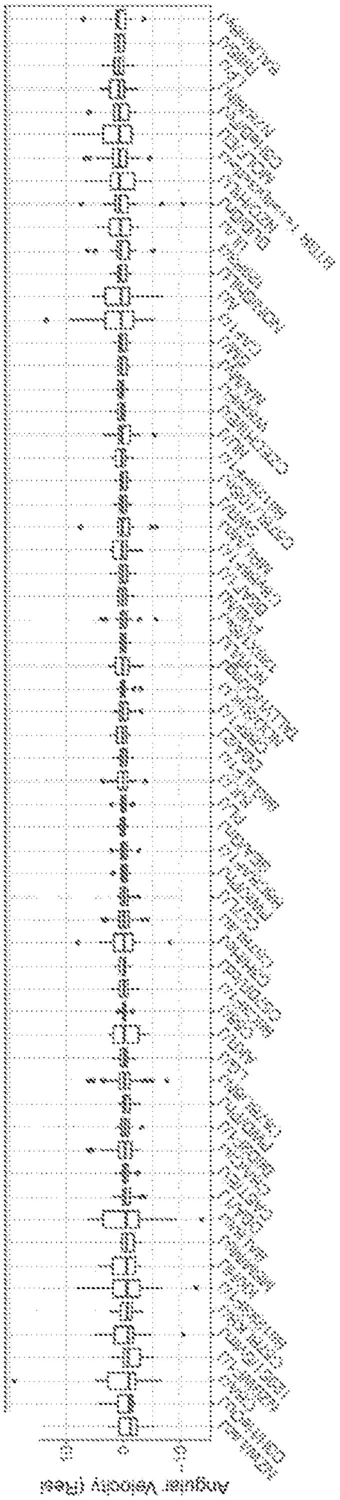
Figure 18E:
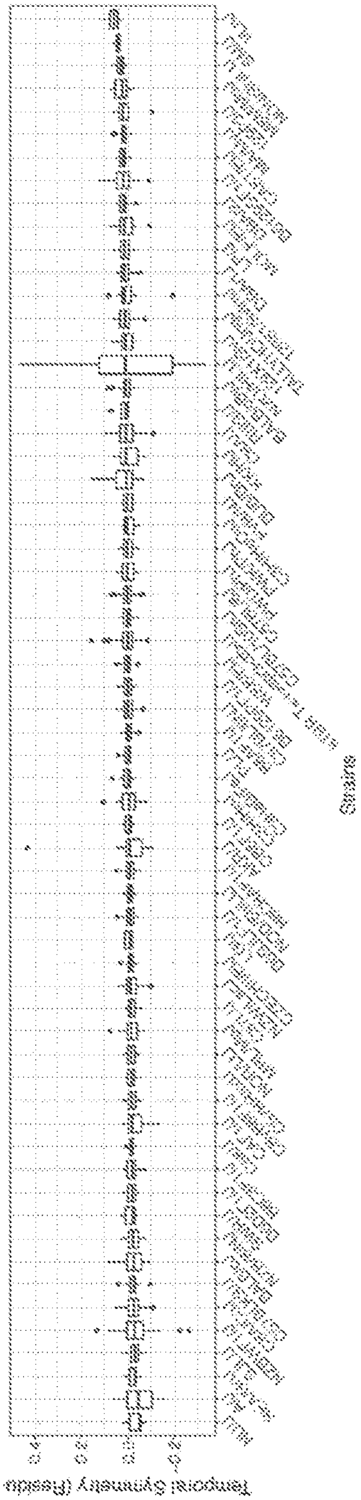
Figure 21A:
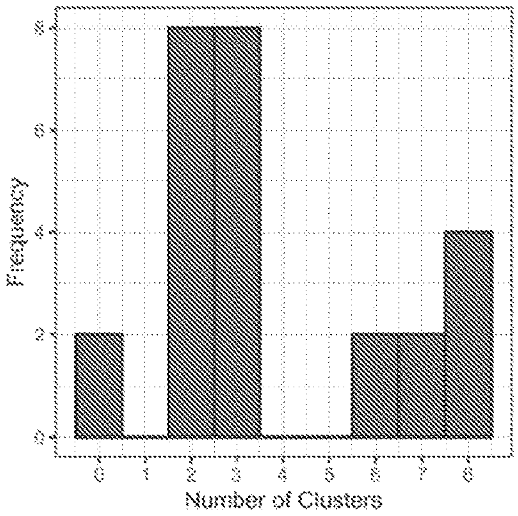
FIG. 21A-D shows three optimal clusters in strain survey data. Thirty clustering indices were examined for choosing the optimal number of clusters (Bates et al., J Stat Softw (2015) 67:1).
Figure 21B:
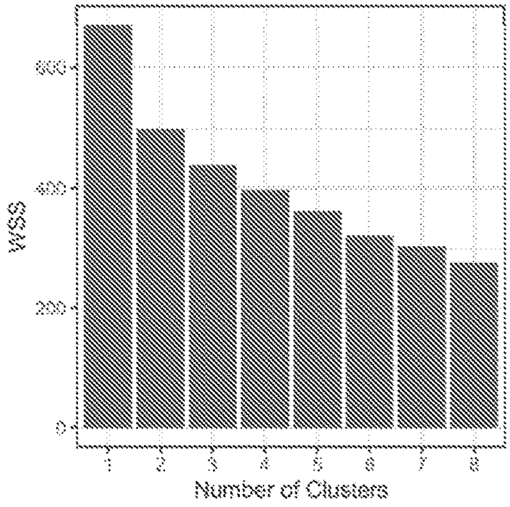
Figure 21C:
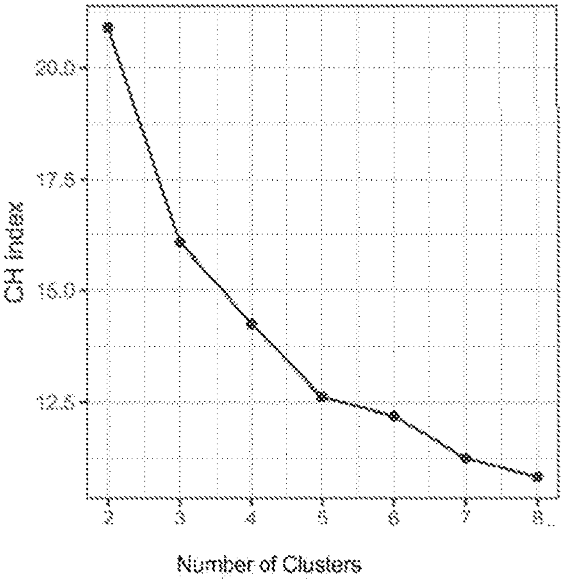
Figure 21D:
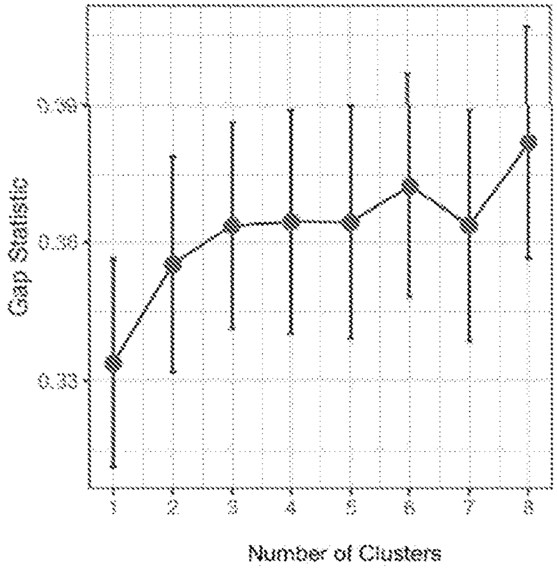

Cntnap2 is a member of the neurexin gene family, which functions as a cell adhesion molecule between neurons and glia (Poliak, S. et al., Neuron (1999) 24:1037-1047). Mutations in Cntnap2 have been linked to neurological disorders such as ASD, schizophrenia, bipolar disorder, and epilepsy (Toma, C. et al., PLoS Genetics (2018) 14:e1007535). Cntnap2 knockout mice have previously been shown to have mild gait effects, with increased stride speed leading to decreased stride duration (Brunner, D. et al., PloS One (2015) 10(8):e0134572). Model M2 was used to compare our results to the previous study and found that Cntnap2 mice show significant differences in a majority of the gait measures (FIG. 16). These mice are significantly smaller in body length and weight than controls (FIG. 14D, FIG. 16C). In the open field, Cntnap2 mice were not hyperactive (FIG. 11C) but showed a markedly increased stride speed (M1, FIG. 11A, C and FIG. 16C). These results argue that the Cntnap2 mice do not travel more, but take quicker steps when moving, similar to Ts65Dn mice.

Figure 11A:
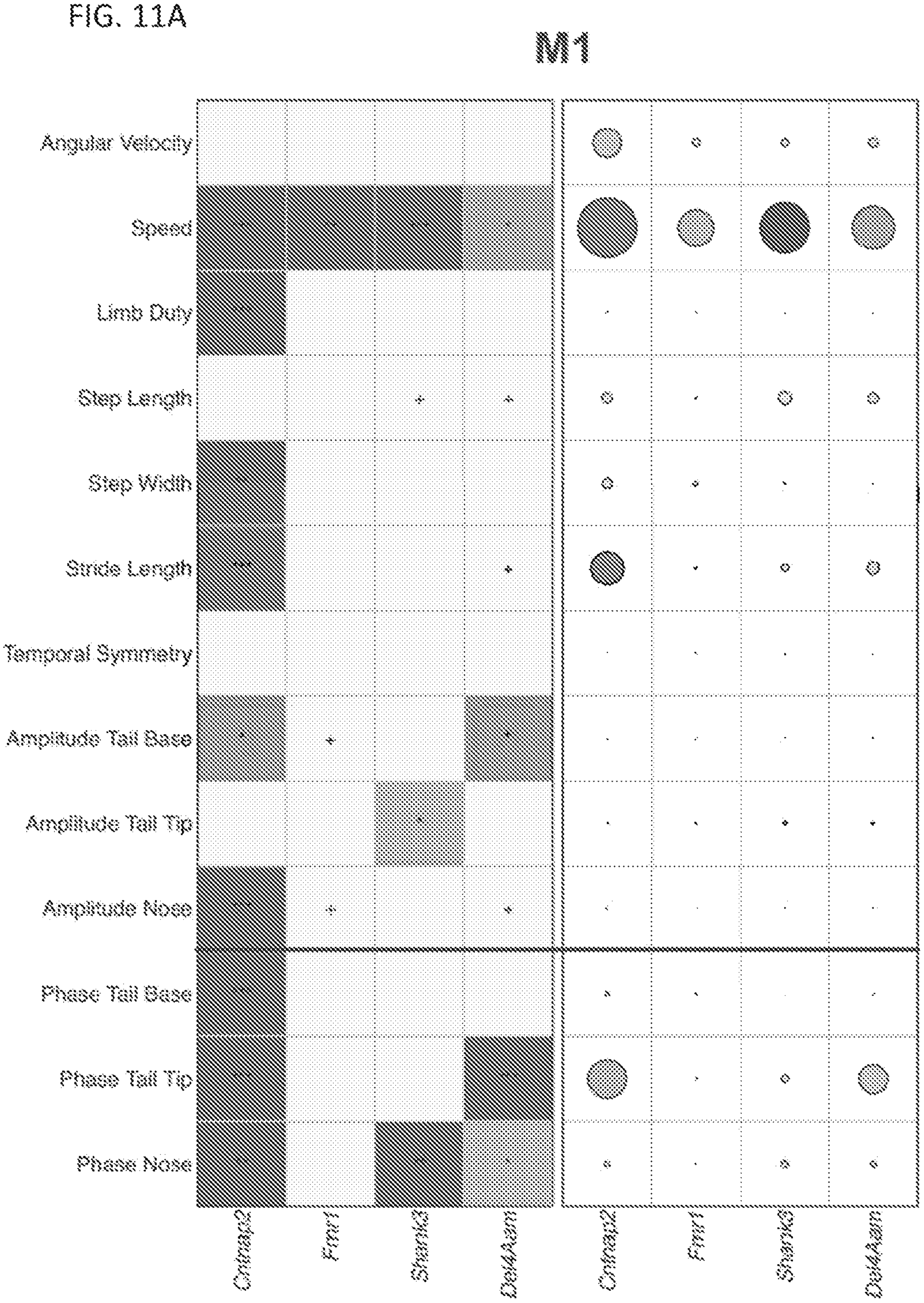
FIG. 11A-F provides tables and graphs illustrating genetic validation of autism mutants.
Figure 11B:
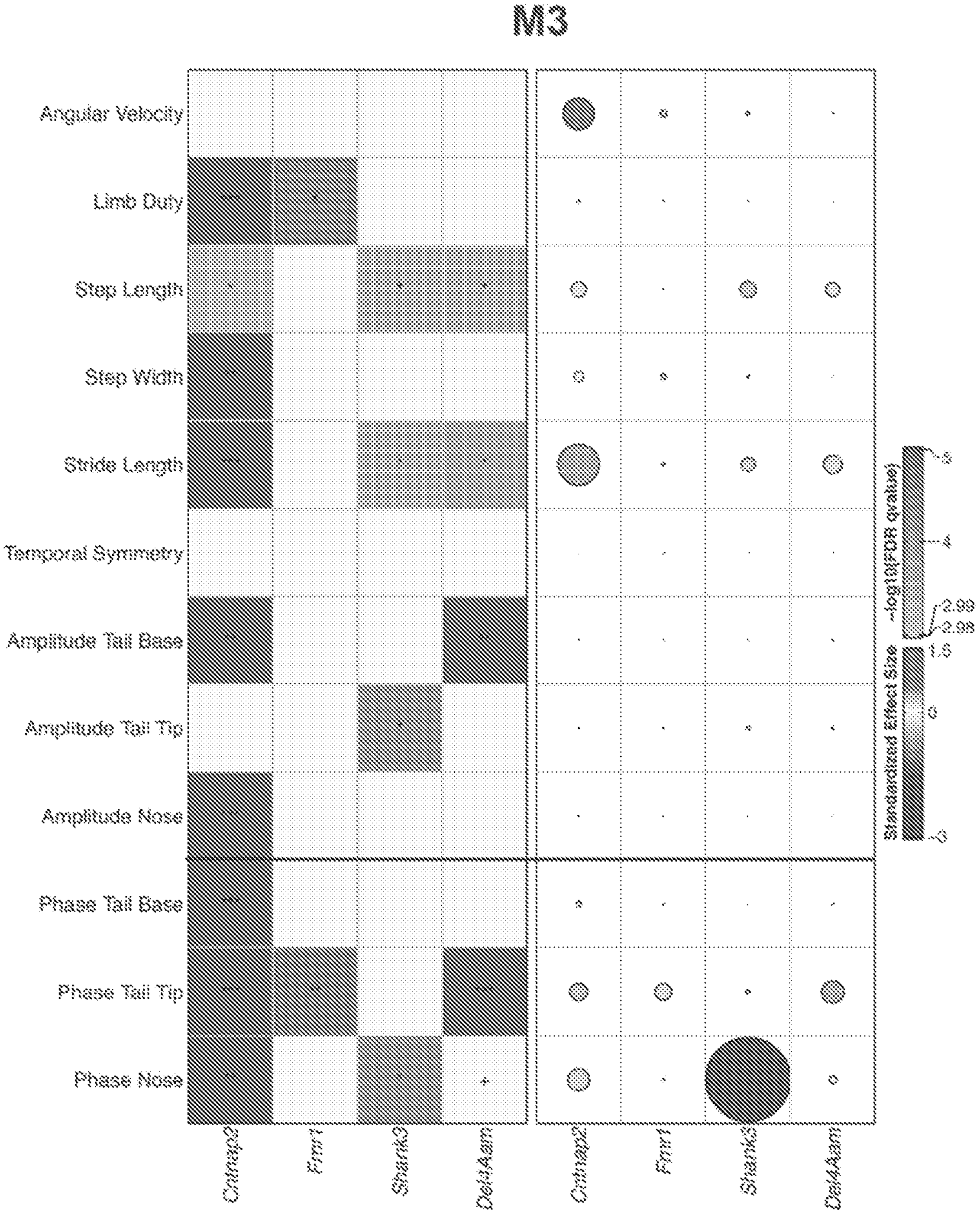
Figure 11C:
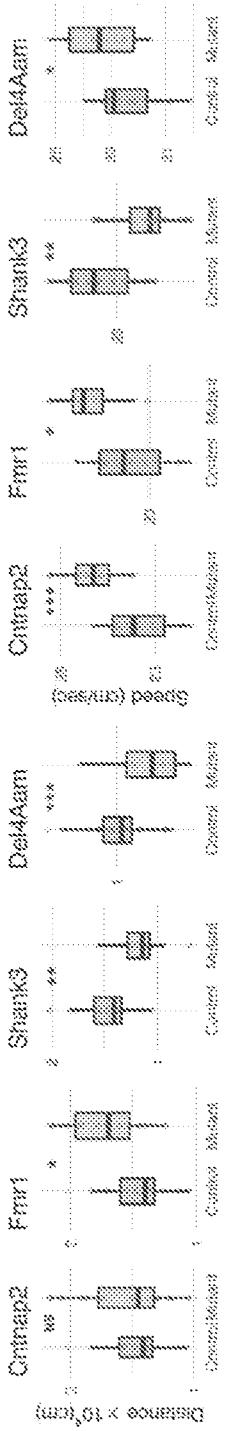
Figure 11D:
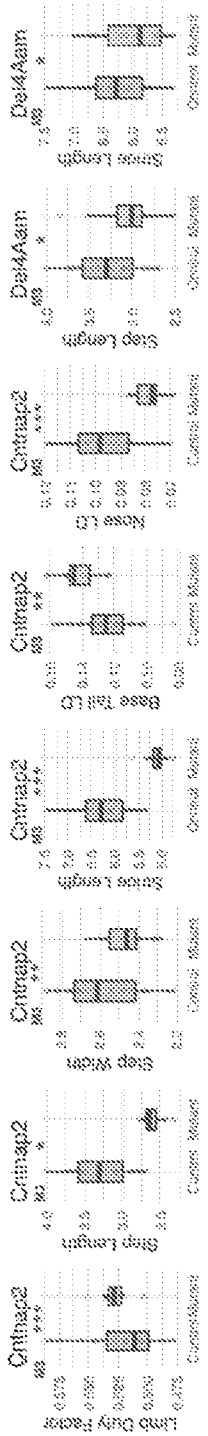
Figure 11E:
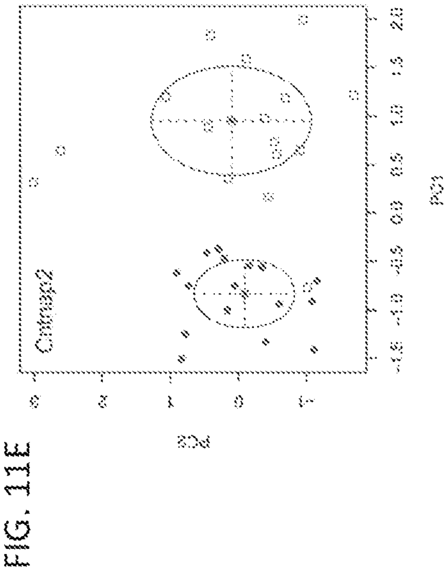
Figure 11F:
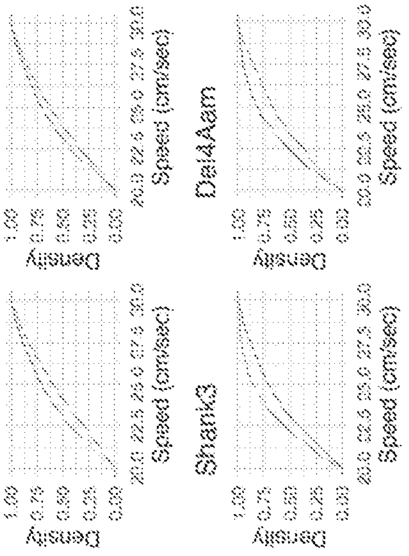

Because Cntnap2 mice are smaller and have faster stride speeds, results from M3 were used to determine if gait parameters are altered after adjusting for body size and stride speed (FIG. 14D). Results indicated that Cntnap2 mice were significantly different from controls for a majority of the traditional gait metrics as well as whole body coordination measures in both models M1 and M3 (FIG. 11B). The Cntnap2 mice have reduced limb duty factor, step length, step width, and highly reduced stride length (FIG. 11B, D and FIG. 16C). The mice also showed altered phase of tail tip, base, and nose, as well as significant but small changes in amplitude of tail tip base and nose. Another salient feature of gait in Cntnap2 mice is the decrease in inter-animal variance compared to controls, particularly for limb duty factor (Fligner-Killeen test, $p<0.01$), step length (Fligner-Killeen test, $p<0.01$), and stride length (Fligner-Killeen test, $p<0.02$) (FIG. 11D). This may indicate a more stereotyped gait in these mutants. Combined, these results imply that Cntnap2 mice are not hyperactive as measured by total distance traveled in the open field, but are hyperactive at the individual stride level. They take quicker steps with shorter stride and step length, and narrower step width. Finally, studies were performed to distinguish Cntnap2 mice from controls based on all combined gait measures using unsupervised clustering. First, a principal component analysis (PCA) was performed on the linear gait phenotypes and then Gaussian mixture modeling (GMM) was used on the PCs to cluster the animals into two separate groups. It was determined that the gait metrics allowed Cntnap2 to be distinguished from controls (FIG. 11E). This analysis argued that Cntnap2 mice could be distinguished from controls based on its gait patterns in the open field, and that these phenotypes are more dramatic than previously detected (Brunner, D. et al., PloS One (2015) 10(8):e0134572).

Mutations in Shank3, a scaffolding postsynaptic protein, have been found in multiple cases of ASD (Durand, C. M. et al., Nat Genet (2007) 39:25-27). Mutations in Fmr, a RNA binding protein that functions as a translational regulator, are associated with Fragile X syndrome, the most commonly inherited form of mental illness in humans (Crawford, D. C. et al., Genetics in Medicine (2001) 3:359-371). Fragile X syndrome has a broad spectrum of phenotypes that overlaps with ASD features (Belmonte, M. K. and Bourgeron, T. Nat Neurosci (2006) 9:1221-1225). Del4Aam mice contain a deletion of 0.39 Mb on mouse chromosome 7 that is syntenic to human chromosome 16p11.2 (Horev, G. et al., PNAS (2011) 108:17076-17081). Copy number variations (CNVs) of human 16p11.2 have been associated with a variety of ASD features, including intellectual disability, stereotypy, and social and language deficits (Weiss, L. A. et al., NEJM (2008) 358:667-675). Fmr1 mutant mice travel more in the open field (FIG. 11C) and have higher stride speed (FIG. 11A, C). When adjusted for stride speed and body length (M3) these mice had slight but significant changes in limb duty factor in M2 and M3. Shank3 and Del4Aam are both hypoactive in the open field compared to controls. Shank3 mice had a significant decrease in stride speed, whereas Del4Aam mice had faster stride speeds (FIG. 11A, C). All three statistical models show a suggestive or significant decrease in step length in both strains. Using M3, it was determined that Shank3 had longer step and stride length, whereas Del4Aam had shorter steps and strides. In whole body coordination, Shank3 mice had a decrease in nose phase and Del4Aam had an increase in tail tip phase. These results indicated that, even though both Shank3 and Del4Aam are hypoactive in the open field, Shank3 takes slower and longer strides and steps, whereas Del4Aam takes faster strides with shorter steps and strides. Both mutants have some defects in whole body coordination. In sum, it was determined that each of the ASD models had some gait deficits, with Cntnap2 having the strongest phenotypes. All had some change in stride speed, although the directionality of change and the variance of the phenotype differ.

Strain Survey

Figure 12A:
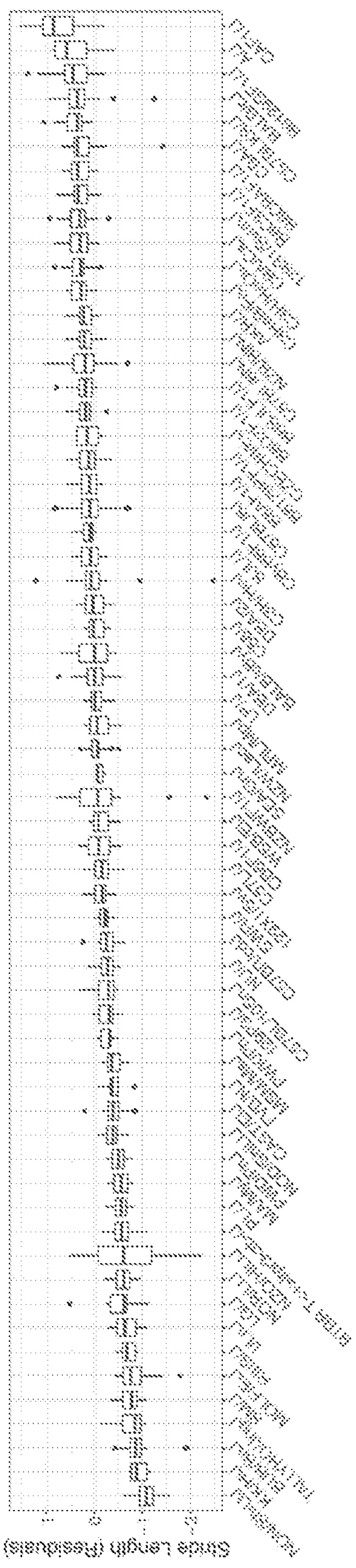
FIG. 12A-E shows results from strains tested.
Figure 12B:
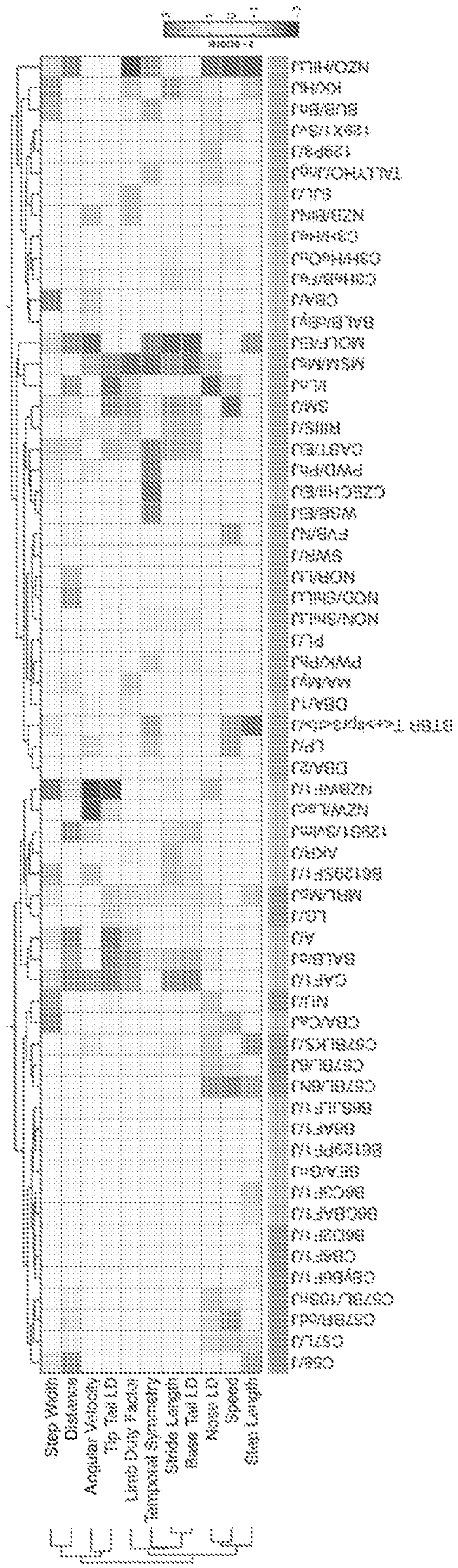

After validation of the analysis methods, experiments were performed in order to understand the range of gait and posture phenotypes in the open field in standard laboratory mouse strains. Forty four classical inbred laboratory strains were surveyed, 7 wild derived inbred strains, and 11 F1 hybrid strains (1898 animals, 1,740 hours of video). All animals were isogenic and both males and females were surveyed in a one hour open field assay (FIG. 14E) (Geuther, B. Q. et al., Commun Biol (2019) 2:1-11). Gait metrics were then extracted from each video and the data analyzed on a per-animal level (FIG. 12A-B, FIG. 17, and FIG. 18). Stride data was analyzed when animals were traveling in medium speed (20 to 30 cm/sec) and in a straight direction (angular velocity between −20 to +20 degrees/sec). Such a selective analysis could be performed because of the large amount of data that could be collected and processed in freely moving mice. Because these mice varied considerably in their size, residuals from M1 that adjusts for body size (Geuther, B. Q. et al., Commun Biol (2019) 2:1-11) were used. M1 allowed extraction of stride speed as a feature, which was determined to be important in ASD mutants. In order to visualize differences between strains, a z-score was calculated for each strain's phenotype and k-means clustering was performed (FIG. 12B). Overall, high inter-strain variability was observed in most of the classical gait and whole body posture metrics, indicating high levels of heritability of these traits. Emerging patterns were also observed in open field gait movements of laboratory mouse with certain strains showing similar behaviors.

Figure 12D:
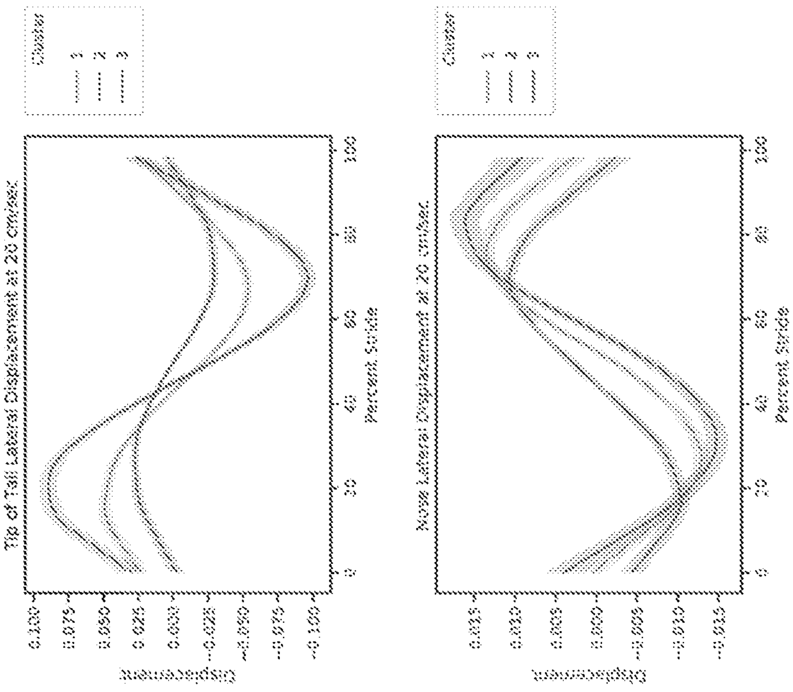
Figure 12C:
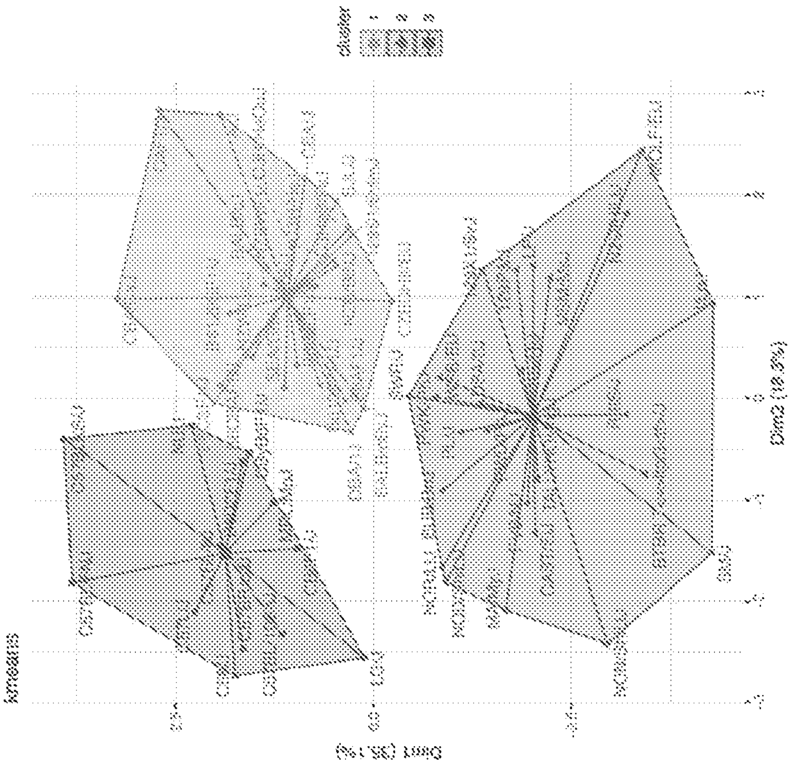
Figure 12E:
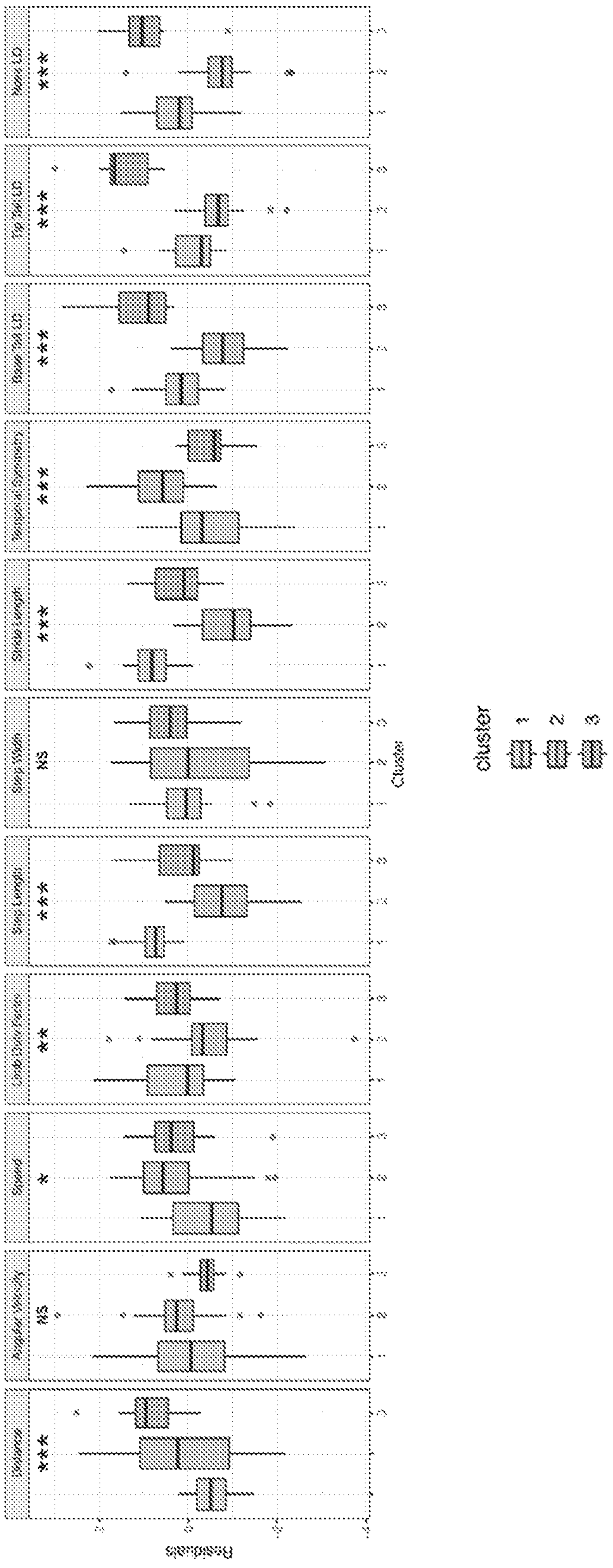

Studies were performed to determine if strains could be clustered based on their open field gait and posture phenotypes. A k-means clustering algorithm was applied on the principal components obtained by performing a PCA on the original linear gait features, as was done for the Cntnap2 mutant. Circular phase metrics were not included in the clustering analysis as both PCA and k-means clustering algorithms assume the metrics to lie in a Euclidean space. The first 2 PCs were selected as they explain 53% of the total variance in the original feature space. Four criteria were looked at in order to assess the quality of clustering and an optimal number of clusters in the k-means clustering algorithm was chosen, all of which indicated 3 optimal clusters (FIG. 21). It was determined that there were three clusters of strains that could be distinguished based on their open field gait behaviors (FIG. 12C-E). Cluster 1 consisted of mostly classical strains such as A/J, C3H/HeJ, 129S1/SvImJ; cluster 2 consisted of several classical strains and a large number of wild derived strains such as MOLF/EiJ and CAST/EiJ. Cluster 3 mainly consisted of C57 and related strains, including the reference C57BL/6J. A consensus stride phase plot of the nose and tail tip for each cluster was constructed. Cluster 3 had much higher amplitude, while clusters 1 and 2 had similar amplitude but shifted phase offset (FIG. 12D). An examination of the linear gait metrics revealed individual metrics that distinguished the clusters (FIG. 12E). For example, cluster 1 had longer stride and step length, while cluster 3 had higher lateral displacement of tail base and tip, while cluster 2 had low lateral displacement of nose. Overall, an analysis of individual metrics revealed a significant difference in 9 of 11 measures. Combined, this analysis revealed high levels of heritable variation in gait and whole body posture in the laboratory mouse. A combined analysis using multidimensional clustering of these metrics found three subtypes of gait in the laboratory mouse. The results also showed that the reference mouse strain, C57BL/6J, is distinct from other common mouse strains and wild derived strains.

GWAS

Figure 13A:
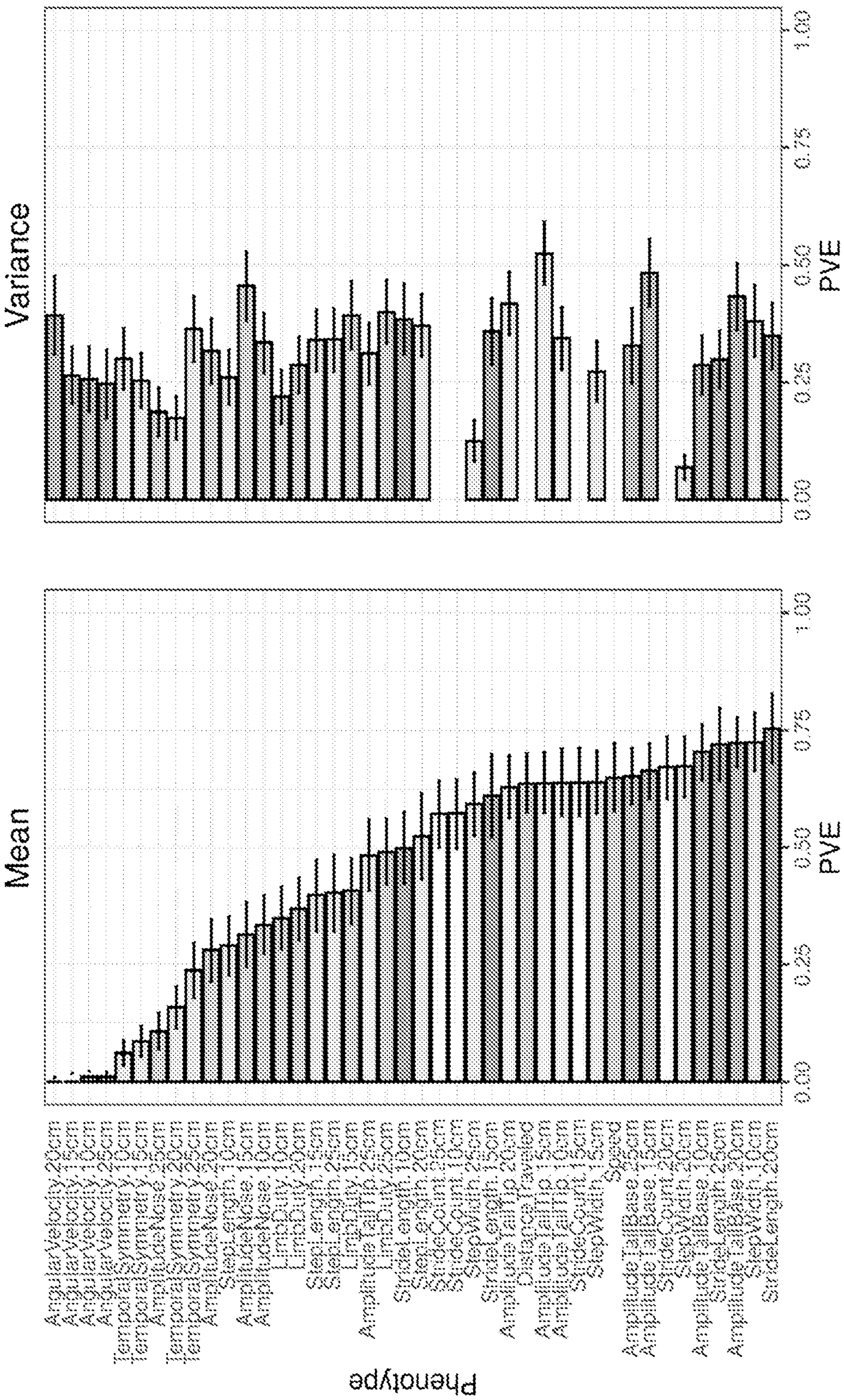
FIG. 13A-D provides GWAS results for gait phenotypes.

The strain survey demonstrated that the gait features measured were highly variable, and therefore, studies were performed to investigate the heritable components and the genetic architecture of mouse gait in the open field. In human GWAS, both mean and variance of gait traits are highly heritable (Adams, H. H. et al., J of Gerontol A Biol Sci Med Sci (2016) 71:740-746). The strides of each animal were separated into four different bins according to the speed it was travelling (10-15, 15-20, 20-25, and 25-30 cm/s) and the mean and variance of each trait were calculated for each animal in order to conduct a GWAS to identify Quantitative Trait Loci (QTL) in the mouse genome. GEMMA (Zhou, X. and Stephens, M. Nat Genet (2012) 44: 821-824) was used to conduct a genome-wide association analysis using a linear mixed model, taking into account sex and body length as fixed effects, and population structure as a random effect. Because linear mixed models do not handle circular values, phase gait data was excluded from this analysis. The heritability was estimated by determining the proportion of variance of a phenotype that is explained by the typed genotypes (PVE) (FIG. 13A left panel). Heritability of gait measures showed a broad range and the majority of the phenotypes are moderately to highly heritable. The mean phenotypes with lowest heritability are angular velocity and temporal symmetry, indicating that variance in the symmetrical nature of gait or turning behaviors were not due to genetic variance in the laboratory mouse. In contrast, it was found that measures of whole body coordination (amplitude measures) and traditional gait measures were moderately to highly heritable. Variance of phenotypes showed moderate heritability, even for traits with low heritability of mean traits (FIG. 13A right panel). For instance, mean AngularVelocity phenotypes have low heritability (PVE<0.1), whereas the variance AngularVelocity phenotypes have moderate heritability (PVE between 0.25-0.4). These heritability results indicated that the gait and posture traits are appropriate for GWAS of mean and variance traits.

Figures 13B, 13C, 13D:
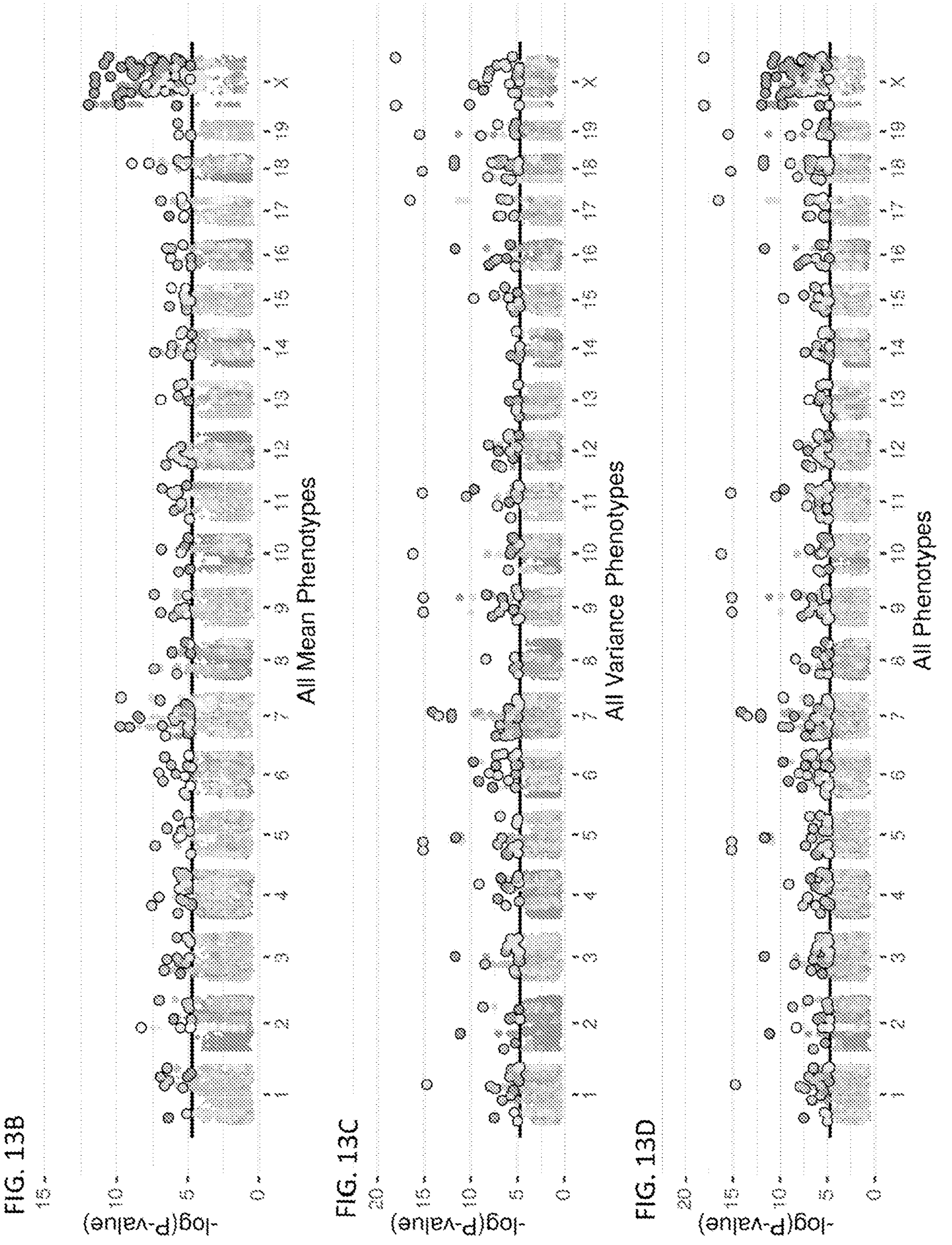

For significance threshold, an empirical p-value correction was calculated for the association of a SNP with a phenotype by shuffling the values (total distance traveled in the open field) between the individuals 1000 times. In each permutation, the lowest p-value was extracted to find the threshold that represented a corrected p-value of 0.05 (1.9× 10-5). The minimal p-value over all mean phenotypes, variance phenotypes, and both classes combined for each SNP was taken to generate combined Manhattan plots (FIG. 13B-D). Each SNP is colored according to the phenotype associated to the SNP with the lowest p-value. The different speed bins were usually consistent for each phenotype and it was decided to combine all bins of the same phenotype by taking the minimal p-value of the four bins for each SNP.

It was determined that 239 QTL for mean traits and 239 QTL for variance traits (FIG. 13B-C). The least heritable phenotype, mean AngularVelocity, showed only one significant associated genomic region, whereas the variance of AngularVelocity had 53 associated genomic loci. The phenotype with the most associated loci was stride count with 95 loci. Overall, when considering all the phenotypes together, 400 significant genomic regions associated with at least one phenotype (FIG. 22) were found, indicating only 78 QTL were identified for both a mean phenotype and a variance phenotype. Most phenotypes had limited to no overlap between QTL associated with the mean of the feature and its variance. Of note, QTL associated with mean TemporalSymmetry and variance TemporalSymmetry had a lot of overlapping regions. Out of 28 loci associated with the mean phenotype and 52 with variance, ten QTL overlapped. These data argue that the genetic architecture of mean and variance traits in the mouse are largely independent. These results also begin to outline the genetic landscape of mouse gait and posture in the open field.

Discussion

Gait and posture are an important indicator of health and are perturbed in many neurological, neuromuscular, and neuropsychiatric diseases. The goal of these experiments was to develop a simple and reliable automated system that is capable of performing pose estimation on mice and to extract key gait and posture metrics from pose. The information herein presents a solution that allows researchers to adapt a video imaging system used for open field analysis to extract gait metrics. The approach has some clear advantages and limitations. The methods permit processing a large amount of data with low effort and low cost because the only data that needs to be captured is top-down gray scale video of a mouse in an open field, and all pose estimation and gait metric extraction is fully automated after that. Because the method does not require expensive specialized equipment, it is also possible to allow the mouse time to acclimate to the open field and collect data over long periods of time. Additionally the methods of the invention allow the animal to move of its own volition (unforced behavior) in an environment that is familiar to it, a more ethologically relevant assay (Jacobs, B. Y. et al., Curr Pain Headache Rep (2014) 18:456). It was not possible to measure kinetic properties of gait because of the use of video methods (Lakes, E. H. & Allen, K. D. Osteoarthr Cartil (2016) 24:1837-1849). The decision to use top-down video also meant that some pose keypoints were often occluded by the mouse's body. The pose estimation network is robust to some amount of occlusion as is the case with the hind paws but the forepaws, which are almost always occluded during gait, have pose estimates, which are too inaccurate and so have been excluded from the analysis. Regardless, in all genetic models that were tested, hind paw data was sufficient to detect robust differences in gait and body posture. In addition, the ability to analyze large amounts of data in free moving animals, proved to be highly sensitive, even with very strict heuristic rules around what was considered to be a gait.

The gait measures that were extracted are commonly quantified in experiments (e.g. step width and stride length), but measures of whole body coordination such as lateral displacement and phase of tail are typically not measured in rodent gait experiments (phase and amplitude of keypoints during stride). Gait and whole body posture is frequently measured in humans as an endophenotype of psychiatric illness sanders2010gait, licari2020prevalence, flyckt1999neurological, walther2012motor. The results of the studies described herein in mice indicate that gait and whole body coordination measures are highly heritable and perturbed in disease models. Specifically, tests were performed to assess neurodegenerative (Sod1), neurodevelopmental (Down syndrome, Mecp2) and ASD models (Cntnap2, Shank3, FMR1, Del4Am) and altered gait features were identified in all of these mutants. Others have also found similar results with neurodegenerative models machado2015quantitative. Of note are the data for Down syndrome. In humans, miscoordination and clumsiness are prominent features of Down syndrome. In mouse models, this miscoordination was previously characterized in inkblot gait assays as a disorganized hind footprint. Here, the analysis revealed perturbed whole body coordination differences between control and Tn65Dn mice. The approach described herein thus enables quantitation of a previously qualitative trait.

The analysis of a large number of mouse strains for gait and posture identified three distinct classes of overall movement. The reference C57BL/6J and related strains were found to belong to a distinct cluster separate from other common laboratory as well as wild-derived strains. The main difference was seen in the high amplitude of tail and nose movement of the C57BL/6 and related strains. This may be important when analyzing gait and posture in differing genetic backgrounds. The GWAS revealed 400 QTL for gait and posture in the open field for both mean and variance phenotypes. It was found that the mean and variance of traits are regulated by distinct genetic loci. Indeed, methods of the invention identified that most variance phenotypes show moderate heritability, even for mean traits with low heritability. Human GWAS have been conducted for gait and posture, albeit with underpowered samples, which has led to good estimates of heritability but only a few significantly associated loci heritability. The results presented herein in the mouse support a conclusion that a well-powered study in humans may identify hundreds of genetic factors that regulates gait and posture.

Example 2

Devices and Systems

One or more of the machine learning models of the system(s) 150 may take many forms, including a neural network. A neural network may include a number of layers, from an input layer through an output layer. Each layer is configured to take as input a particular type of data and output another type of data. The output from one layer is taken as the input to the next layer. While values for the input data/output data of a particular layer are not known until a neural network is actually operating during runtime, the data describing the neural network describes the structure, parameters, and operations of the layers of the neural network.

One or more of the middle layers of the neural network may also be known as the hidden layer. Each node of the hidden layer is connected to each node in the input layer and each node in the output layer. In the case where the neural network comprises multiple middle networks, each node in a hidden layer will connect to each node in the next higher layer and next lower layer. Each node of the input layer represents a potential input to the neural network and each node of the output layer represents a potential output of the neural network. Each connection from one node to another node in the next layer may be associated with a weight or score. A neural network may output a single output or a weighted set of possible outputs.

In some embodiments, the neural network may be a convolutional neural network (CNN), which may regularized versions of multilayer perceptrons. Multilayer perceptrons may be fully connected networks, that is, each neuron in one layer is connected to all neurons in the next layer.

In one aspect, the neural network may be constructed with recurrent connections such that the output of the hidden layer of the network feeds back into the hidden layer again for the next set of inputs. Each node of the input layer connects to each node of the hidden layer. Each node of the hidden layer connects to each node of the output layer. The output of the hidden layer is fed back into the hidden layer for processing of the next set of inputs. A neural network incorporating recurrent connections may be referred to as a recurrent neural network (RNN).

In some embodiments, the neural network may be a long short-term memory (LSTM) network. In some embodiments, the LSTM may be a bidirectional LSTM. The bidirectional LSTM runs inputs from two temporal directions, one from past states to future states and one from future states to past states, where the past state may correspond to characteristics for the video data for a first time frame and the future state may corresponding to characteristics for the video data for a second subsequent time frame.

Processing by a neural network is determined by the learned weights on each node input and the structure of the network. Given a particular input, the neural network determines the output one layer at a time until the output layer of the entire network is calculated.

Connection weights may be initially learned by the neural network during training, where given inputs are associated with known outputs. In a set of training data, a variety of training examples are fed into the network. Each example typically sets the weights of the correct connections from input to output to 1 and gives all connections a weight of 0. As examples in the training data are processed by the neural network, an input may be sent to the network and compared with the associated output to determine how the network performance compares to the target performance. Using a training technique, such as back propagation, the weights of the neural network may be updated to reduce errors made by the neural network when processing the training data.

Various machine learning techniques may be used to train and operate models to perform various steps described herein, such as user recognition feature extraction, encoding, user recognition scoring, user recognition confidence determination, etc. Models may be trained and operated according to various machine learning techniques. Such techniques may include, for example, neural networks (such as deep neural networks and/or recurrent neural networks), inference engines, trained classifiers, etc. Examples of trained classifiers include Support Vector Machines (SVMs), neural networks, decision trees, AdaBoost (short for "Adaptive Boosting") combined with decision trees, and random forests. Focusing on SVM as an example, SVM is a supervised learning model with associated learning algorithms that analyze data and recognize patterns in the data, and which are commonly used for classification and regression analysis. Given a set of training examples, each marked as belonging to one of two categories, an SVM training algorithm builds a model that assigns new examples into one category or the other, making it a non-probabilistic binary linear classifier. More complex SVM models may be built with the training set identifying more than two categories, with the SVM determining which category is most similar to input data. An SVM model may be mapped so that the examples of the separate categories are divided by clear gaps. New examples are then mapped into that same space and predicted to belong to a category based on which side of the gaps they fall on. Classifiers may issue a "score" indicating which category the data most closely matches. The score may provide an indication of how closely the data matches the category.

In order to apply the machine learning techniques, the machine learning processes themselves need to be trained. Training a machine learning component such as, in this case, one of the first or second models, requires establishing a "ground truth" for the training examples. In machine learning, the term "ground truth" refers to the accuracy of a training set's classification for supervised learning techniques. Various techniques may be used to train the models including backpropagation, statistical learning, supervised learning, semi-supervised learning, stochastic learning, or other known techniques.

Figure 23:
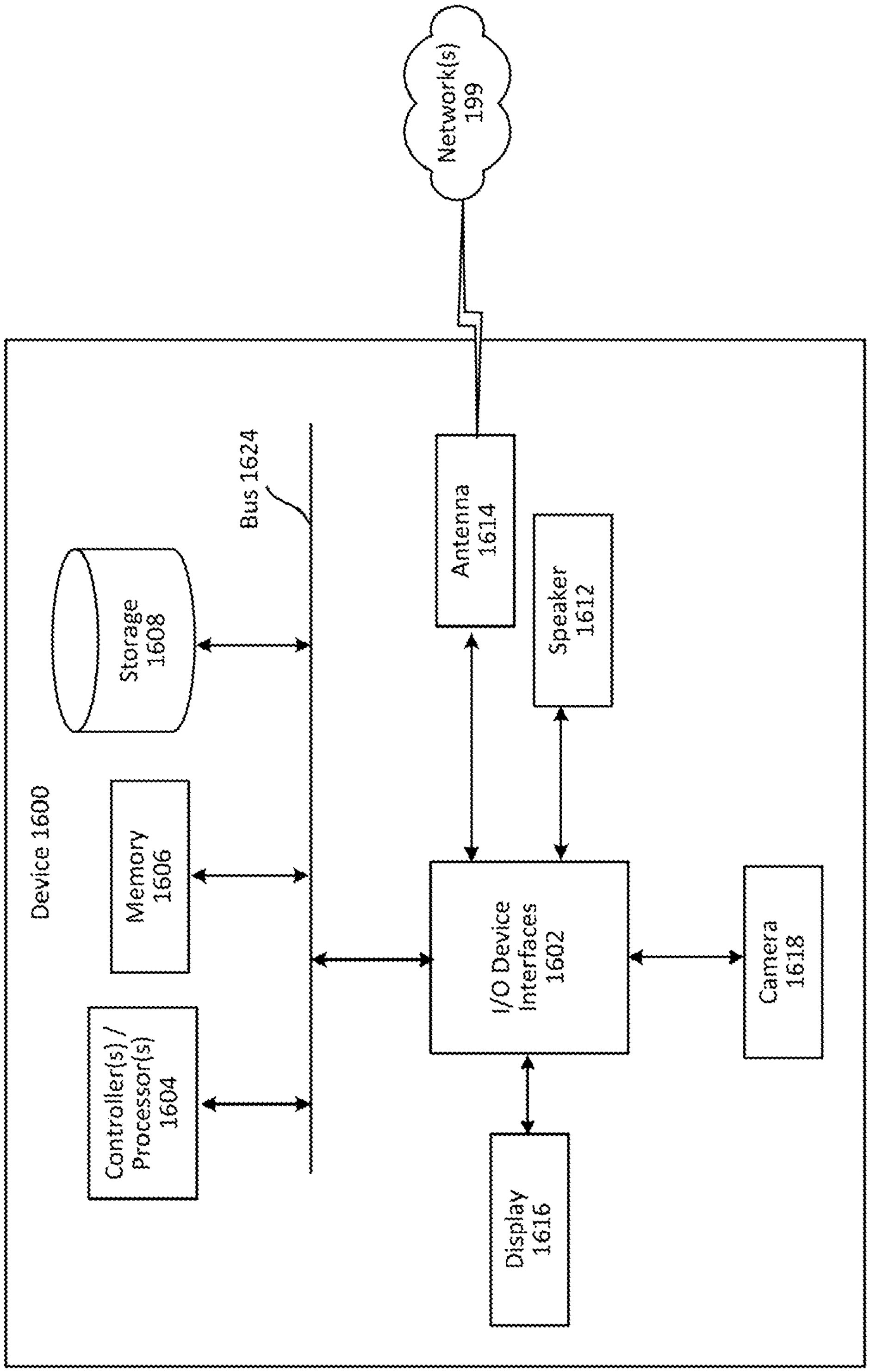
FIG. 23 is a block diagram conceptually illustrating example components of a device according to embodiments of the present disclosure.
Figure 24:
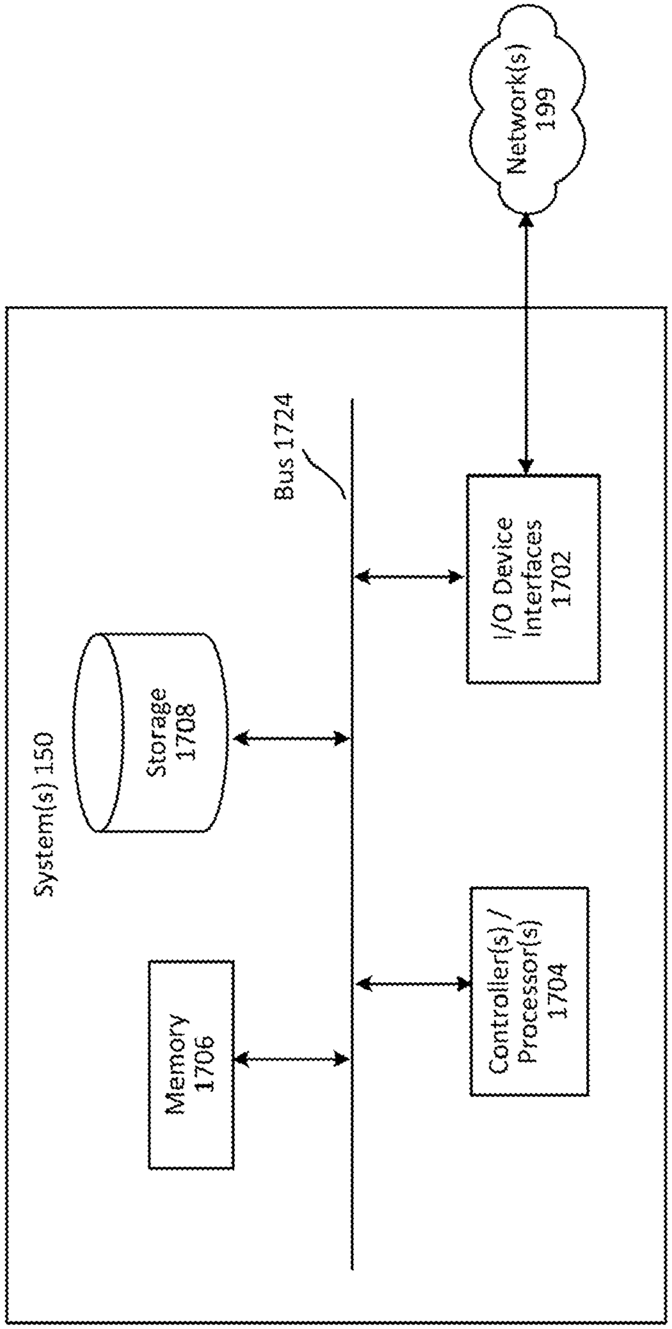
FIG. 24 is a block diagram conceptually illustrating example components of a server according to embodiments of the present disclosure.

FIG. 23 is a block diagram conceptually illustrating a device 1600 that may be used with the system. FIG. 24 is a block diagram conceptually illustrating example components of a remote device, such as the system(s) 150, which may assist processing of video data, identifying subject behavior, etc. A system(s) 150 may include one or more servers. A "server" as used herein may refer to a traditional server as understood in a server/client computing structure but may also refer to a number of different computing components that may assist with the operations discussed herein. For example, a server may include one or more physical computing components (such as a rack server) that are connected to other devices/components either physically and/or over a network and is capable of performing computing operations. A server may also include one or more virtual machines that emulates a computer system and is run on one or across multiple devices. A server may also include other combinations of hardware, software, firmware, or the like to perform operations discussed herein. The server(s) may be configured to operate using one or more of a client-server model, a computer bureau model, grid computing techniques, fog computing techniques, mainframe techniques, utility computing techniques, a peer-to-peer model, sandbox techniques, or other computing techniques.

Multiple systems 150 may be included in the overall system of the present disclosure, such as one or more systems 150 for performing keypoint/body part tracking, one or more systems 150 for gait metrics extraction, one or more systems 150 for posture metrics extraction, one or more systems 150 for statistical analysis, one or more systems 150 for training/configuring the system, etc. In operation, each of these systems may include computer-readable and computer-executable instructions that reside on the respective device 150, as will be discussed further below.

Each of these devices (1600/150) may include one or more controllers/processors (1604/1704), which may each include a central processing unit (CPU) for processing data and computer-readable instructions, and a memory (1606/1706) for storing data and instructions of the respective device. The memories (1606/1706) may individually include volatile random access memory (RAM), non-volatile read only memory (ROM), non-volatile magnetoresistive memory (MRAM), and/or other types of memory. Each device (1600/150) may also include a data storage component (1608/1708) for storing data and controller/processor-executable instructions. Each data storage component (1608/1708) may individually include one or more non-volatile storage types such as magnetic storage, optical storage, solid-state storage, etc. Each device (1600/150) may also be connected to removable or external non-volatile memory and/or storage (such as a removable memory card, memory key drive, networked storage, etc.) through respective input/output device interfaces (1602/1702).

Computer instructions for operating each device (1600/150) and its various components may be executed by the respective device's controller(s)/processor(s) (1604/1704), using the memory (1606/1706) as temporary "working" storage at runtime. A device's computer instructions may be stored in a non-transitory manner in non-volatile memory (1606/1706), storage (1608/1708), or an external device(s). Alternatively, some or all of the executable instructions may be embedded in hardware or firmware on the respective device in addition to or instead of software.

Each device (1600/150) includes input/output device interfaces (1602/1702). A variety of components may be connected through the input/output device interfaces (1602/1702), as will be discussed further below. Additionally, each device (1600/150) may include an address/data bus (1624/1724) for conveying data among components of the respective device. Each component within a device (1600/150) may also be directly connected to other components in addition to (or instead of) being connected to other components across the bus (1624/1724).

Referring to FIG. 23, the device 1600 may include input/output device interfaces 1602 that connect to a variety of components such as an audio output component such as a speaker 1612, a wired headset or a wireless headset (not illustrated), or other component capable of outputting audio. The device 1600 may additionally include a display 1616 for displaying content. The device 1600 may further include a camera 1618.

Via antenna(s) 1614, the input/output device interfaces 1602 may connect to one or more networks 199 via a wireless local area network (WLAN) (such as WiFi) radio, Bluetooth, and/or wireless network radio, such as a radio capable of communication with a wireless communication network such as a Long Term Evolution (LTE) network, WiMAX network, 3G network, 4G network, 5G network, etc. A wired connection such as Ethernet may also be supported. Through the network(s) 199, the system may be distributed across a networked environment. The I/O device interface (1602/1702) may also include communication components that allow data to be exchanged between devices such as different physical servers in a collection of servers or other components.

The components of the device(s) 1600 or the system(s) 150 may include their own dedicated processors, memory, and/or storage. Alternatively, one or more of the components of the device(s) 1600, or the system(s) 150 may utilize the I/O interfaces (1602/1702), processor(s) (1604/1704), memory (1606/1706), and/or storage (1608/1708) of the device(s) 1600, or the system(s) 150, respectively.

As noted above, multiple devices may be employed in a single system. In such a multi-device system, each of the devices may include different components for performing different aspects of the system's processing. The multiple devices may include overlapping components. The components of the device 1600, and the system(s) 150, as described herein, are illustrative, and may be located as a stand-alone device or may be included, in whole or in part, as a component of a larger device or system.

The concepts disclosed herein may be applied within a number of different devices and computer systems, including, for example, general-purpose computing systems, video/image processing systems, and distributed computing environments.

The above aspects of the present disclosure are meant to be illustrative. They were chosen to explain the principles and application of the disclosure and are not intended to be exhaustive or to limit the disclosure. Many modifications and variations of the disclosed aspects may be apparent to those of skill in the art. Persons having ordinary skill in the field of computers and speech processing should recognize that components and process steps described herein may be interchangeable with other components or steps, or combinations of components or steps, and still achieve the benefits and advantages of the present disclosure. Moreover, it should be apparent to one skilled in the art, that the disclosure may be practiced without some or all of the specific details and steps disclosed herein.

Aspects of the disclosed system may be implemented as a computer method or as an article of manufacture such as a memory device or non-transitory computer readable storage medium. The computer readable storage medium may be readable by a computer and may comprise instructions for causing a computer or other device to perform processes described in the present disclosure. The computer readable storage medium may be implemented by a volatile computer memory, non-volatile computer memory, hard drive, solid-state memory, flash drive, removable disk, and/or other media. In addition, components of system may be implemented as in firmware or hardware.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements, and/or steps are in any way required for one or more embodiments or that one or more embodiments necessarily include logic for deciding, with or without other input or prompting, whether these features, elements, and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

All literature references, patents and patent applications and publications that are cited or referred to in this application are incorporated by reference in their entirety herein.

What is claimed is:

1. A computer-implemented method comprising:

receiving video data representing a video capturing movements of a subject, wherein the video captures subject-determined movements of the subject in an open arena with a top-down view;

processing the video data using a trained deep convolutional neural network to generate a plurality of keypoint heatmaps, wherein each keypoint heatmap in the plurality of keypoint heatmaps represents a spatial probability distribution of a location of a respective body part of the subject;

identifying a location of a maximum value in each keypoint heatmap, wherein the location of the maximum value in each keypoint heatmap is a two-dimensional coordinate of the respective body part of the subject;

determining point data, tracking movement over a time period, of a set of body parts of the subject, wherein determining the point data comprises tracking the two-dimensional coordinate across a plurality of frames;

determining, using the point data, a plurality of stance phases and a corresponding plurality of swing phases represented in the video data during the time period;

determining, based on the plurality of stance phases and the plurality of swing phases, a plurality of stride intervals represented in the video data during the time period;

determining, using the point data, metrics data for the subject, the metrics data being based on each stride interval of the plurality of stride intervals;

comparing the metrics data for the subject to control metrics data; and determining, based on the comparing, a difference between the subject's metrics data and the control metrics data.

2. The computer-implemented method of claim 1, wherein the set of body parts comprises a nose, a left ear, a right ear, a base of a neck, a mid spine, a left hind paw, a right hind paw, a left forepaw, a right forepaw, a base of a tail, a middle of the tail, and a tip of the tail; and wherein the plurality of stance phases and the plurality of swing phases are determined based on a change in movement speed of the left hind paw and the right hind paw.

3. The computer-implemented method of claim 2, further comprising:

determining a transition from a first stance phase of the plurality of stance phases and a first swing phase of the plurality of swing phases based on a toe-off event of the left hind paw or the right hind paw; and determining a transition from a second swing phase of the plurality of swing phases to a second stance phase of the plurality of stance phases based on a foot strike event of the left hind paw or the right hind paw.

4. The computer-implemented method of claim 1, wherein the metrics data correspond to at least one of: (i) gait measurements of the subject during each stride interval, or to (ii) posture measurements of the subject during each stride interval.

5. The computer-implemented method of claim 1, wherein the set of body parts comprises a left hind paw and a right hind paw, and wherein determining the metrics data comprises:

determining, using the point data, a step length for each stride interval, the step length representing a distance that the right hind paw travels past a previous left hind paw strike;

determining, using the point data, a stride length using for each stride interval, the stride length representing a distance that the left hind paw travels during each stride interval; and determining, using the point data, a step width for each stride interval, the step width representing a distance between the left hind paw and the right hind paw.

6. The computer-implemented method of claim 1, wherein the set of body parts comprises a tail base, and wherein determining the metrics data comprises:

determining, using the point data, speed data of the subject based on movement of the tail base for each stride interval.

7. The computer-implemented method of claim 1, wherein the set of body parts comprises a tail base, and wherein determining the metrics data comprises:

determining, using the point data, a set of speed data of the subject based on movement of the tail base during a set of frames representing a stride interval of the plurality of stride intervals; and determining a stride speed, for the stride interval, by averaging the set of speed data.

8. The computer-implemented method of claim 1, wherein the set of body parts comprises a right hind paw and a left hind paw, and wherein determining the metrics data comprises:

determining, using the point data, first stance duration representing an amount of time that the right hind paw is in contact with ground during a stride interval of the plurality of stride intervals;

determining a first duty factor based on the first stance duration and a duration of the stride interval;

determining, using the point data, second stance duration representing an amount of time that the left hind paw is in contact with ground during the stride interval;

determining a second duty factor based on the second stance duration and the duration of the stride interval; and determining an average duty factor for the stride interval based on the first duty factor and the second duty factor.

9. The computer-implemented method of claim 1, wherein the set of body parts comprises a tail base and a neck base, and wherein determining the metrics data comprises:

determining, using the point data, a set of vectors connecting the tail base and the neck base during a set of frames representing a stride interval of the plurality of stride intervals; and determining, using the set of vectors, an angular velocity of the subject for the stride interval.

10. The computer-implemented method of claim 1, wherein the set of body parts comprises a spine center of the subject, wherein a stride interval of the plurality of stride intervals is associated with a set of frames of the video data, and wherein determining the metrics data comprises determining, using the point data, a displacement vector for the stride interval, the displacement vector connecting the spine center represented in a first frame of the set of frames and the spine center represented in a last frame of the set of frames.

11. The computer-implemented method of claim 10, wherein the set of body parts further comprises a nose of the subject, and wherein determining the metrics data comprises:

determining, using the point data, a set of lateral displacements of the nose for the stride interval based on a perpendicular distance of the nose from the displacement vector for each frame in the set of frames, and wherein each lateral displacement in the set of lateral displacements of the nose is further based on a body length of the subject.

12. The computer-implemented method of claim 11, wherein determining the metrics data further comprises determining a nose displacement phase offset by:

performing an interpolation using the set of lateral displacements of the nose to generate a smooth curve lateral displacement of the nose for the stride interval;

determining, using the smooth curve lateral displacement of the nose, when a maximum displacement of the nose occurs during the stride interval; and determining a percent stride location representing a percent of the stride interval that is completed when the maximum displacement of the nose occurs.

13. The computer-implemented method of claim 10, wherein the set of body parts further comprises a tail base of the subject, and wherein determining the metrics data comprises:

determining, using the point data, a set of lateral displacements of the tail base for the stride interval based on a perpendicular distance of the tail base from the displacement vector for each frame in the set of frames.

14. The computer-implemented method of claim 13, wherein determining the metrics data further comprises determining a tail base displacement phase offset by:

performing an interpolation using the set of lateral displacements of the tail base to generate a smooth curve lateral displacement of the tail base for the stride interval;

determining, using the smooth curve lateral displacement of the tail base, when a maximum displacement of the tail base occurs during the stride interval; and determining a percent stride location representing a percent of the stride interval that is completed when the maximum displacement of the tail base occurs.

15. The computer-implemented method of claim 10, wherein the set of body parts further comprises a tail tip of the subject, and wherein determining the metrics data comprises:

determining, using the point data, a set of lateral displacements of the tail tip for the stride interval based on a perpendicular distance of the tail tip from the displacement vector for each frame in the set of frames.

16. The computer-implemented method of claim 15, wherein determining the metrics data further comprises determining a tail tip displacement phase offset by:

performing an interpolation using the set of lateral displacements of the tail tip to generate a smooth curve lateral displacement of the tail tip for the stride interval;

determining, using the smooth curve lateral displacement of the tail tip, when a maximum displacement of the tail tip occurs during the stride interval; and determining a percent stride location representing a percent of the stride interval that is completed when the maximum displacement of the tail tip occurs.

17. The computer-implemented method of claim 1, wherein the control metrics data is obtained from a control organism or plurality thereof, and wherein the subject is an organism, and the control organism and the subject organism are the same species, and wherein the control organism is a laboratory strain of a species.

18. The computer-implemented method of claim 1, wherein the control metrics data is obtained from a control organism or plurality thereof, and wherein a statistically significant difference in the subject's metrics data compared to the control metrics data indicates a difference in a phenotype of the subject compared to a phenotype of the control organism, wherein the phenotypic difference indicates a presence of a disease or condition in the subject, and wherein the phenotypic difference indicates a difference between a genetic background of the subject and the genetic background of the control organism.

19. The computer-implemented method of claim 1, wherein the control metrics data is obtained from a control organism or plurality thereof, wherein a statistically significant difference in the subject's metrics data and the control metrics data indicates a difference in a genotype of the subject compared to a genotype of the control organism, and wherein the difference in the genotype of the subject and the genotype of the control organism indicates a strain difference between the subject and the control organism.

20. The computer-implemented method of claim 1, wherein the control metrics data is obtained from a control organism or plurality thereof, wherein a statistically significant difference in the subject's metrics data and the control metrics data indicates a difference in a genotype of the subject compared to a genotype of the control organism, and wherein the difference in the genotype of the subject and the genotype of the control organism indicates a presence of a disease or condition in the subject.

* * * * *